United States Patent
Ellis

(10) Patent No.: US 11,901,072 B2
(45) Date of Patent: *Feb. 13, 2024

(54) BIG DATA ARTIFICIAL INTELLIGENCE COMPUTER SYSTEM USED FOR MEDICAL CARE CONNECTED TO MILLIONS OF SENSOR-EQUIPPED SMARTPHONES CONNECTED TO THEIR USERS' CONFIGURABLE FOOTWEAR SOLES WITH SENSORS AND TO BODY SENSORS

(71) Applicant: Frampton E. Ellis, Jasper, FL (US)

(72) Inventor: Frampton E. Ellis, Jasper, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/332,066

(22) Filed: Jun. 9, 2023

(65) Prior Publication Data

US 2023/0335276 A1 Oct. 19, 2023

Related U.S. Application Data

(63) Continuation of application No. 17/402,004, filed on Aug. 13, 2021, now Pat. No. 11,715,561, which is a
(Continued)

(51) Int. Cl.
*G16H 40/67* (2018.01)
*G05B 19/048* (2006.01)
(Continued)

(52) U.S. Cl.
CPC .............. *G16H 40/67* (2018.01); *A41D 1/002* (2013.01); *A43B 1/0054* (2013.01); *A43B 3/34* (2022.01);
(Continued)

(58) Field of Classification Search
CPC ...... G16H 40/67; A41D 1/002; A43B 1/0054; A43B 3/34; A43B 3/38; A43B 7/14;
(Continued)

(56) References Cited

U.S. PATENT DOCUMENTS 2,514,108 A 7/1950 Vogt
3,978,259 A 8/1976 Hilton
(Continued)

FOREIGN PATENT DOCUMENTS

KR 1020090049572 A 5/2009
KR 10-2010-0089941 A 8/2010
(Continued)

OTHER PUBLICATIONS

Morris, S. J., et al., "Shoe-Integrated Sensor system for Wireless Gait Analysis and Real-Time Feedback," Proceedings of the Second Joint EMBS/BMES Conference, Houston, TX, USA, Oct. 23-26, 2002, pp. 2468-2469.
(Continued)

*Primary Examiner* — Omar Casillashernandez
(74) *Attorney, Agent, or Firm* — Mendelsohn Dunleavy, PC

(57) ABSTRACT

A big data artificial intelligence computer system is used for medical care connecting to sensor-equipped smartphones of users of footwear. The footwear has smartphone-connected soles with sensors and configurable structures. The smartphone is also connected to sensors located on the users' body, including proximate to its center of gravity and/or on the head. The web and/or cloud-based computer system is configured to use the big data techniques of machine learning in a database compiled from millions of smartphones to perform operations on billions of data sets from the smartphones of the footwear users. The correlations found from the big data operations provide solutions to medical problems of the footwear users involving their body structure and/or function. The solutions are implemented by configuring the users' footwear soles, including active configuration, including during running and/or walking to optimize corrections to the structure and/or function of their bodies.

30 Claims, 40 Drawing Sheets

Related U.S. Application Data continuation of application No. 16/749,665, filed on Jan. 22, 2020, now Pat. No. 11,120,909, which is a continuation of application No. 16/263,181, filed on Jan. 31, 2019, now Pat. No. 10,568,369, which is a continuation of application No. 15/995,166, filed on Jun. 1, 2018, now Pat. No. 10,226,082, which is a continuation-in-part of application No. 15/825,967, filed on Nov. 29, 2017, now Pat. No. 10,172,396, which is a continuation of application No. 15/358,533, filed on Nov. 22, 2016, now Pat. No. 9,877,523, which is a continuation-in-part of application No. 15/298,441, filed on Oct. 20, 2016, now Pat. No. 9,709,971, which is a continuation of application No. 15/164,650, filed on May 25, 2016, now Pat. No. 9,504,291, which is a continuation of application No. 14/922,408, filed on Oct. 26, 2015, now Pat. No. 9,375,047, which is a continuation of application No. 14/722,547, filed on May 27, 2015, now Pat. No. 9,207,660, which is a continuation of application No. 14/615,749, filed on Feb. 6, 2015, now Pat. No. 9,100,495, which is a continuation of application No. 14/605,177, filed on Jan. 26, 2015, now Pat. No. 9,160,836, and a continuation of application No. 14/605,192, filed on Jan. 26, 2015, now Pat. No. 9,063,529, which is a continuation of application No. 13/859,859, filed on Apr. 10, 2013, now Pat. No. 9,030,335, said application No. 14/605,177 is a continuation of application No. 13/859,859, filed on Apr. 10, 2013, now Pat. No. 9,030,335.

(60) Provisional application No. 62/762,671, filed on May 14, 2018, provisional application No. 62/709,431, filed on Jan. 19, 2018, provisional application No. 62/708,334, filed on Dec. 6, 2017, provisional application No. 62/606,281, filed on Sep. 18, 2017, provisional application No. 62/605,028, filed on Jul. 31, 2017, provisional application No. 62/603,930, filed on Jun. 16, 2017, provisional application No. 62/603,494, filed on Jun. 2, 2017, provisional application No. 62/496,258, filed on Oct. 12, 2016, provisional application No. 62/495,121, filed on Sep. 2, 2016, provisional application No. 62/392,654, filed on Jun. 8, 2016, provisional application No. 62/392,024, filed on May 18, 2016, provisional application No. 62/391,837, filed on May 13, 2016, provisional application No. 62/386,987, filed on Dec. 18, 2015, provisional application No. 62/386,921, filed on Dec. 16, 2015, provisional application No. 62/386,337, filed on Nov. 27, 2015, provisional application No. 61/852,038, filed on Mar. 15, 2013, provisional application No. 61/851,869, filed on Mar. 14, 2013, provisional application No. 61/851,598, filed on Mar. 11, 2013, provisional application No. 61/687,127, filed on Apr. 19, 2012, provisional application No. 61/687,072, filed on Apr. 18, 2012.

(51) Int. Cl.

| | |
|---|---|
| A61B 5/11 | (2006.01) |
| A43B 17/02 | (2006.01) |
| A43B 13/18 | (2006.01) |
| A41D 1/00 | (2018.01) |
| A61B 5/00 | (2006.01) |
| H04W 24/04 | (2009.01) |
| A61F 5/14 | (2022.01) |
| G08C 17/02 | (2006.01) |
| G05B 19/406 | (2006.01) |
| A61B 5/103 | (2006.01) |
| A43B 13/38 | (2006.01) |
| A43B 13/20 | (2006.01) |
| A43B 7/14 | (2022.01) |
| A43B 1/00 | (2006.01) |
| H04L 67/125 | (2022.01) |
| H04W 4/70 | (2018.01) |
| H04W 4/00 | (2018.01) |
| G05B 19/042 | (2006.01) |
| A61B 5/0265 | (2006.01) |
| H04M 1/72403 | (2021.01) |
| H04M 1/72412 | (2021.01) |
| H04W 12/084 | (2021.01) |
| A43B 3/34 | (2022.01) |
| A43B 3/38 | (2022.01) |
| H04W 84/18 | (2009.01) |
| A43B 3/00 | (2022.01) |
| A61B 5/08 | (2006.01) |
| A61B 5/145 | (2006.01) |
| A61B 5/024 | (2006.01) |
| A61B 5/01 | (2006.01) |
| A61B 5/021 | (2006.01) |

(52) U.S. Cl.
CPC ............... *A43B 3/38* (2022.01); *A43B 7/14* (2013.01); *A43B 13/18* (2013.01); *A43B 13/186* (2013.01); *A43B 13/189* (2013.01); *A43B 13/203* (2013.01); *A43B 13/38* (2013.01); *A43B 17/026* (2013.01); *A61B 5/0022* (2013.01); *A61B 5/0265* (2013.01); *A61B 5/1036* (2013.01); *A61B 5/1038* (2013.01); *A61B 5/11* (2013.01); *A61B 5/112* (2013.01); *A61B 5/1112* (2013.01); *A61B 5/1118* (2013.01); *A61B 5/1123* (2013.01); *A61B 5/6803* (2013.01); *A61B 5/6805* (2013.01); *A61B 5/6806* (2013.01); *A61B 5/686* (2013.01); *A61B 5/6807* (2013.01); *A61B 5/6817* (2013.01); *A61B 5/6831* (2013.01); *A61B 5/6878* (2013.01); *A61B 5/6891* (2013.01); *A61B 5/6895* (2013.01); *A61B 5/6898* (2013.01); *A61B 5/743* (2013.01); *A61F 5/14* (2013.01); *G05B 19/042* (2013.01); *G05B 19/048* (2013.01); *G05B 19/406* (2013.01); *G08C 17/02* (2013.01); *H04L 67/125* (2013.01); *H04M 1/72403* (2021.01); *H04M 1/72412* (2021.01); *H04W 4/00* (2013.01); *H04W 4/70* (2018.02); *H04W 12/084* (2021.01); *H04W 24/04* (2013.01); *A43B 1/00* (2013.01); *A43B 3/00* (2013.01); *A43B 13/20* (2013.01); *A61B 5/01* (2013.01); *A61B 5/021* (2013.01); *A61B 5/024* (2013.01); *A61B 5/0816* (2013.01); *A61B 5/14532* (2013.01); *A61B 5/684* (2013.01); *A61B 5/6825* (2013.01); *A61B 2560/0214* (2013.01); *A61B 2560/0252* (2013.01); *A61B 2562/029* (2013.01); *A61B 2562/0247* (2013.01); *A61B 2562/046* (2013.01); *G05B 2219/32128* (2013.01); *G05B 2219/33192* (2013.01); *G05B 2219/40568* (2013.01); *G05B 2219/45243* (2013.01); *H04M 2250/12* (2013.01); *H04W 84/18* (2013.01)

(58) Field of Classification Search
CPC ..... A43B 13/18; A43B 13/186; A43B 13/189; A43B 13/203; A43B 13/38; A43B 17/026; A43B 1/00; A43B 3/00; A43B 13/20; A61B 5/0022; A61B 5/0265; A61B 5/1036; A61B 5/1038; A61B 5/11; A61B 5/1112; A61B 5/1118; A61B 5/112; A61B 5/1123; A61B 5/6803; A61B 5/6805; A61B 5/6806; A61B 5/6807; A61B 5/6817; A61B 5/6831; A61B 5/686; A61B 5/6878; A61B 5/6891; A61B 5/6895; A61B 5/6898; A61B 5/743; A61B 5/01; A61B 5/021; A61B 5/024; A61B 5/0816; A61B 5/14532; A61B 5/6825; A61B 5/684; A61B 2560/0214; A61B 2560/0252; A61B 2562/0247; A61B 2562/029; A61B 2562/046; A61F 5/14; G05B 19/042; G05B 19/048; G05B 19/406; G05B 2219/32128; G05B 2219/33192; G05B 2219/40568; G05B 2219/45243; G08C 17/02; H04L 67/125; H04M 1/72403; H04M 1/72412; H04M 2250/12; H04W 4/00; H04W 4/70; H04W 12/084; H04W 24/04; H04W 84/18; H04W 12/33

USPC .......................................... 340/870.07; 36/29

See application file for complete search history.

(56)     References Cited

U.S. PATENT DOCUMENTS

| | | | |
|---|---|---|---|
| 4,021,860 A | 5/1977 | Swallow et al. | |
| 4,649,552 A | 3/1987 | Yukawa | |
| 4,651,354 A | 3/1987 | Petrey | |
| 4,989,349 A | 2/1991 | Ellis, III | |
| 5,317,819 A | 6/1994 | Ellis, III | |
| 5,544,429 A | 8/1996 | Ellis, III | |
| 5,617,585 A | 4/1997 | Fons et al. | |
| 5,813,142 A * | 9/1998 | Demon | A43B 13/203 600/592 |
| 5,909,948 A | 6/1999 | Ellis, III | |
| 6,115,941 A | 9/2000 | Ellis, III | |
| 6,115,945 A | 9/2000 | Ellis, III | |
| 6,138,281 A | 10/2000 | Chiaruttini | |
| 6,163,982 A | 12/2000 | Ellis, III | |
| 6,178,667 B1 | 1/2001 | Kaneko et al. | |
| 6,295,744 B1 | 10/2001 | Ellis, III | |
| 6,308,439 B1 | 10/2001 | Ellis, III | |
| 6,360,453 B1 | 3/2002 | Ellis, III | |
| 6,487,795 B1 | 12/2002 | Ellis, III | |
| 6,584,706 B1 | 7/2003 | Ellis, III | |
| 6,591,519 B1 | 7/2003 | Ellis, III | |
| 6,609,312 B1 | 8/2003 | Ellis, III | |
| 6,629,376 B1 | 10/2003 | Ellis, III | |
| 6,662,470 B2 | 12/2003 | Ellis, III | |
| 6,675,498 B1 | 1/2004 | Ellis, III | |
| 6,675,499 B2 | 1/2004 | Ellis, III | |
| 6,708,424 B1 | 3/2004 | Ellis, III | |
| 6,729,046 B2 | 5/2004 | Ellis, III | |
| 6,748,674 B2 | 6/2004 | Ellis, III | |
| 6,763,616 B2 | 7/2004 | Ellis, III | |
| 6,782,641 B2 | 8/2004 | Turner et al. | |
| 6,789,331 B1 | 9/2004 | Ellis, III | |
| 6,810,606 B1 | 11/2004 | Ellis, III | |
| 6,877,254 B2 | 4/2005 | Ellis, III | |
| 6,918,197 B2 | 7/2005 | Ellis, III | |
| 7,010,869 B1 | 3/2006 | Ellis, III | |
| 7,082,697 B2 | 8/2006 | Ellis, III | |
| 7,093,379 B2 | 8/2006 | Ellis, III | |
| 7,107,626 B1 | 9/2006 | Andrews | |
| 7,119,510 B2 | 10/2006 | Kawai | |
| 7,127,834 B2 | 10/2006 | Ellis, III | |
| 7,168,185 B2 | 1/2007 | Ellis, III | |
| 7,174,658 B2 | 2/2007 | Ellis, III | |
| 7,191,644 B2 | 3/2007 | Haselhurst et al. | |
| 7,334,350 B2 | 2/2008 | Ellis, III | |
| 7,346,935 B1 | 3/2008 | Patterson | |
| 7,562,468 B2 | 7/2009 | Ellis | |
| 7,647,710 B2 | 1/2010 | Ellis, III | |
| 7,676,960 B2 | 3/2010 | DiBenedetto et al. | |
| 7,713,173 B2 | 5/2010 | Shin et al. | |
| 7,748,240 B1 | 7/2010 | Cherneski | |
| 7,788,827 B2 | 9/2010 | Fogg et al. | |
| 7,793,430 B2 | 9/2010 | Ellis | |
| 7,822,391 B1 | 10/2010 | Delker et al. | |
| 8,209,882 B2 | 7/2012 | Eimer et al. | |
| 8,220,077 B1 * | 7/2012 | Ott | A41B 11/008 2/409 |
| 8,291,614 B2 | 10/2012 | Ellis | |
| 8,656,607 B2 | 2/2014 | Ellis | |
| 9,030,335 B2 | 5/2015 | Ellis | |
| 9,063,529 B2 | 6/2015 | Ellis | |
| 9,100,495 B2 | 8/2015 | Ellis | |
| 9,160,836 B2 | 10/2015 | Ellis | |
| 9,207,660 B2 | 12/2015 | Ellis | |
| 9,375,047 B2 | 6/2016 | Ellis | |
| 9,398,787 B2 | 7/2016 | Ellis, III | |
| 9,504,291 B2 | 11/2016 | Ellis | |
| 9,709,971 B2 | 7/2017 | Ellis | |
| 9,877,523 B2 | 1/2018 | Ellis | |
| 2002/0000051 A1 | 1/2002 | Ellis | |
| 2002/0007571 A1 | 1/2002 | Ellis | |
| 2002/0007572 A1 | 1/2002 | Ellis | |
| 2002/0014020 A1 | 2/2002 | Ellis | |
| 2002/0014021 A1 | 2/2002 | Ellis | |
| 2002/0017036 A1 | 2/2002 | Berger et al. | |
| 2002/0023373 A1 | 2/2002 | Ellis | |
| 2002/0073578 A1 | 6/2002 | Ellis | |
| 2002/0116841 A1 | 8/2002 | Ellis | |
| 2003/0009308 A1 * | 1/2003 | Kirtley | A43B 3/44 702/141 |
| 2003/0046830 A1 | 3/2003 | Ellis | |
| 2003/0070320 A1 | 4/2003 | Ellis | |
| 2003/0079375 A1 | 5/2003 | Ellis | |
| 2003/0089136 A1 | 5/2003 | Lynch et al. | |
| 2003/0097771 A1 | 5/2003 | Tuttle | |
| 2003/0131497 A1 | 7/2003 | Ellis | |
| 2003/0208926 A1 | 11/2003 | Ellis | |
| 2003/0213269 A1 | 11/2003 | Peeler et al. | |
| 2003/0217482 A1 | 11/2003 | Ellis | |
| 2004/0025375 A1 | 2/2004 | Turner et al. | |
| 2004/0134096 A1 | 7/2004 | Ellis | |
| 2004/0221371 A1 | 11/2004 | Kato | |
| 2004/0250447 A1 | 12/2004 | Ellis | |
| 2005/0016020 A1 | 1/2005 | Ellis | |
| 2005/0086837 A1 | 4/2005 | Ellis | |
| 2005/0091729 A1 | 5/2005 | Alley | |
| 2005/0132607 A1 | 6/2005 | Dojan et al. | |
| 2005/0144703 A1 | 7/2005 | Hilbert | |
| 2005/0217142 A1 | 10/2005 | Ellis | |
| 2005/0217143 A1 | 10/2005 | Ellis | |
| 2005/0217150 A1 | 10/2005 | Hoffer et al. | |
| 2006/0032086 A1 | 2/2006 | Ellis, III | |
| 2006/0248749 A1 | 11/2006 | Ellis | |
| 2007/0006489 A1 * | 1/2007 | Case, Jr. | A43D 1/027 36/132 |
| 2007/0123391 A1 | 5/2007 | Shin et al. | |
| 2007/0163147 A1 * | 7/2007 | Cavanagh | A61B 5/6807 36/44 |
| 2007/0156066 A1 | 8/2007 | Hann | |
| 2007/0180736 A1 | 8/2007 | DiBenedetto et al. | |
| 2007/0199211 A1 | 8/2007 | Campbell | |
| 2008/0086916 A1 | 4/2008 | Ellis | |
| 2009/0107009 A1 | 4/2009 | Bishop et al. | |
| 2009/0183387 A1 | 7/2009 | Ellis | |
| 2009/0200661 A1 | 8/2009 | Ellis | |
| 2010/0000345 A1 | 1/2010 | Udono | |
| 2010/0083539 A1 | 4/2010 | Norton | |
| 2010/0197157 A1 | 8/2010 | Wang | |
| 2010/0299965 A1 | 12/2010 | Avar et al. | |
| 2011/0003601 A1 | 1/2011 | Coutts et al. | |
| 2011/0056093 A1 | 3/2011 | Ellis, III | |
| 2011/0056097 A1 | 3/2011 | Ellis, III | |
| 2011/0061148 A1 | 3/2011 | Egozi | |
| 2011/0090888 A1 | 4/2011 | Arms et al. | |

(56) References Cited

U.S. PATENT DOCUMENTS

| | | | |
|---|---|---|---|
| 2011/0153261 | A1 | 6/2011 | Jang et al. |
| 2011/0305357 | A1 | 12/2011 | Wells |
| 2012/0019398 | A1 | 1/2012 | Vogt et al. |
| 2012/0054137 | A1 | 3/2012 | Alush |
| 2012/0058316 | A1 | 3/2012 | Cherneski |
| 2012/0186101 | A1* | 7/2012 | Sanchez ............... A43B 11/00 36/43 |
| 2012/0265434 | A1 | 10/2012 | Woodard et al. |
| 2013/0047461 | A1 | 2/2013 | Tzeng |
| 2013/0190903 | A1 | 7/2013 | Balakrishnan et al. |
| 2013/0312292 | A1 | 11/2013 | Yudelowitz |
| 2014/0215853 | A1 | 8/2014 | Rushbrook et al. |
| 2015/0257479 | A1 | 9/2015 | Ellis |
| 2022/0338581 | A1* | 10/2022 | Hopkins ............... A61B 5/1114 |

FOREIGN PATENT DOCUMENTS

| | | | |
|---|---|---|---|
| KR | 1020110071727 | A | 6/2011 |
| WO | WO2007126510 | A2 | 11/2007 |
| WO | WO2007126518 | A1 | 11/2007 |

OTHER PUBLICATIONS

Salpavaara, T., et al., "Wireless Insole Sensor System for Plantar Force Measurements During Sport Events," XIX IMEKO World Congress, Fundamental and Applied Metrology, Sep. 6-11, 2009, Lisbon, Portugal, pp. 2118-2123.

Ran, L. Y. "Development of Instrumented Insole Using Force Sensing Resistors," Faculty of Engineering and Science, Universiti Tanku Abdul Rahman, Apr. 2011, pp. i-319.

Murphy, N., et al., "Foot Pressure Measurement in a Clinical Setting," Tekscan, Inc. 2012, Retrieved from www.tekscan.com/medical., pp. 1-17.

Chumanov, E.S., et al., "Tracking the position of insole pressure sensors during walking and running". In: Proceedings from the 30th annual meeting of the american society of biomechanics, Stanford University, CA, 2007, pp. 1-2.

Carr, K., et al., "Biomechanics Gait Analysis Lab: Final Report," UCONN Biomedical Engineering, Team 3, 2006, pp. -140.

"The Pedar System," Retrieved on Apr. 11, 2013 from http://novel.de/novelcontent/pedar, pp. 1-2.

Petei, D.L., et al., "Time dependent behaviour of a force-sensitive resistor plantar pressure measurement insole." Proc Instn Mech Engrs 1996, vol. 210, No. 2, pp. 121-125.

International Search Report and Written Opinion; dated Jul. 30, 2013 for corresponding PCT Application No. PCT/US2013/037045.

Complete file history for U.S. Appl. No. 13/859,859.

Complete file history for U.S. Appl. No. 14/605,192.

Complete file history for U.S. Appl. No. 14/605,177.

Complete file history for U.S. Appl. No. 14/615,749.

Partial file history for U.S. Appl. No. 13/859,859, filed Mar. 4, 2015 to Apr. 22, 2015.

Partial file history for U.S. Appl. No. 14/605,192, filed Sep. 4, 2015 to present.

Partial file history for U.S. Appl. No. 14/605,177, filed Sep. 2, 2015 to present.

Partial file history for U.S. Appl. No. 14/615,749, filed Jul. 29, 2015 to present.

European Search Report; dated Dec. 14, 2015 for EP Application No. 13778247.0.

Complete file history for U.S. Appl. No. 15/164,650.

Non-Final Office Action; dated Apr. 14, 2017 for U.S. Appl. No. 15/358,533.

Notice of Allowance; dated Aug. 28, 2017 for U.S. Appl. No. 15/358,533.

Non-Final Office Action; dated Feb. 15, 2018 for U.S. Appl. No. 15/825,961.

Notice of Allowance; dated Oct. 31, 2018 for U.S. Appl. No. 15/995,166.

Non-Final Rejection for U.S. Appl. No. 16/008,082; dated Aug. 27, 2020 (26 pages).

Non-Final Office Action for U.S. Appl. No. 16/008,082; dated Oct. 6, 2021 (25 pages).

Non-Final Office Action for U.S. Appl. No. 16/993,474; dated May 4, 2022 (30 pages).

* cited by examiner

HORIZONTAL VIEW

ANTERIOR

HORIZONTAL CROSS SECTION

FRONTAL PLANE
CROSS SECTION

HORIZONTAL VIEW FROM BOTTOM UPWARD

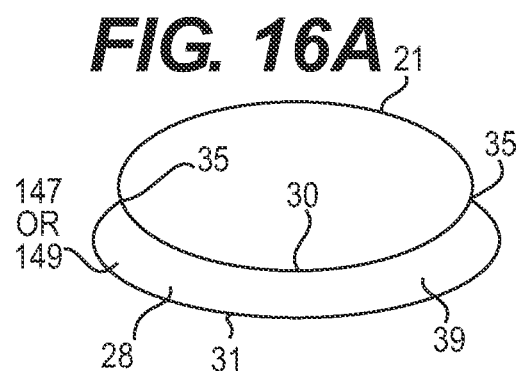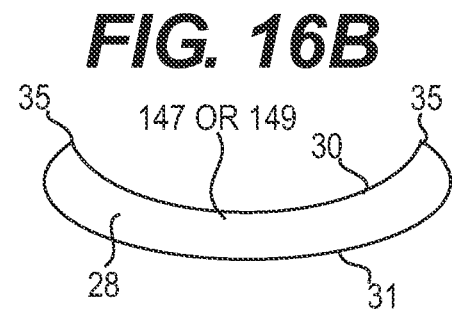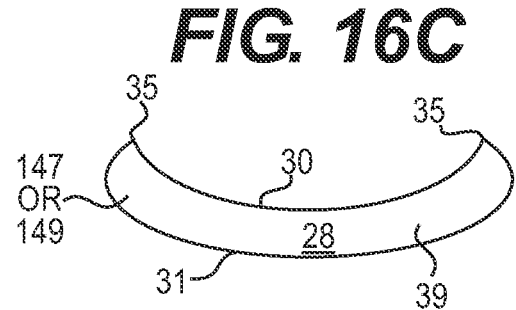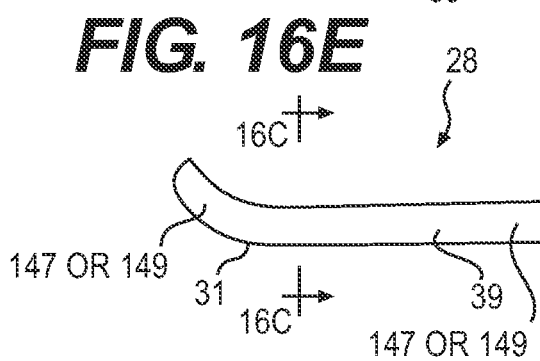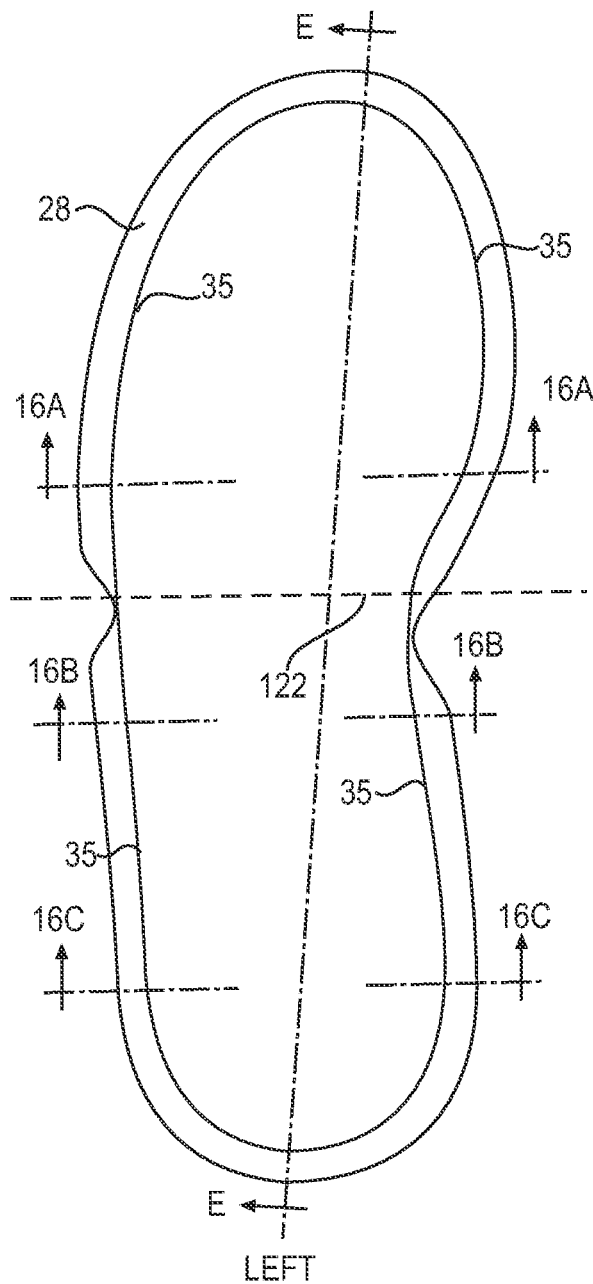

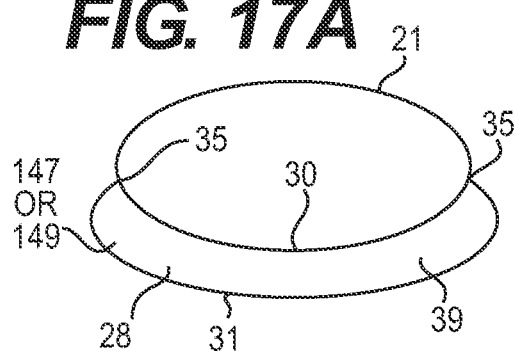
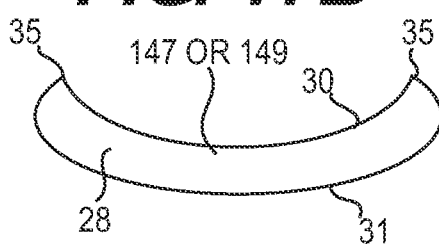
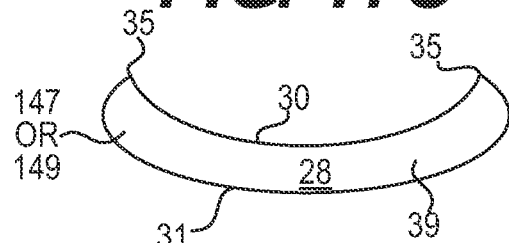
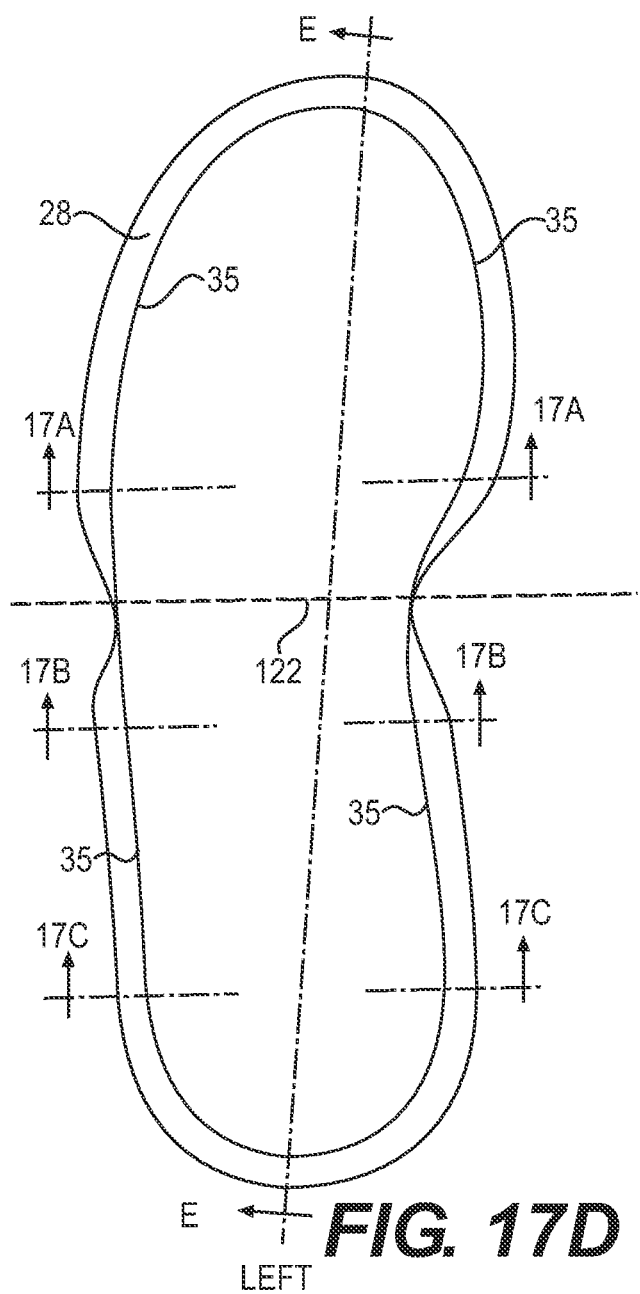
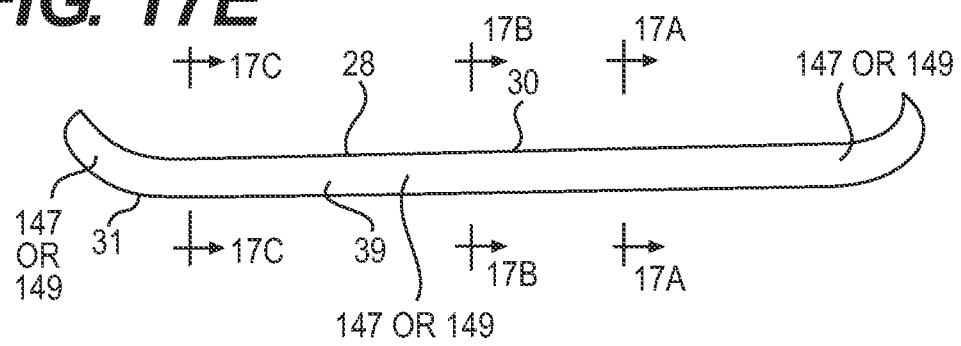

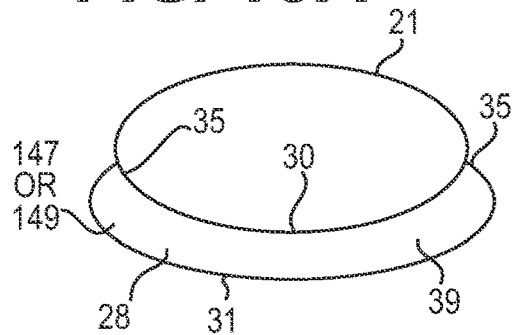
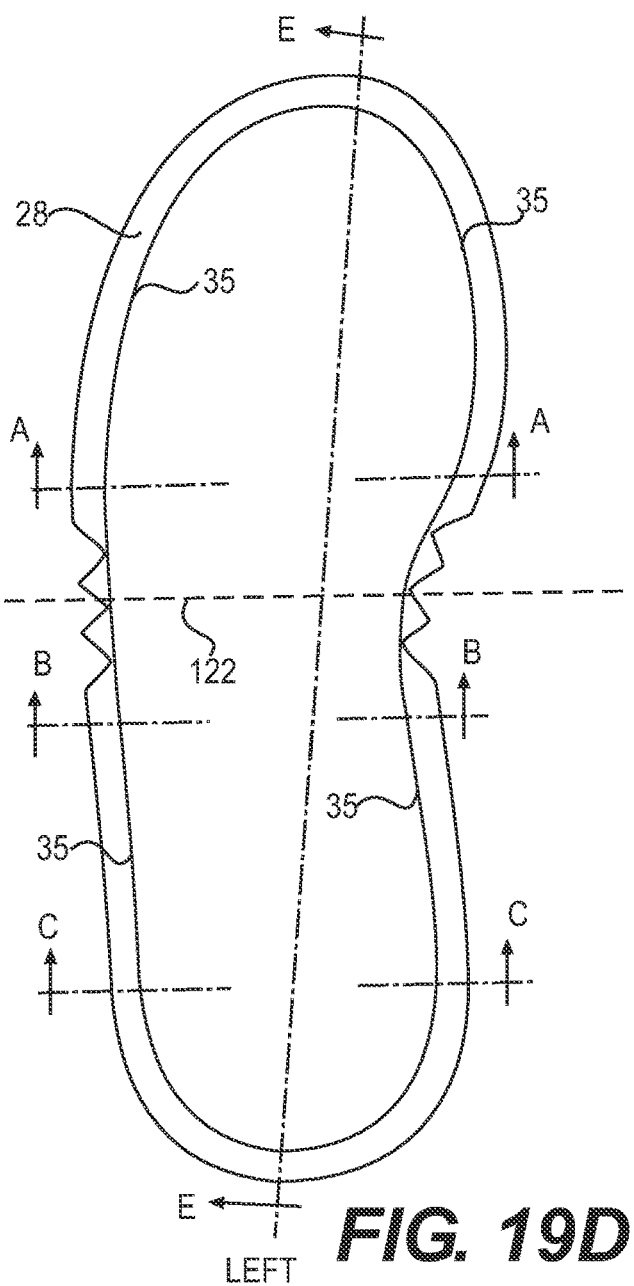
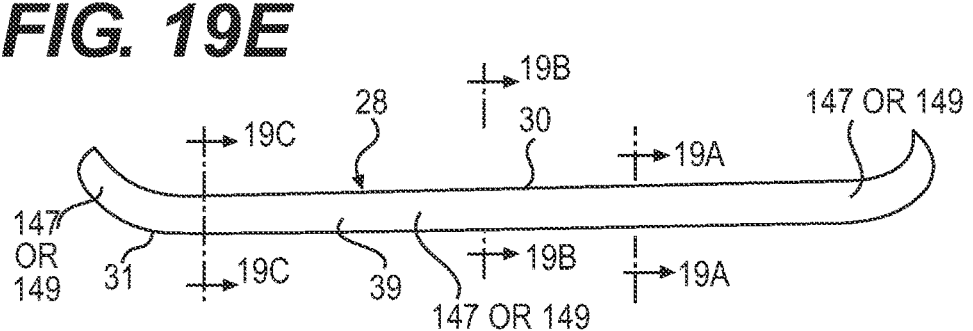

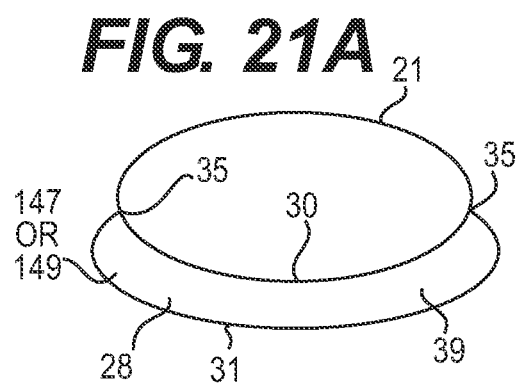
FIG. 21A
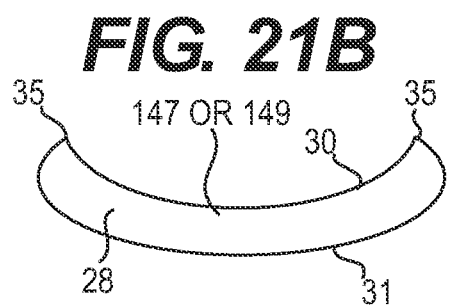
FIG. 21B
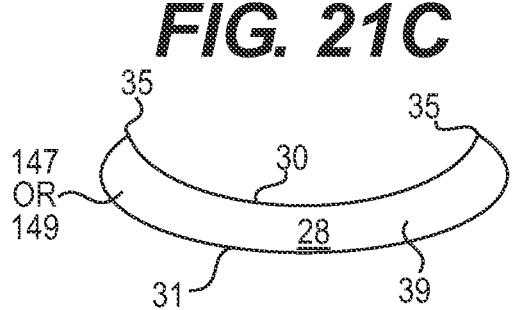
FIG. 21C
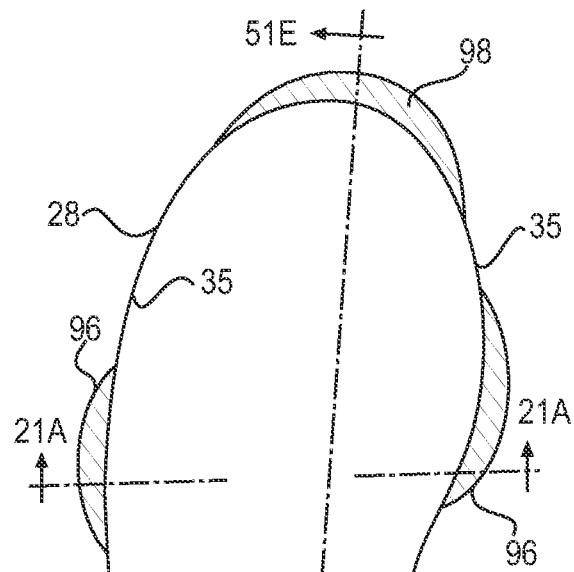
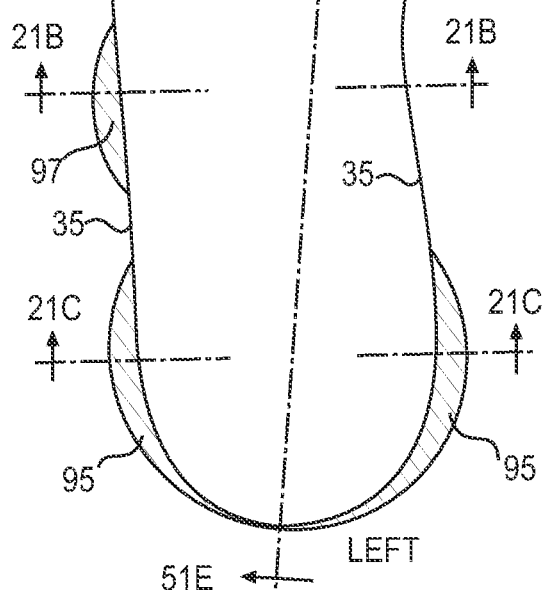
FIG. 21D
FIG. 21E
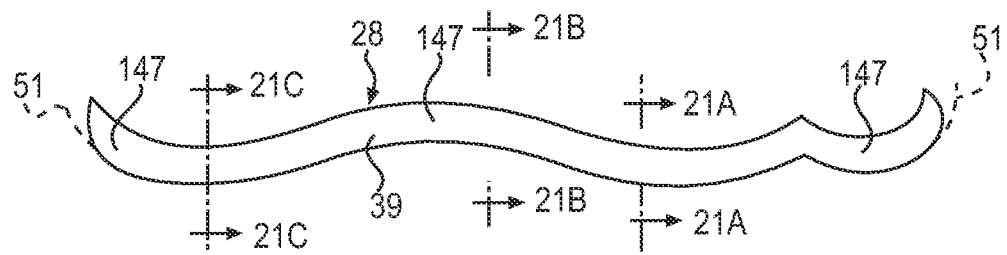

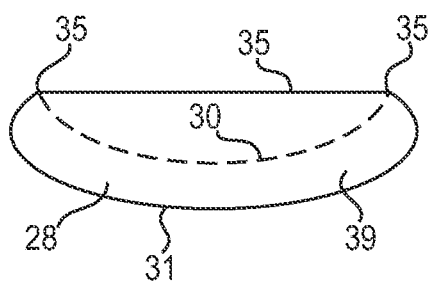
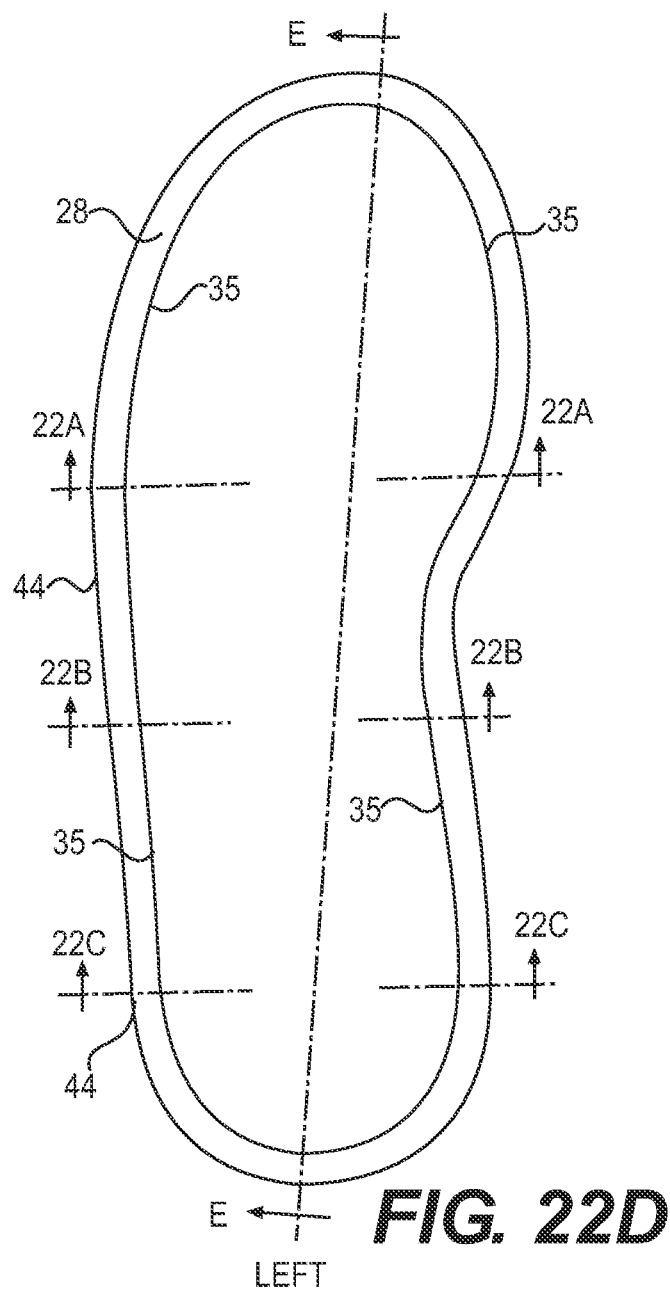
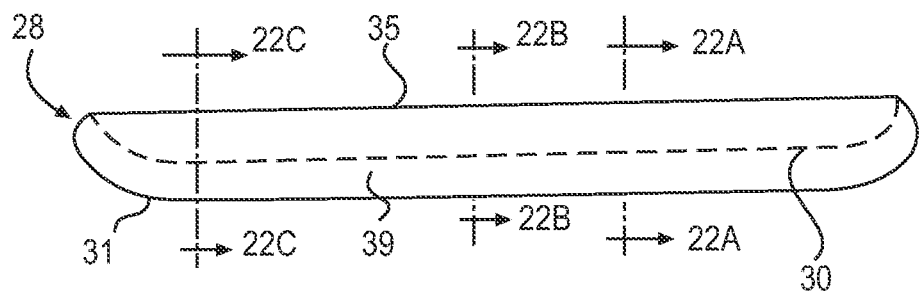

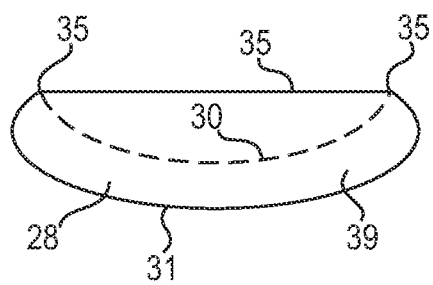
FIG. 23A FRONT VIEW
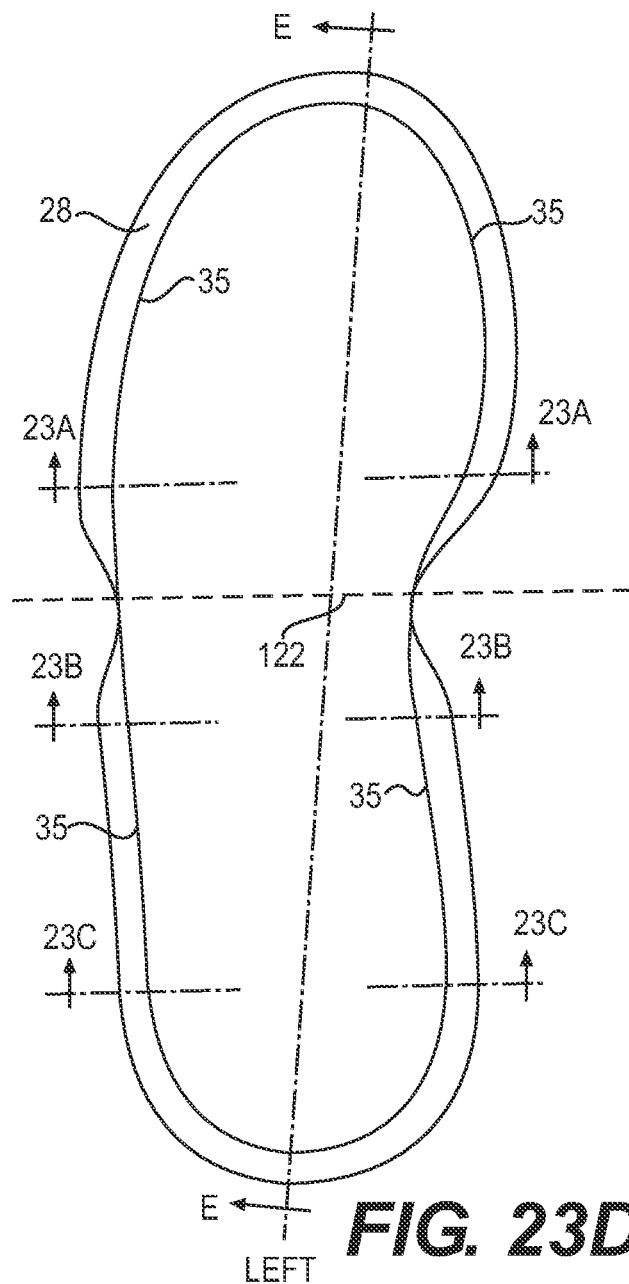
FIG. 23B BACK VIEW
FIG. 23D
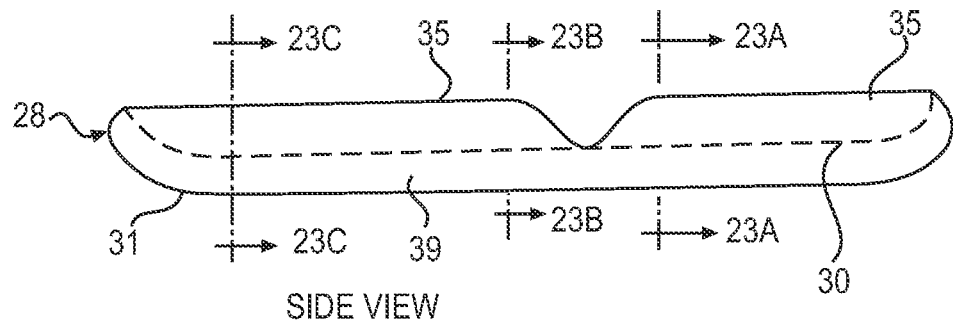
FIG. 23C SIDE VIEW

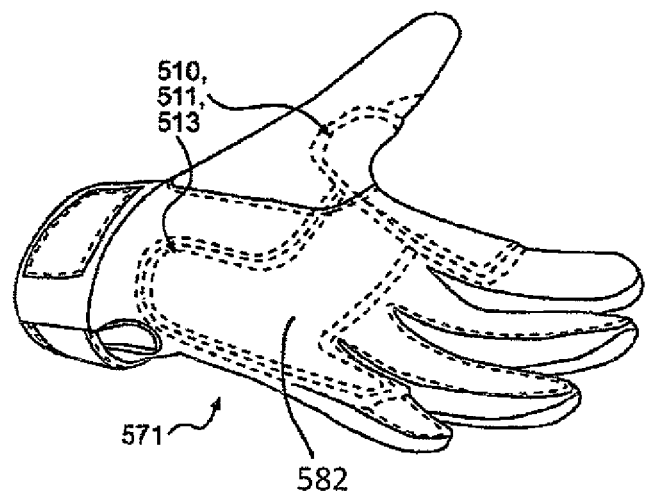
FIG. 27A
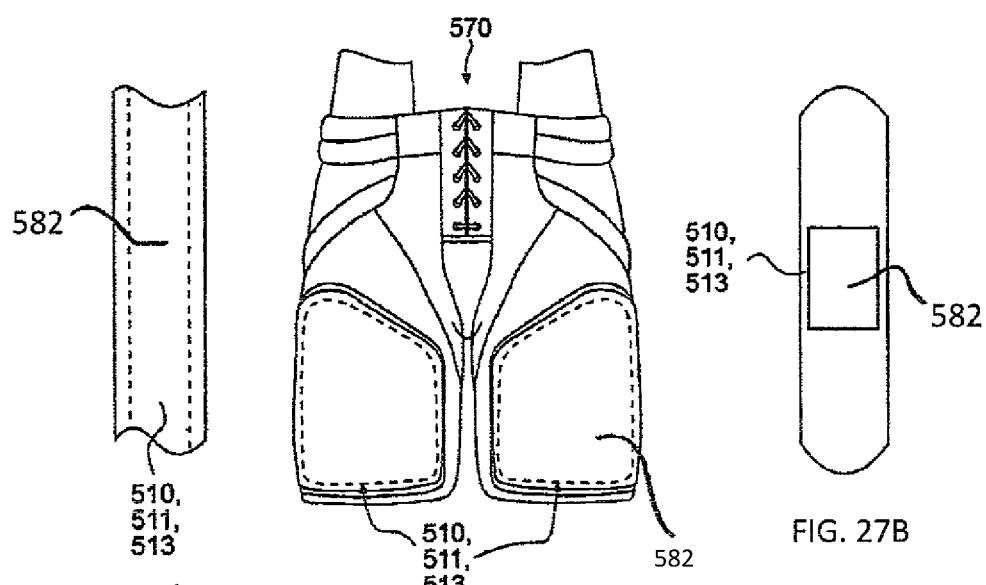
FIG. 27C
FIG. 27D
FIG. 27B

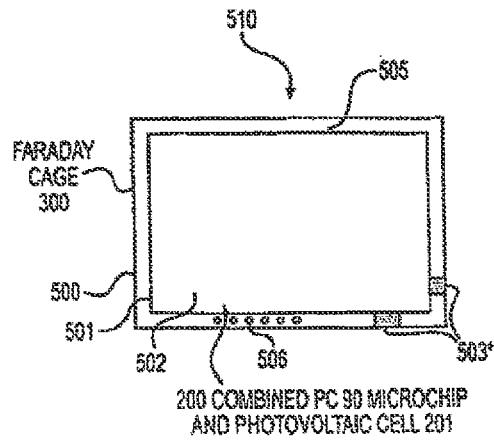
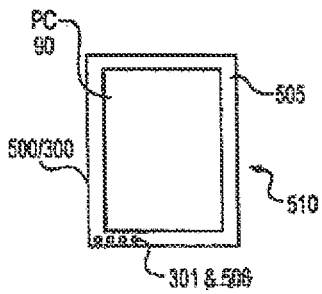
FIG. 33A
PRIOR ART
FIG. 33D
PRIOR ART
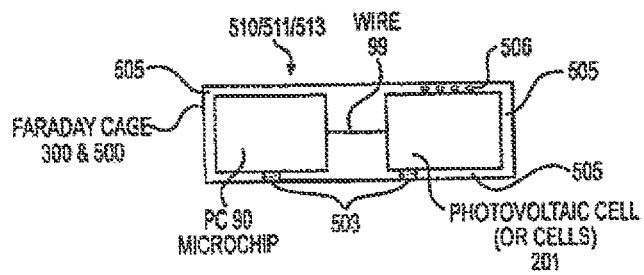
FIG. 33B
PRIOR ART
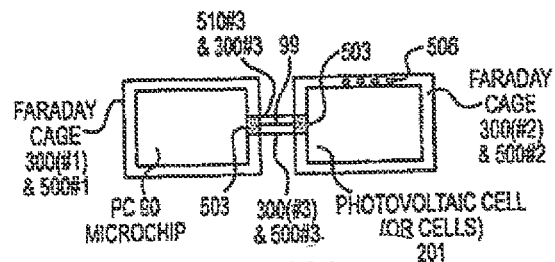
FIG. 33C
PRIOR ART
*CAN INCLUDE EXTERNAL CONNECTION FROM MICROCHIP/CELL 200

BIG DATA ARTIFICIAL INTELLIGENCE COMPUTER SYSTEM USED FOR MEDICAL CARE CONNECTED TO MILLIONS OF SENSOR-EQUIPPED SMARTPHONES CONNECTED TO THEIR USERS' CONFIGURABLE FOOTWEAR SOLES WITH SENSORS AND TO BODY SENSORS

This application is a continuation of U.S. patent application Ser. No. 17/402,004, filed on Aug. 13, 2021, which, in turn, is a continuation of Ser. No. 16/749,665, filed on Jan. 22, 2020, now U.S. Pat. No. 11,120,909, issued on Sep. 14, 2021, which, in turn is a continuation of U.S. patent application Ser. No. 16/263,181, filed on Jan. 31, 2019, now U.S. Pat. No. 10,568,369, issued on Feb. 25, 2020, which, in turn, is a continuation of U.S. patent application Ser. No. 15/995,166, filed on Jun. 1, 2018, now U.S. Pat. No. 10,226,082, issued on Mar. 12, 2019, which claims the benefit of U.S. Provisional applications: No. 62/603,494, filed Jun. 2, 2017; No. 62/603,930, filed Jun. 16, 2017; No. 62/605,028, filed Jul. 31, 2017; No. 62/606,281, filed Sep. 18, 2017; No. 62/708,334, filed Dec. 6, 2017; No. 62/709,431, filed Jan. 19, 2018; No. 62/762,671, filed May 14, 2018; and U.S. patent application Ser. No. 15/995,166 is a continuation-in-part of U.S. patent application Ser. No. 15/825,967, filed on Nov. 29, 2017, now U.S. Pat. No. 10,172,396 issued on Jan. 8, 2019, which is a continuation of U.S. patent application Ser. No. 15/358,533 filed on Nov. 22, 2016, now U.S. Pat. No. 9,877,523, issued Jan. 30, 2018, which is a continuation-in-part of U.S. patent application Ser. No. 15/298,441, filed Oct. 20, 2016, which is a continuation of U.S. patent application Ser. No. 15/164,650, filed May 25, 2016, now U.S. Pat. No. 9,504,291, issued Nov. 29, 2016, which is a continuation of U.S. patent application Ser. No. 14/922,408, filed Oct. 26, 2015, now U.S. Pat. No. 9,375,047, issued Jun. 28, 2016, which is a continuation of U.S. patent application Ser. No. 14/722,547, filed May 27, 2015, now U.S. Pat. No. 9,207,660, issued Dec. 8, 2015, which is a continuation of U.S. patent application Ser. No. 14/615,749, filed Feb. 6, 2015, now U.S. Pat. No. 9,100,495, issued Aug. 4, 2015, which is a continuation of U.S. patent application Ser. Nos. 14/605,177 and 14/605,192, both filed Jan. 26, 2015, now U.S. Pat. No. 9,160,836, issued Oct. 13, 2015 and U.S. Pat. No. 9,063,529, issued Jun. 23, 2015, respectively, and U.S. patent application Ser. Nos. 14/605,177 and 14/605,192, both filed Jan. 26, 2015, are continuations of U.S. patent application Ser. No. 13/859,859, filed Apr. 10, 2013, now U.S. Pat. No. 9,030,335, issued May 12, 2015, which claims the benefit of the following U.S. Provisional applications: No. 61/687,072, filed on Apr. 18, 2012; No. 61/687,127, filed Apr. 19, 2012; No. 61/851,598, filed Mar. 11, 2013; No. 61/851,869, filed Mar. 14, 2013; and No. 61/852,038, filed Mar. 15, 2013. U.S. patent application Ser. No. 15/358,533 also claims the benefit of U.S. Provisional applications: No. 62/496,258, filed Oct. 12, 2016; No. 62/495,121, filed Sep. 2, 2016; No. 62/392,654, filed Jun. 8, 2016; No. 62/392,024, filed May 18, 2016; No. 62/391,837, filed May 13, 2016; No. 62/391,838, filed May 13, 2016; No. 62/386,987, filed Dec. 18, 2015; No. 62/386,921, filed Dec. 16, 2015; and No. 62/386,337, filed Nov. 27, 2015; the disclosures of all of which U.S. patent applications and U.S. provisional applications are hereby incorporated by reference in their entirety.

BACKGROUND

In many prior U.S. patents, including for example both the '819 and '982 patents, the applicant has shown in detail the inherent stability defects in most modern footwear, which are structurally flat instead of wrapping around the anatomically rounded shape of an intended wearer's foot sole, as required in order to preserve the naturally superior biomechanical stability of the intended wearer's bare foot sole.

However, there is also high degree of complexity inherent in correctly designing and manufacturing anatomically neutral footwear due to the extremely complex structure of the human foot. The result is that nearly all commercially available footwear available currently significantly degrade the natural stability of the barefoot, resulting in needless chronic and acute injuries.

But the alternative of bare feet alone is not the answer, since bare feet are often unsuited for the modern environment, since they fail to provide insulation against extreme heat or cold, protection against sharp objects or dangerous chemicals, and traction on artificial sports or other surfaces.

With no practical alternatives, a wearer of modern footwear is forced into a lifetime of defective footwear use that all too frequently results in anatomical structure and gait problems that cause severe chronic injury to joints and other health issues. Unfortunately, with existing technology, only the symptoms of the injury are ever treated, because there is currently no way to easily evaluate and identify the underlying specific footwear causes of the injury or to eliminate those causes or reduce their severity.

Nor is there a way to provide immediate and effective testing and evaluation to find the most optimal footwear solution as quickly as possible. Nor is there a way then to immediately implement that most optimal footwear solution, while afterwards continuing indefinitely the ongoing testing and evaluation to prevent future problems. Nor is there A way to share these individual optimal solutions among larger population groups to achieve potentially many other tangible health benefits among similar subgroups.

SUMMARY

The applicant's new footwear sole inventions emphasize an extraordinarily simple approach, which is simply bending the sides of footwear sole up in the direction of the foot, instead of leaving the sole structure conventionally flat. The result is a new footwear sole that is simply concavely rounded underneath the intended wearer's foot sole, particularly as viewed in frontal plane cross-sections.

The new footwear soles are not complex to design and manufacture, since they avoid dealing with the enormous complexity of trying to conform to the irregularly shaped human foot structure. They still, however, preserve most if not all of the essential biomechanical superiority of the barefoot in natural pronation and supination motion, even when shod with any of the variations of the new sole inventions described in this application—as long as the footwear sole's concave rounding is configured to deform under a body weight load to flatten against the flat ground, as does a barefoot sole.

The applicant's inventions also include using a smartphone device with motion sensors and/or in-shoe force and/or pressure sensors to easily evaluate and identify the underlying specific footwear causes of a footwear injury or to eliminate those causes or reduce their severity. The applicant's inventions also include footwear with bladders, compartments, chambers and/or sipes configured to be controlled by the smartphone in real time and can also include the concavely rounded sole structure invention described above and elsewhere in this application.

With the applicant's smartphone and configurable footwear, there a way to provide immediate and effective testing and evaluation to find the most optimal footwear solution as quickly as possible. In addition, with them there a way then to immediately implement that most optimal footwear solution, while afterwards continuing indefinitely the ongoing testing and evaluation to prevent future problems. Furthermore, with them there as way to share these individual optimal solutions among larger population groups to achieve potentially many other tangible health benefits among similar subgroups.

BRIEF DESCRIPTION OF THE DRAWINGS

FIG. 10A-10D are FIGS. 15, 16, and 17A-17B of the applicant's '916 publication and show footwear prior art computer controlled inner bladders, compartments, or chambers surrounded by internal flexibility sipes and outer bladders, compartments, or chambers. FIGS. 10E-10H show prior art examples FIGS. 1, 2, 4A and 4B from Demon's U.S. Pat. No. 5,813,142 of computer controlled valves venting from bladders to outside the shoe sole. FIG. 10I is FIG. 44 of the same publication and shows a footwear prior art computer controlled mechanical cushioning system.

FIG. 11A shows a horizontal view of the upper surface of a footwear sole with an intended wearer's footprint superimposed in its normal position with the semi-thong 3 located between the big and second toes; and optional other semi-thong locations indicated between the other toes. FIGS. 11B-11E show horizontal cross-sections of the semi-thong; FIG. 11F shows a frontal plane cross-section showing the location of an example semi-thong. FIGS. 11G-11I show examples of different semi-thong structures in cross-section.

FIG. 14A is prior art FIG. 62 from the applicant's '350 U.S. patent showing the extra sole width required to accommodate the dynamic footprint and FIGS. 14B-14D are prior art FIGS. 1A-1C from the applicant's '982 U.S. patent showing the footwear sole's capability to deform to flatten under the body weight of a wearer, including during 20 degrees of supination or pronation. FIG. 14E is the prior art FIG. 28c of the applicant's '819 U.S. patent showing the flexibility axis 122.

FIGS. 15E-15H show different potential variations that can be incorporated into the long axis structure shown in FIGS. 15A-15D.

FIG. 16A-16E is like FIG. 15A-E, but with a flexibility groove just aft of the forefoot of the footwear sole on both sides, between the cross-sections of FIGS. 16A and 16B.

FIGS. 17A-17E show variations of the flexibility groove located proximate to flexibility axis 122.

FIGS. 18A and 18B show with dashed line the position of the inset outersole 31 established by the groove, and FIG. 18C also shows a fabric cover over the groove, the fabric cover optionally forming a portion of a strap for the upper.

FIGS. 19A-19E show variations of the flexibility groove located proximate to flexibility axis 122.

FIG. 21A-21E is the applicant's concavely rounded footwear sole inventions applied to prior art FIGS. 13A-13E, which is an example embodiment with bulges and abbreviated sides for flexibility.

FIGS. 22A-22D are a front view, a back view, a side view, and an overhead view of the applicant's concavely rounded footwear sole shown in FIGS. 15A-15E, with inner dashed lines showing the inner surface 30 of the sole.

FIG. 23A-23D are a front view, a back view, a side view, and an overhead view of the applicant's concavely rounded footwear sole shown in FIGS. 17A-17E, with inner dashed lines showing the inner surface 30 of the sole.

FIGS. 27A-27D are examples of apparatus with sensors 582 based on FIGS. & 60A-60C of the applicant's '916 application.

FIGS. 33A-33D are examples of apparatus based on FIGS. 23A-C & G of the '661 application.

DETAILED DESCRIPTION OF EXAMPLE EMBODIMENTS

Figure 1A:
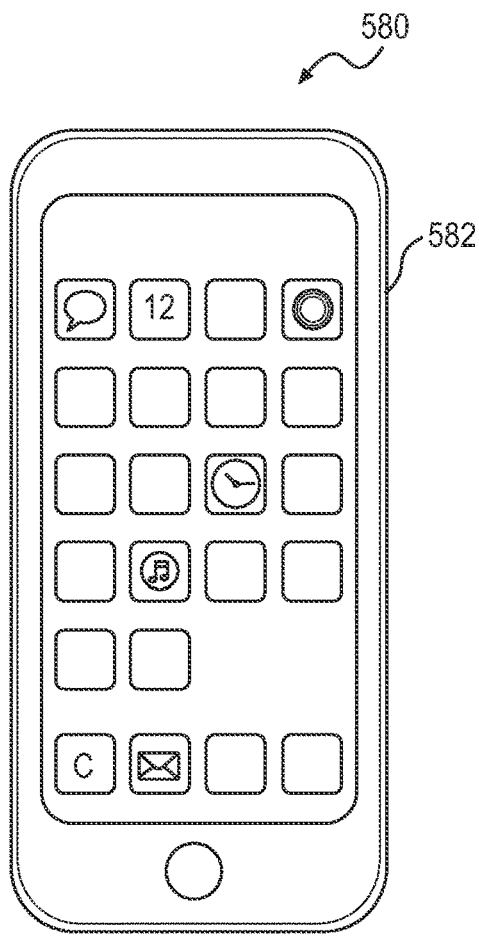
FIGS. 1A and 1B are examples of smartphones, the iPhone 5™ and the Samsung Galaxy S III™, respectively, which can be used to actively configure footwear and other apparatus.
Figure 1B:
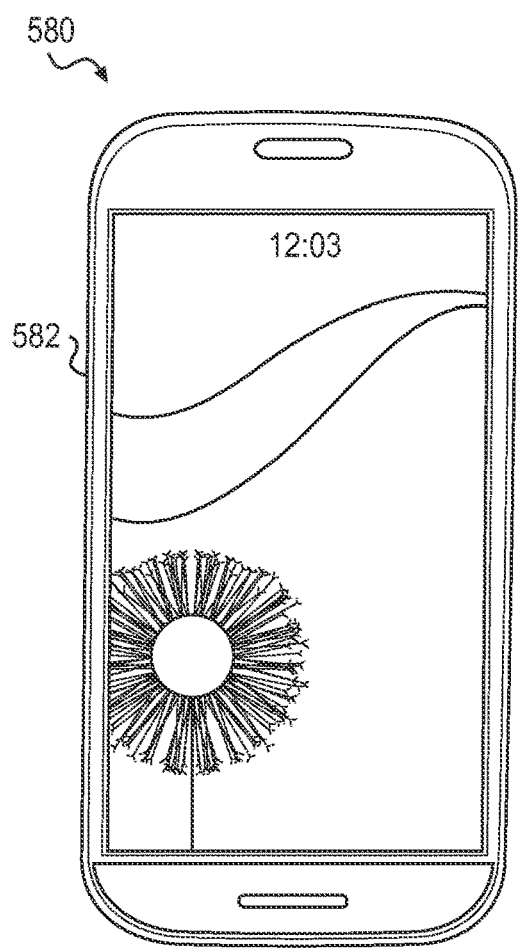

Among the inventions included in this application are the method, apparatus, and software of using a general or special purpose computer device 580, including a smartphone 580 such as an Apple iPhone 5™ and a Samsung Galaxy S III™, as shown in FIGS. 1A and 1B, as well as a Motorola Droid™, a Nokia Lumia™ and a BlackBerry™ 10, as other examples, to measure the relative motion of a body and/or a body part during the locomotion of a user of the smartphone (or any other portable or mobile microcomputer device, general purpose or specialized, including for example the Apple iPod™).

The smartphone device 580 can also be used to measure the force or relative pressure distribution of the wearer's foot sole in footwear; or to do both, including simultaneously, while also performing the other standard functions of a smartphone, like performing phone, email, browsing, and audio and/or video functions.

Smartphones can be configured with existing hardware motion sensing components, like a three-axis gyroscope and three-axis accelerometer in the iPhone 5™ and Samsung Galaxy S III™, for example, and/or additional and/or new hardware or software components to perform similar or other motion data measurement. The above smartphone or other microcomputing devices 580 can be mobile and/or wearable.

The smartphone or other devices 580 can also be configured to be capable of recording and/or streaming (in real time or later) wired or wirelessly any such measurement data to another computer, either local to the user (using a tablet, laptop or desktop, for example) or to a cloud array of computers such as the example of the Apple iCloud or to any other computer. The smartphone or other device 580 can be configured to process the measurement data itself and/or in conjunction with a local and/or remote server, including the examples of an Apple iPhone™ a MacBook Pro™ laptop computer and/or the Apple iCloud™.

Figure 2A:
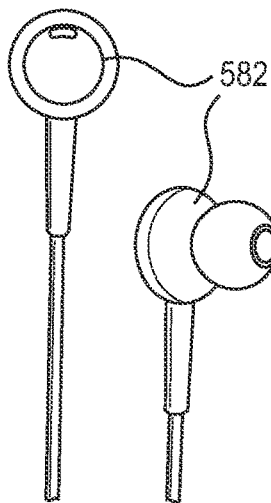
FIGS. 2A and 2B are example earphones and headphones, respectively, which can include motion, proximity, and other sensors 582.
Figure 2B:
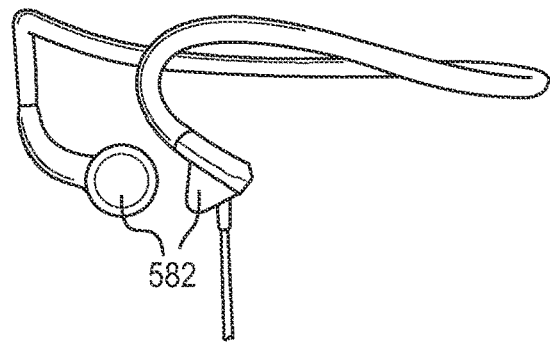

The smartphone or other device 580 can be configured to include the necessary sensor or sensors 582, in the device 580 itself and/or connected to it by wire or wirelessly, as well as associated electronic, software, and other components, to provide the capability to capture various kinds of motion and/or other data measurements; and/or the smartphone device can be used with one or more peripheral devices with sensors 582 and associated components, which can be located with or near the smartphone or located remotely from it, so that the motion of the body and/or one or more body parts of the user can be measured separately and/or simultaneously in whatever manner desired. For example, an iPhone 5™ with EarPods™ or other headphones, as shown in FIGS. 2A and 2B, that include motion sensors can be paired with an iPod™ with additional sensors and be connected to each other wirelessly or wired (even potentially in the future including the example of using a wearer's body as a conductive wire).

Figure 3:
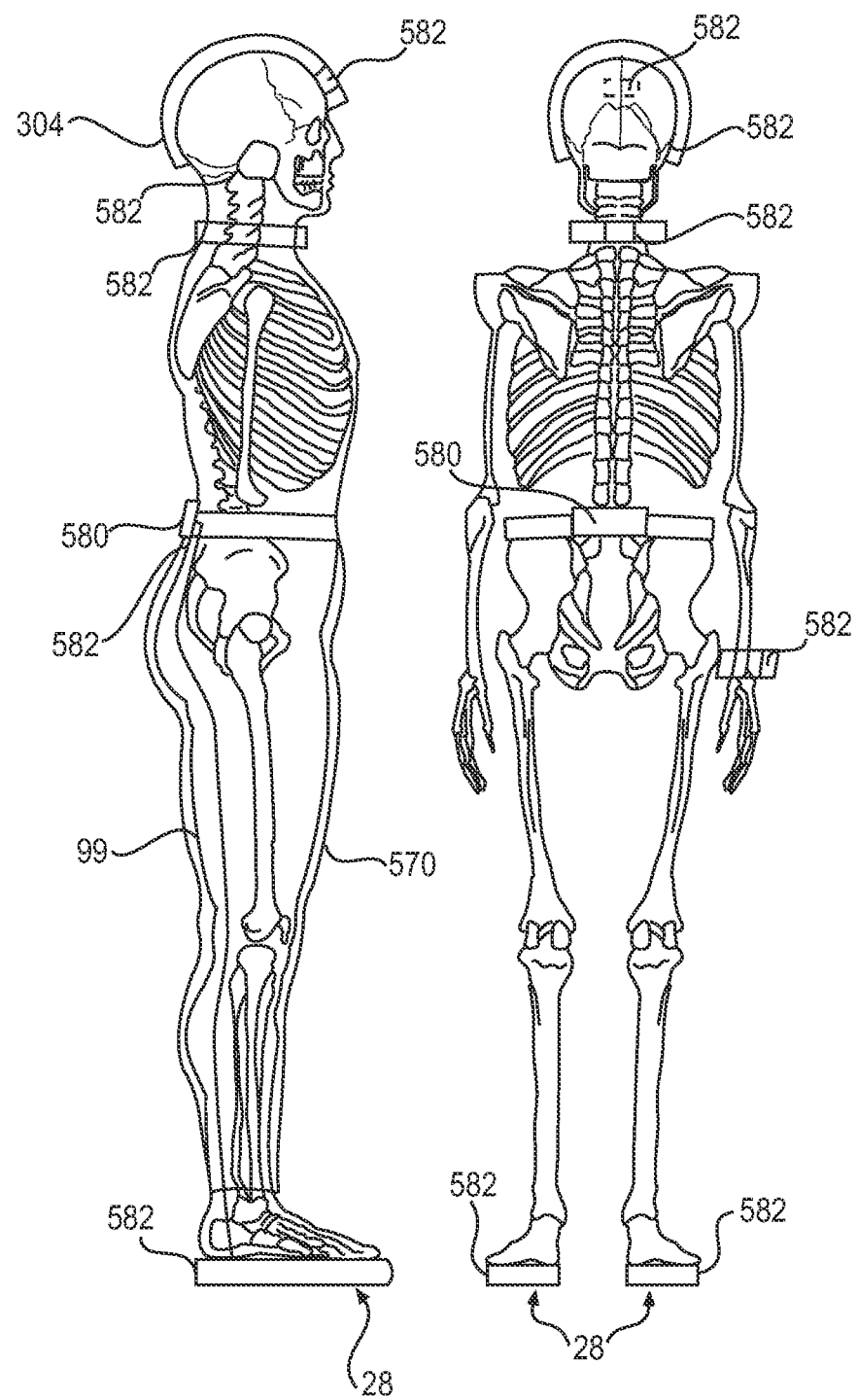
FIG. 3 shows side and back views of a human skeleton to illustrate the potential positions for the smartphone and for sensors on the body or apparel or equipment, including footwear, pants, belt, collar, wristband, earphones, and helmet.
Figure 4A:
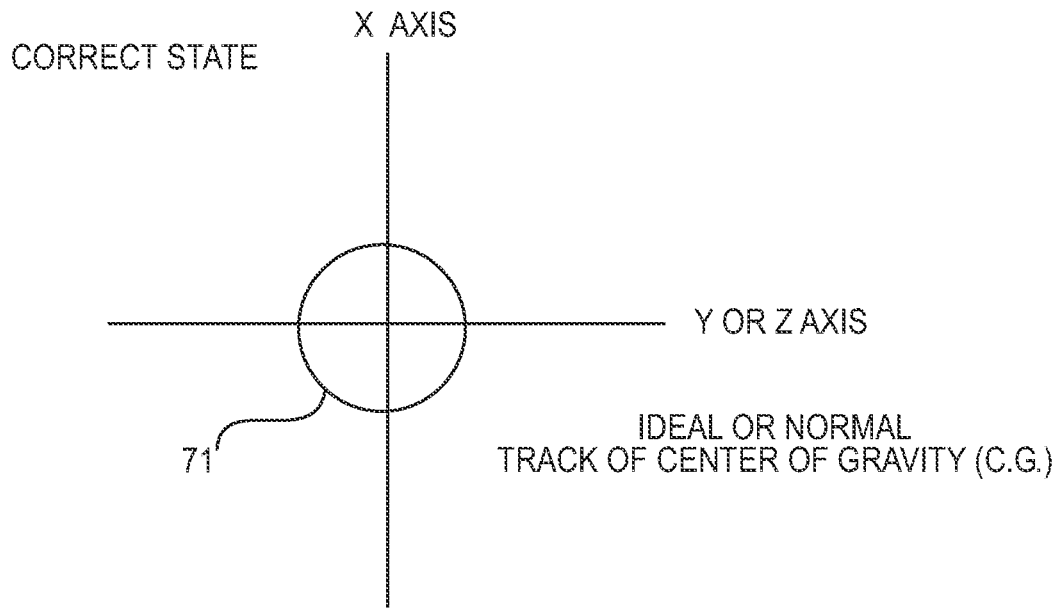
FIGS. 4A and 4B show two axis graphs showing examples of tracks of center of gravity (C.G.) motion over at least a full locomotion stride, FIG. 4A showing a model or correct or preferred state and FIG. 4B showing uncorrected or misaligned state.
Figure 4B:
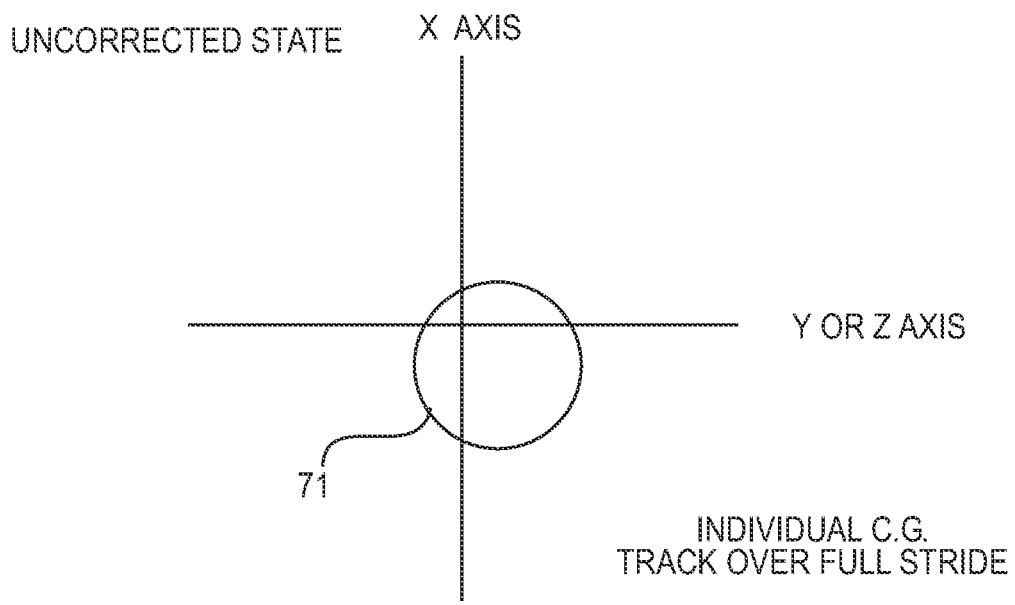
Figure 5:
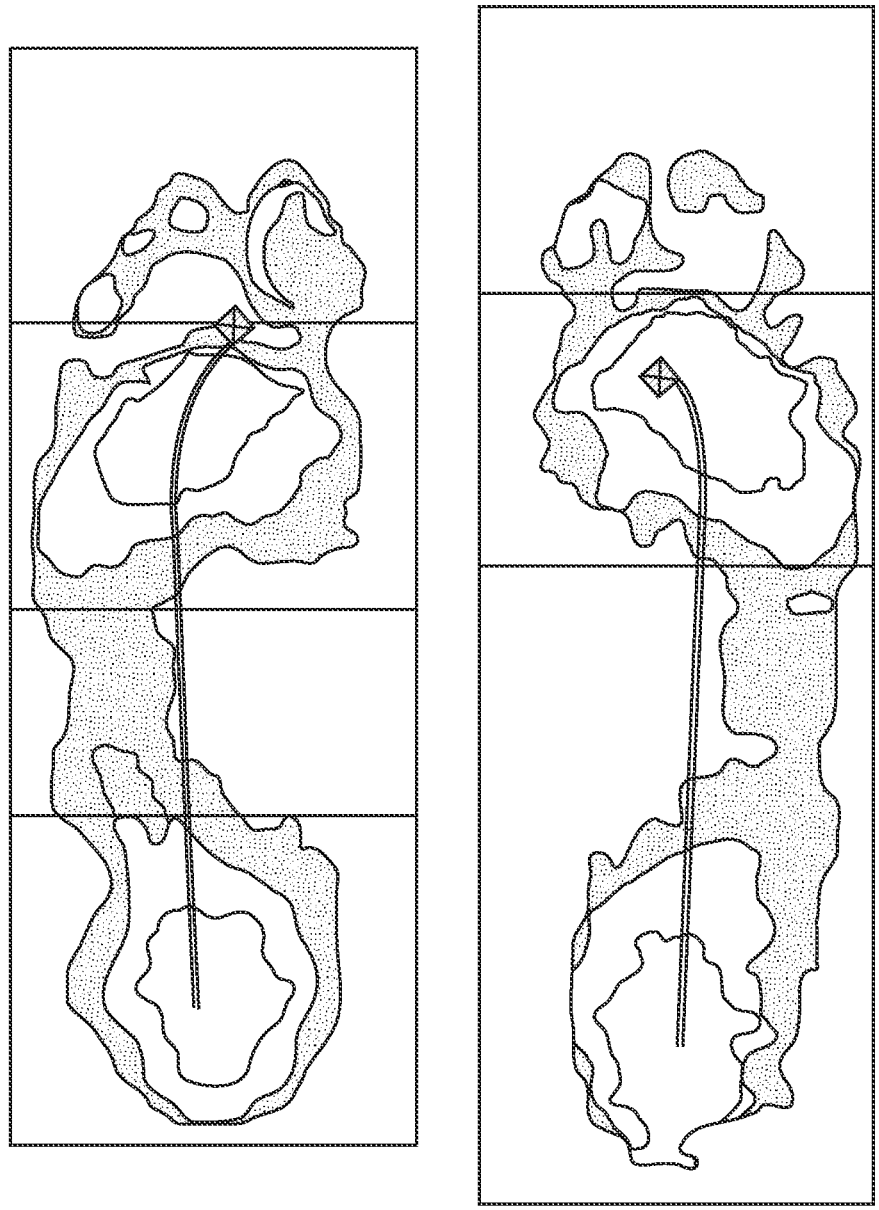
FIG. 5 shows a prior art example of the left and right foot force and relative pressure measurements provided by an existing in-shoe system by F-Scan™.
Figure 6A:
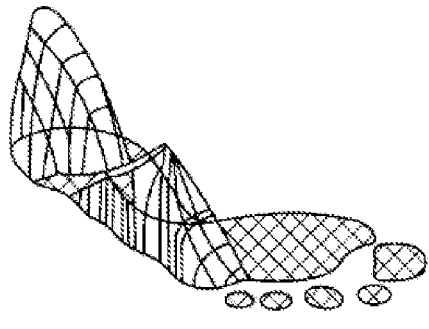
FIGS. 6A-6D are other prior art examples showing insole pressure measurements of the running stride and are FIGS. 9-12 of the applicant's '948 U.S patent.
Figure 6B:
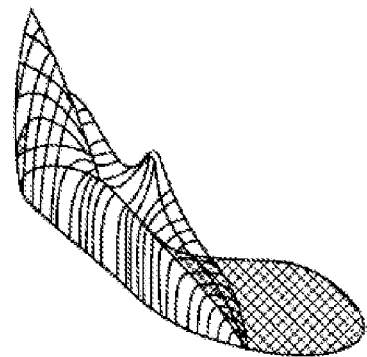
Figure 6C:
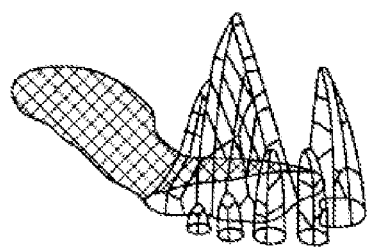
Figure 6D:
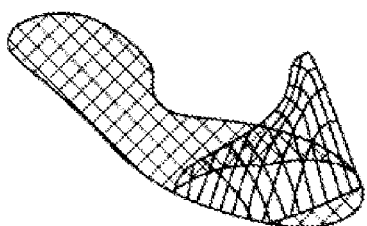
Figure 7:
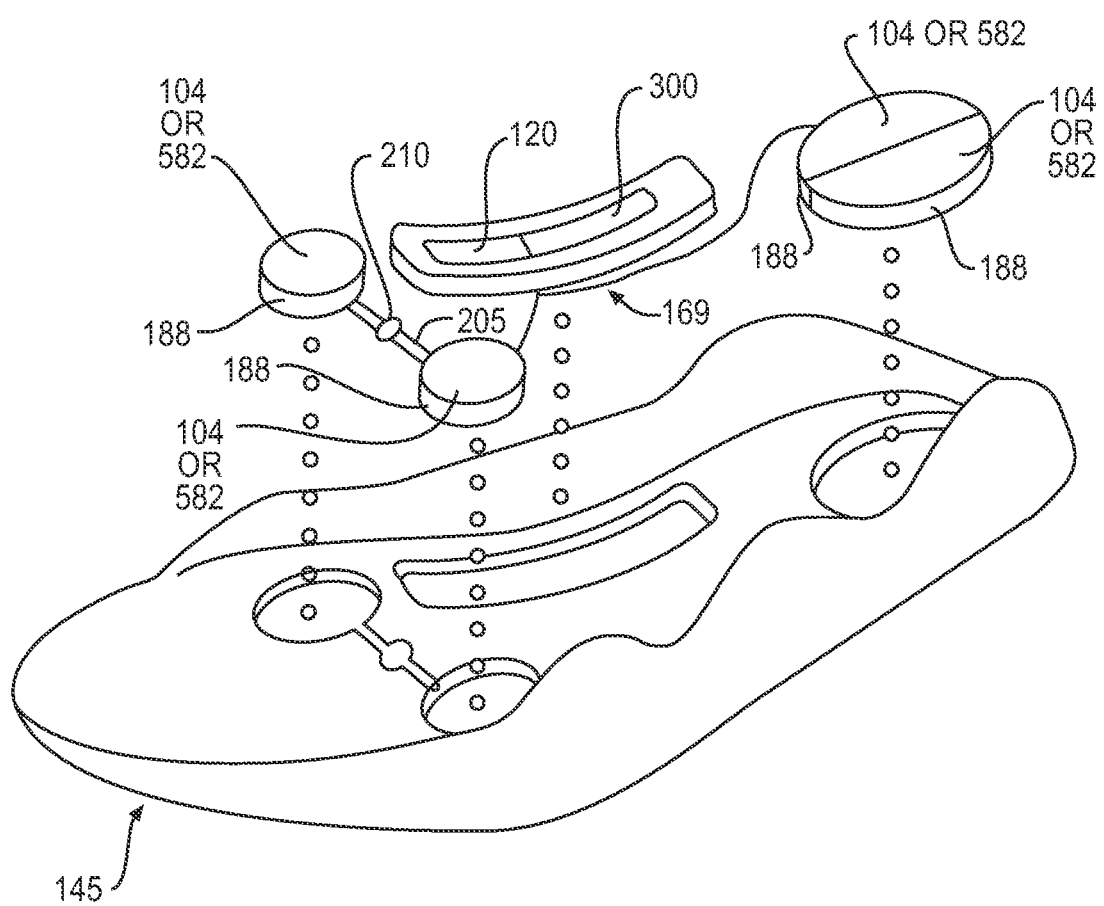
FIG. 7 shows a perspective view of a prior art example of footwear with computer controlled bladders, compartments, or chambers located in a removable midsole section and was FIG. 11P of the applicant's '749 U.S. application publication.
Figure 8:
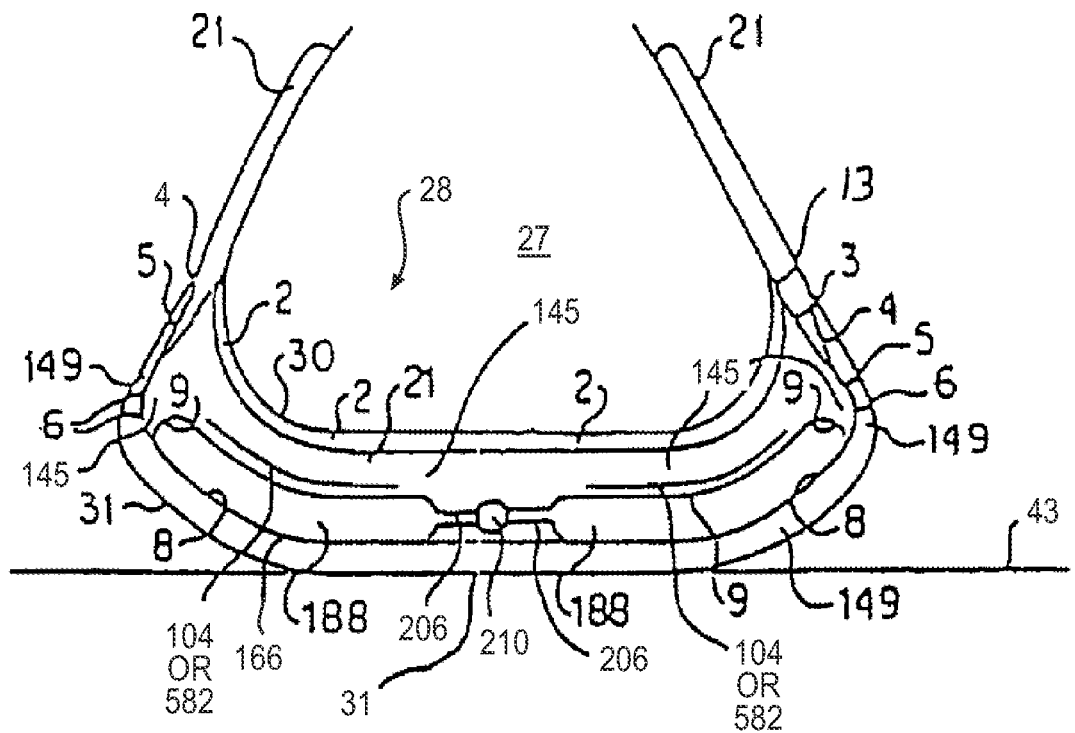
FIG. 8 shows a frontal plane view of a similar embodiment and was FIG. 11N of the same '749 publication.
Figure 9:
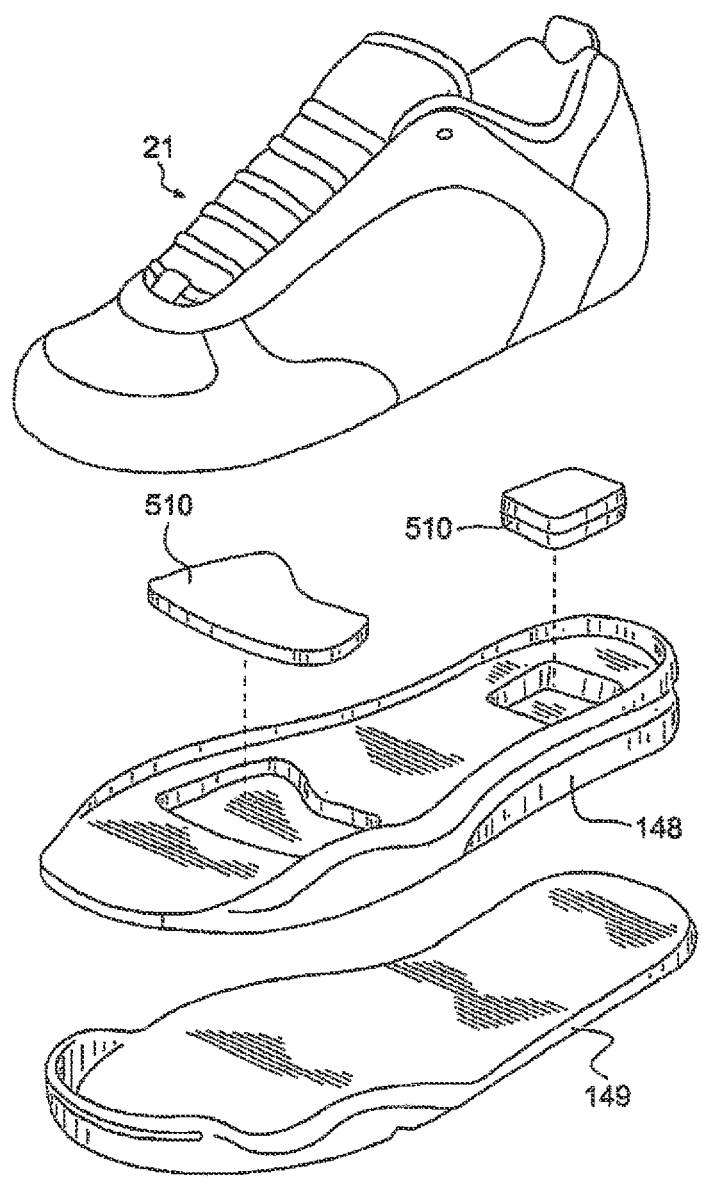
FIG. 9 shows a perspective view of a prior art example of footwear with inner bladders, compartments, or chambers of FIGS. 7 & 8 with internal flexibility sipes and outer, bladders, compartments, or chambers and was FIG. 1C of the applicant's '916 U.S. Publication.
Figure 10A:
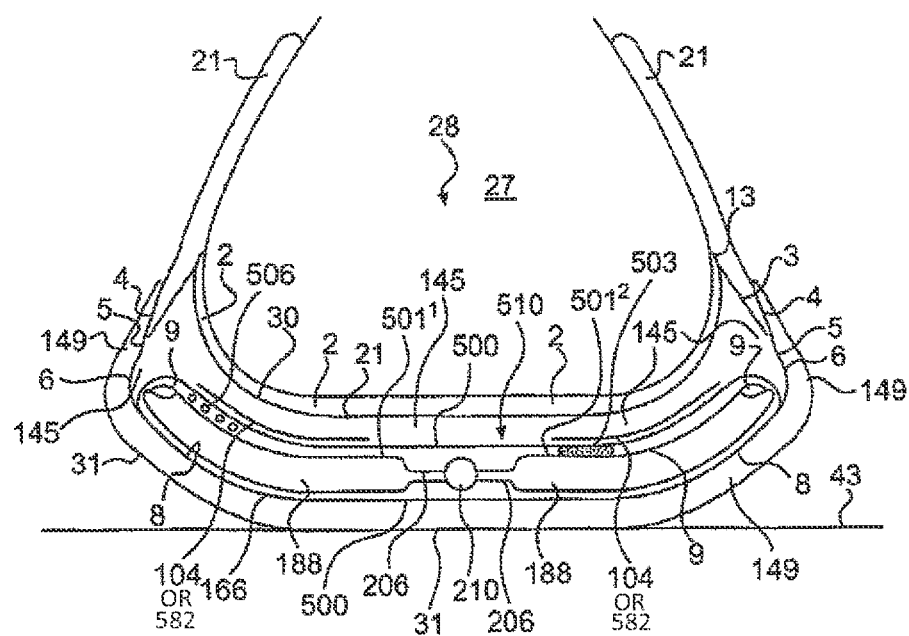
FIGS. 10A-10I show applicant's prior art footwear components.
Figure 10B:
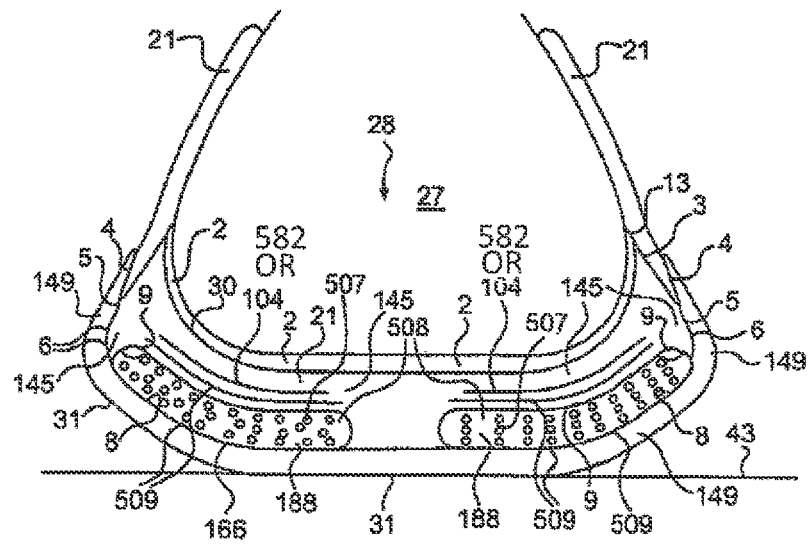
Figure 10C:
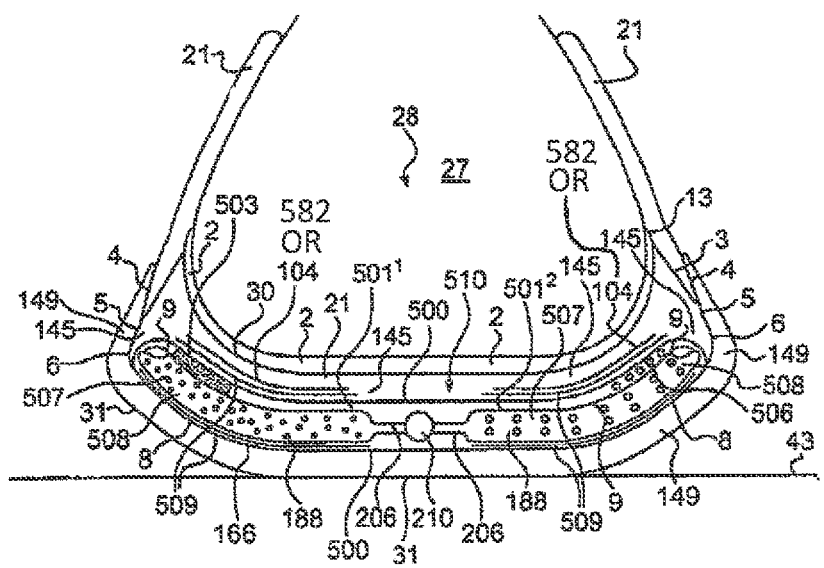
Figure 10D:
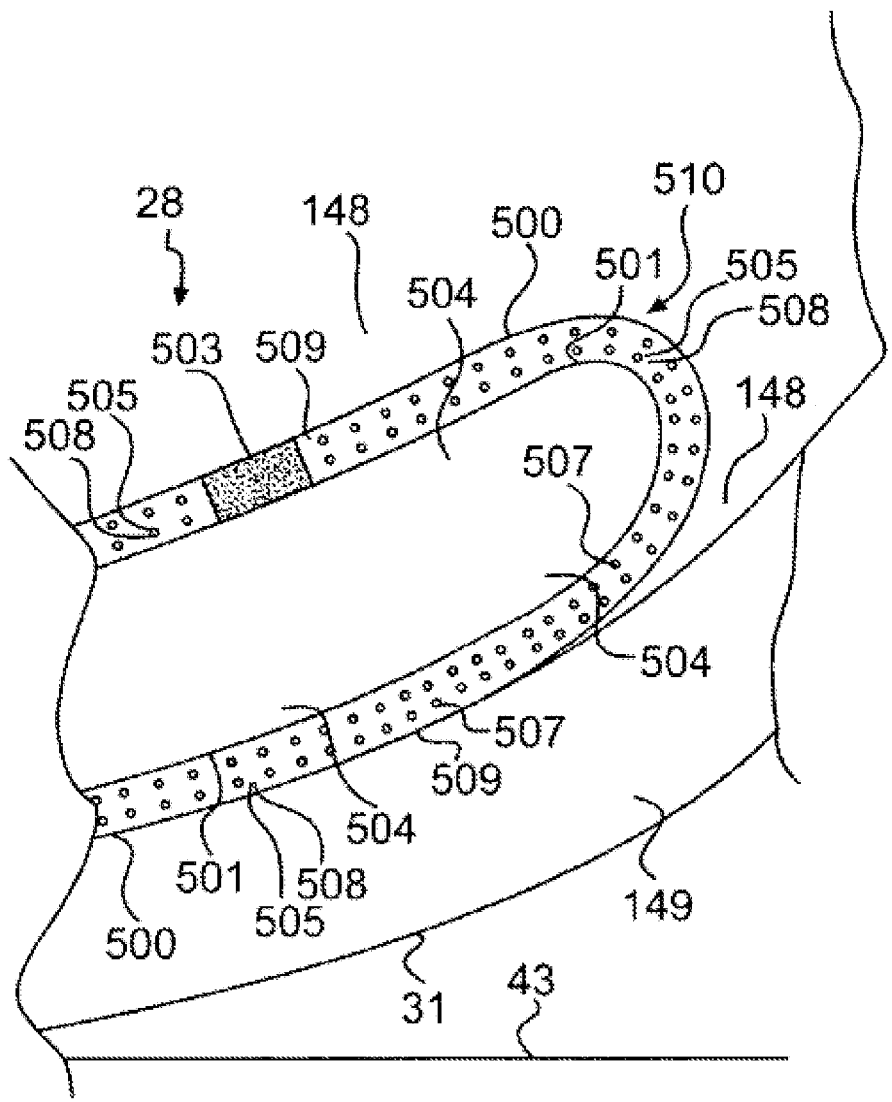
Figure 10E:
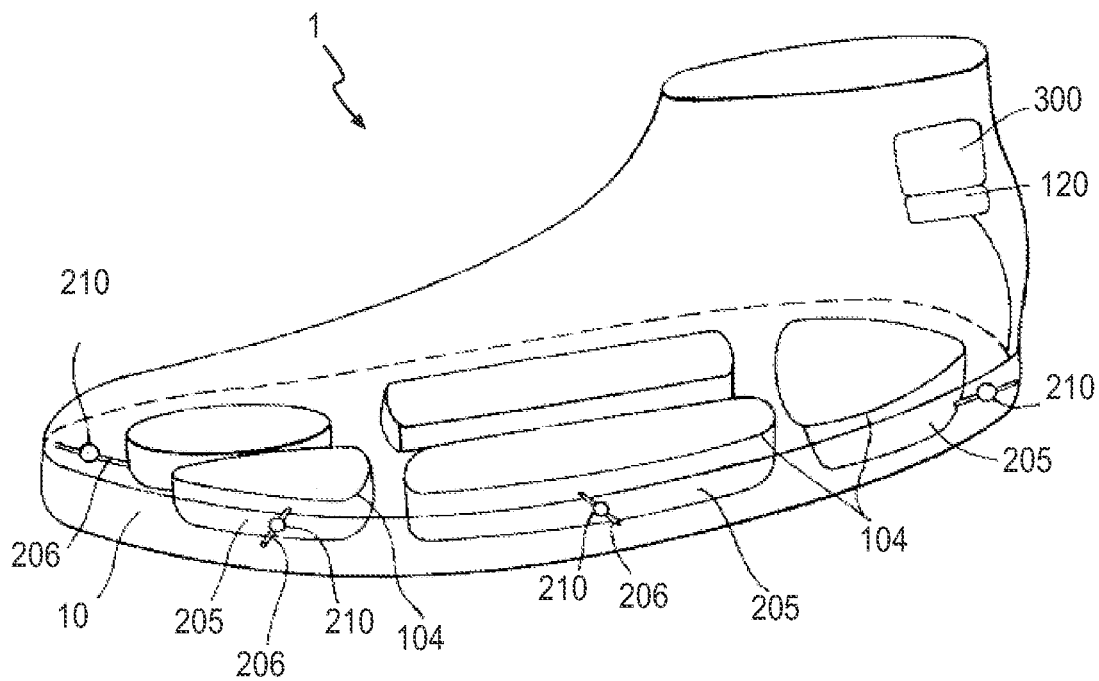
Figure 10F:
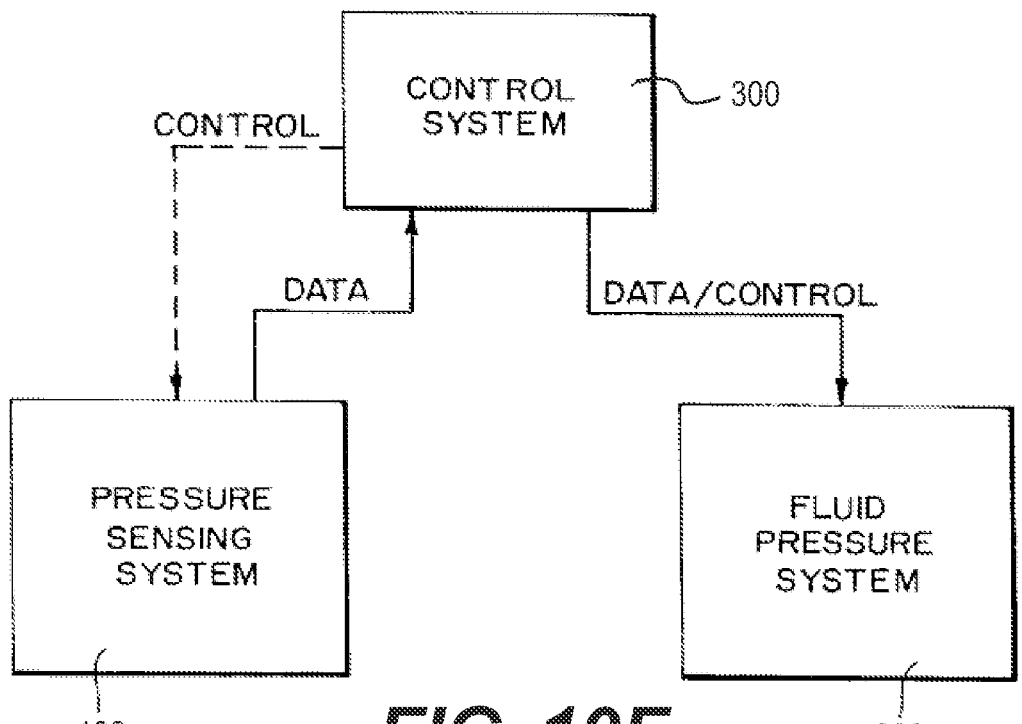
Figure 10G:
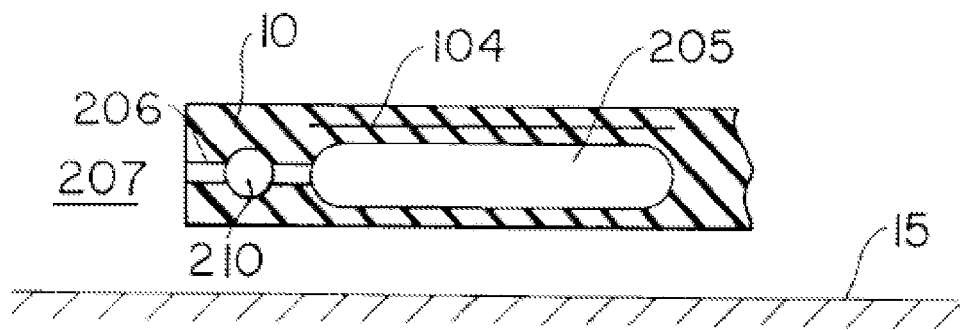
Figure 10H:
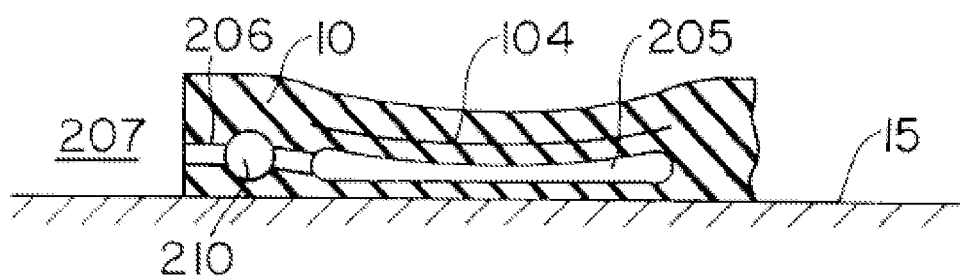
Figure 10I:
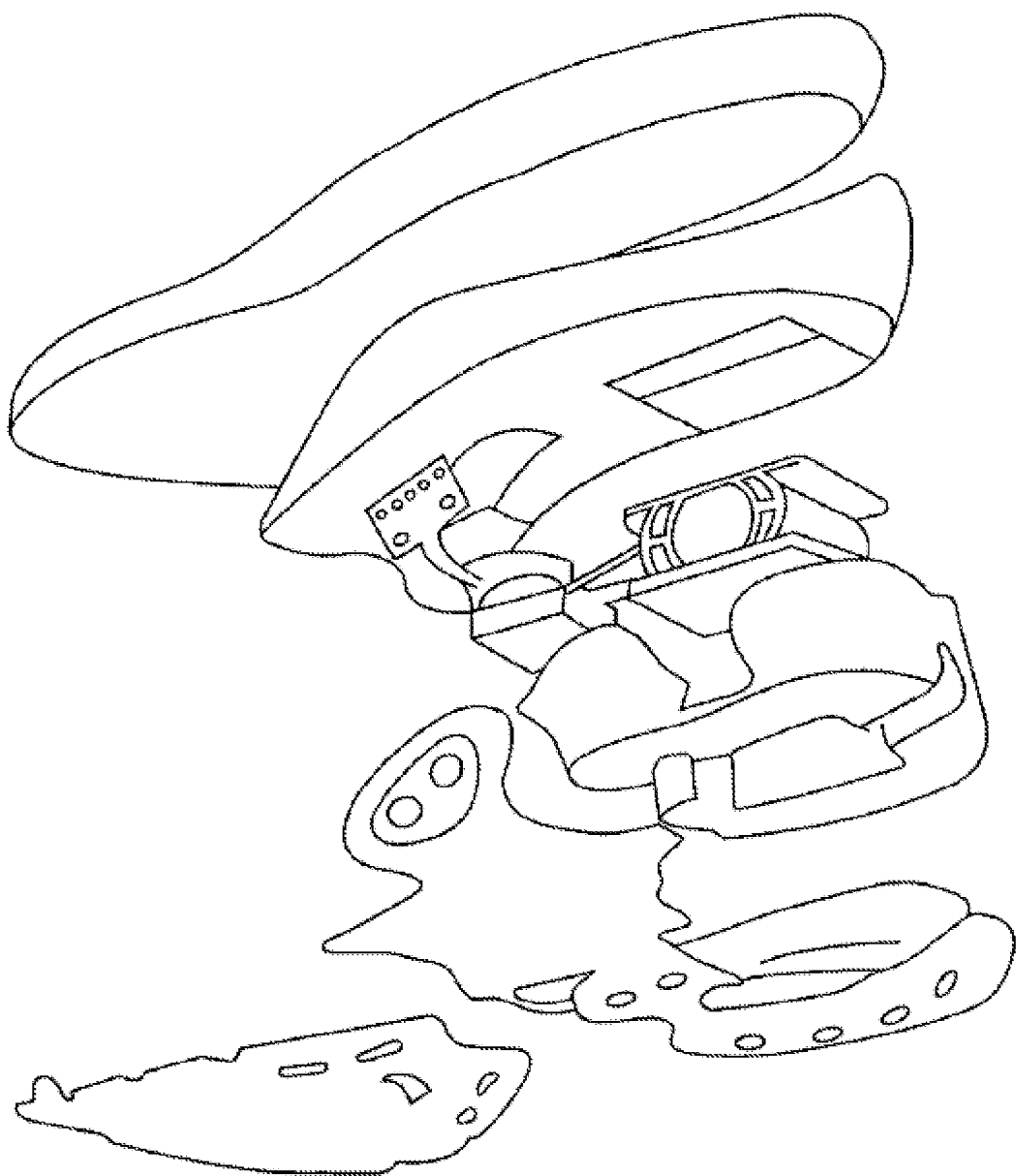
Figure 11A:
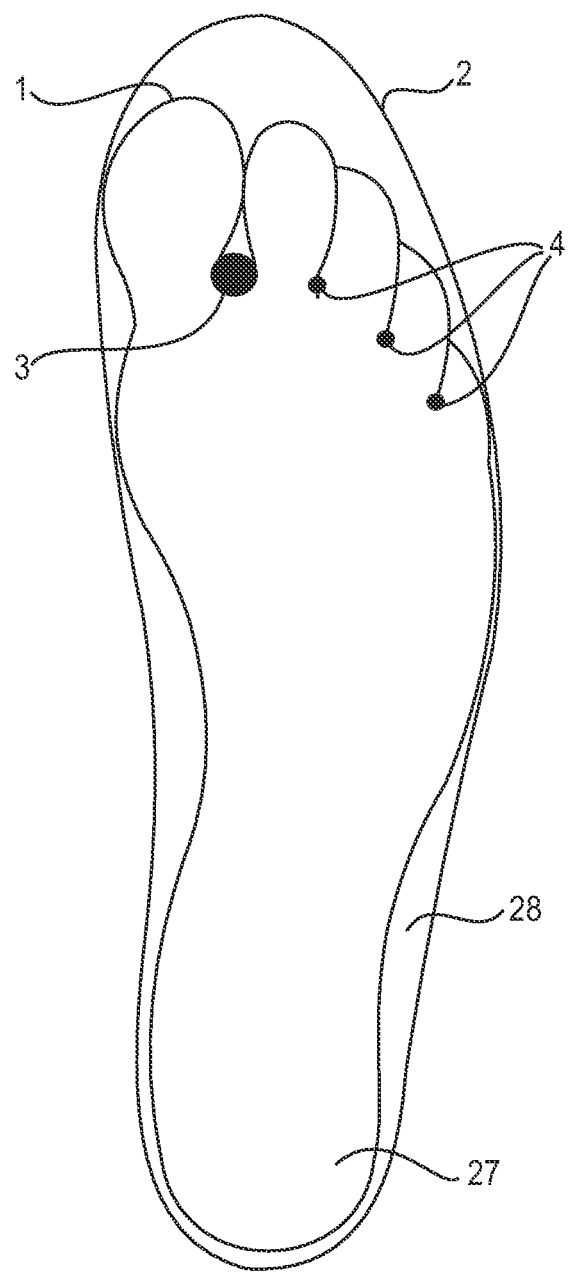
FIG. 11A-11I are examples of the applicant's semi-thong inventions.
Figure 11E:
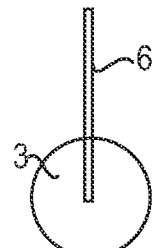
Figure 11C:
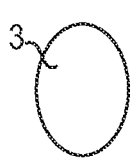
Figure 11D:
Figure 11B:
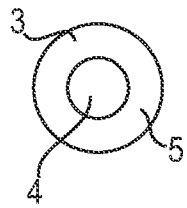
Figure 11F:
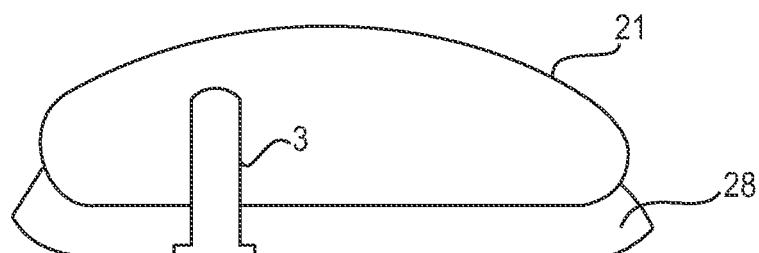
Figure 11G:
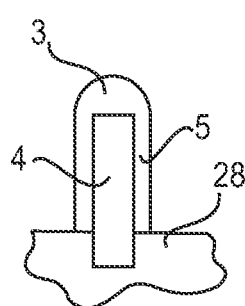
Figure 11H:
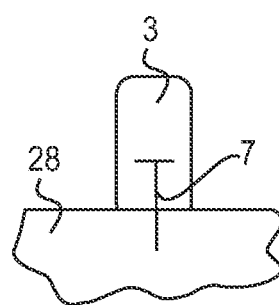
Figure 11I:
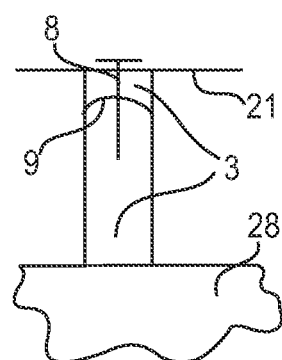
Figure 12A:
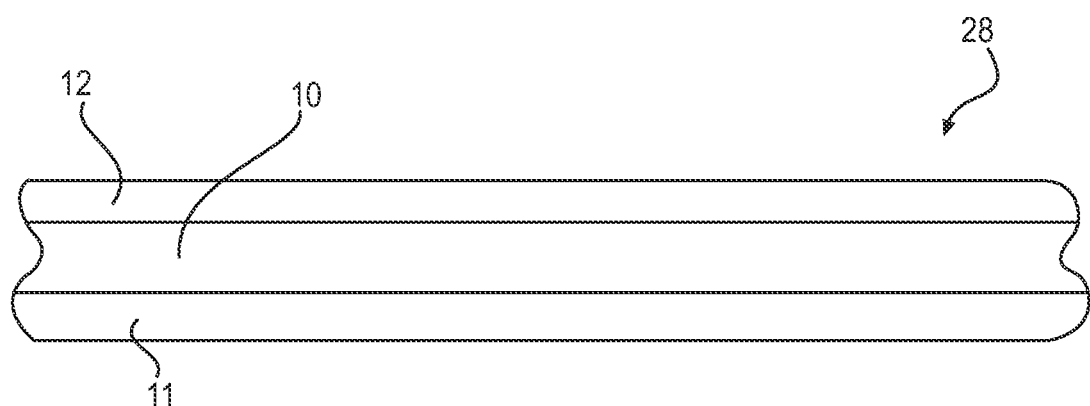
FIG. 12A is a blown up cross-section of an example part of the applicant's inventions of an extremely minimalist footwear sole or a traction sock or an individual thread.
Figure 12B:
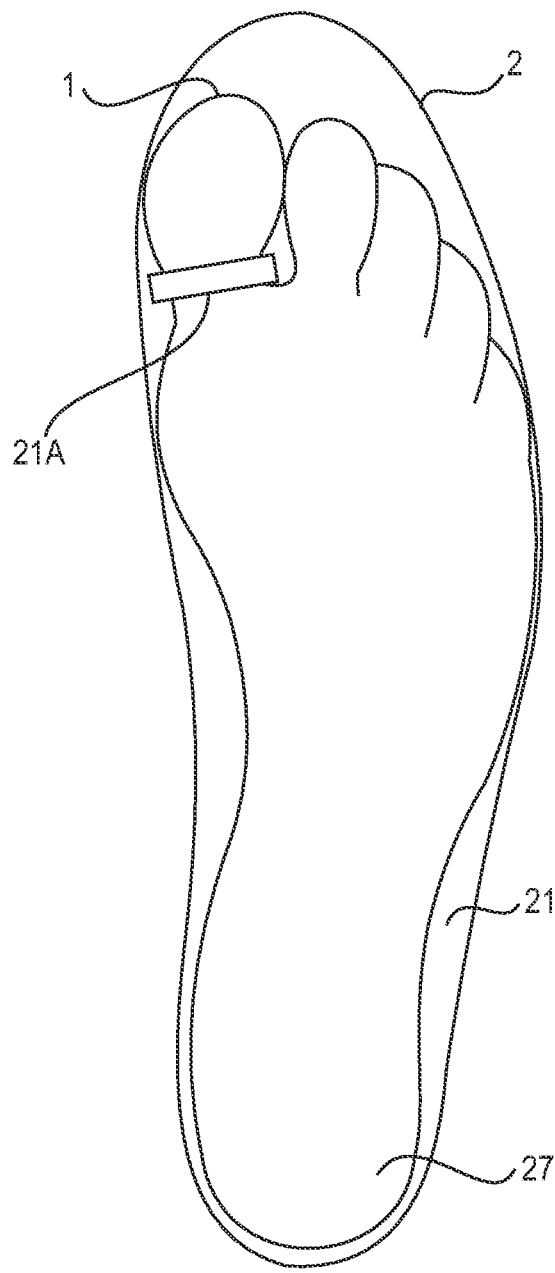
FIG. 12B shows an example of the most minimalist of footwear, which is without any sole and only a big toe strap 21a (and/or other toe straps), elastic or other, to hold down the forefoot of the soleless footwear upper.
Figure 13A:
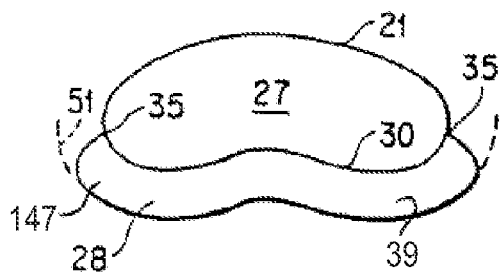
FIGS. 13A-13E is a prior art series showing the applicant's prior inventions of footwear soles conforming to the shape of an intended wearer's unloaded foot sole and was FIG. 51A-51E of the applicant's '350 U.S patent.
Figure 13B:
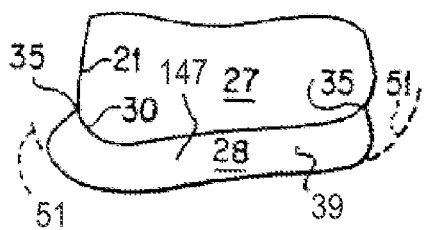
Figure 13C:
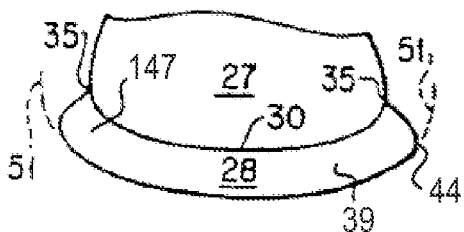
Figure 13D:
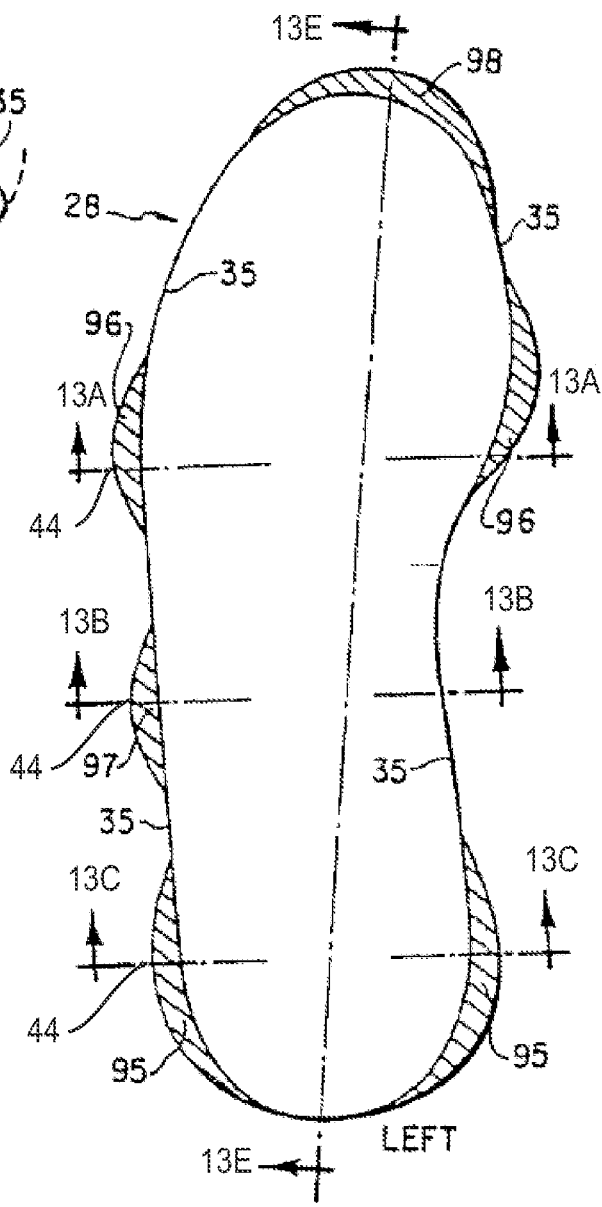
Figure 13E:
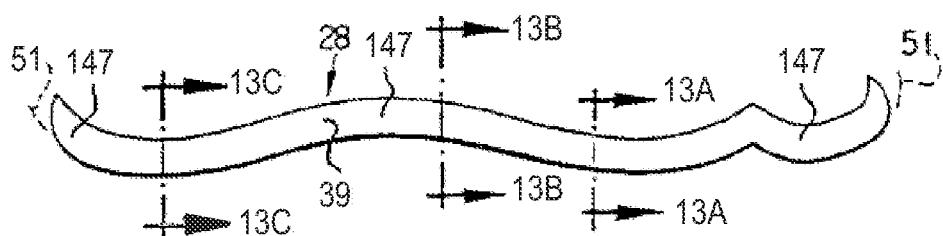
Figure 14A:
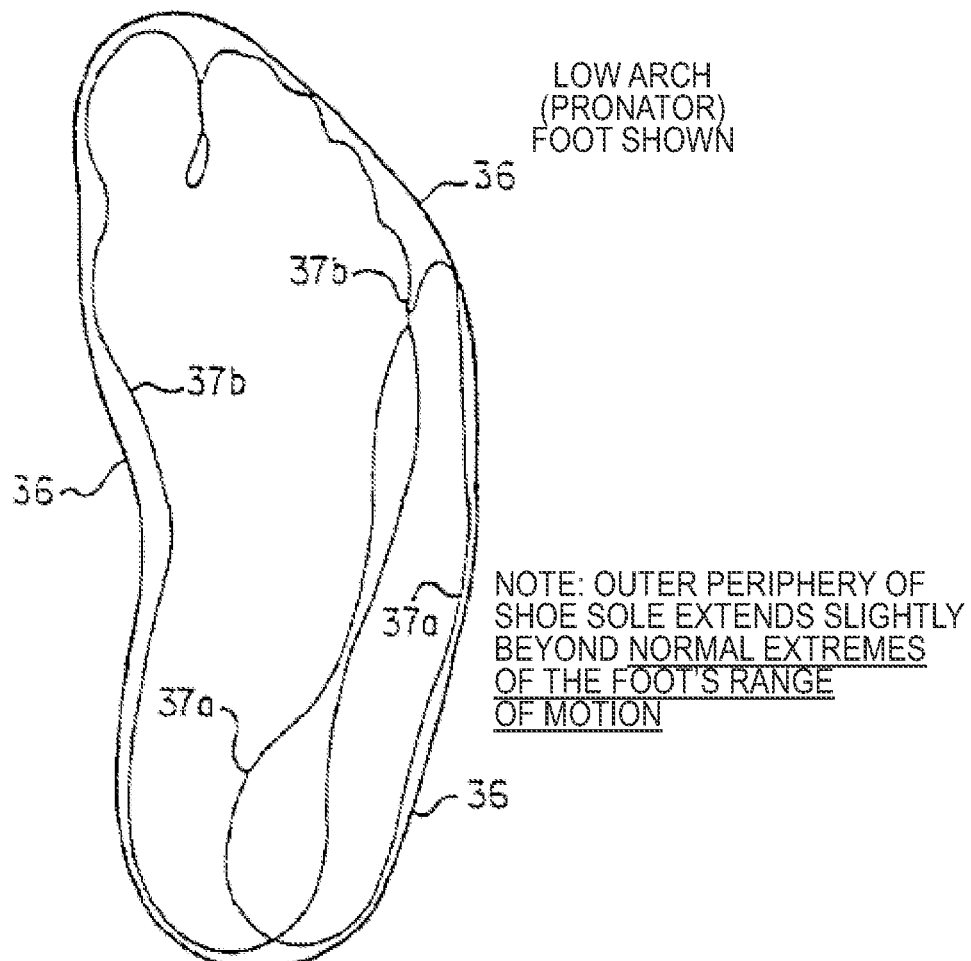
FIGS. 14A-14E show components of applicant's prior inventions.
Figure 14B:
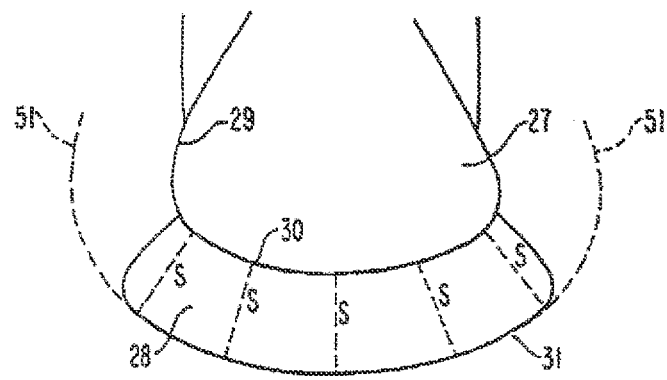
Figure 14C:
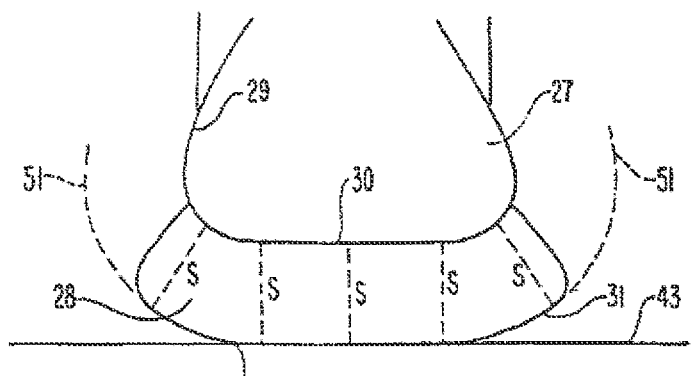
Figure 14D:
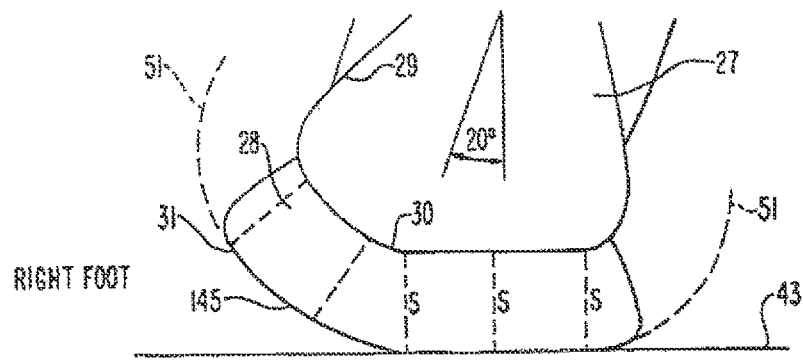
Figure 14E:
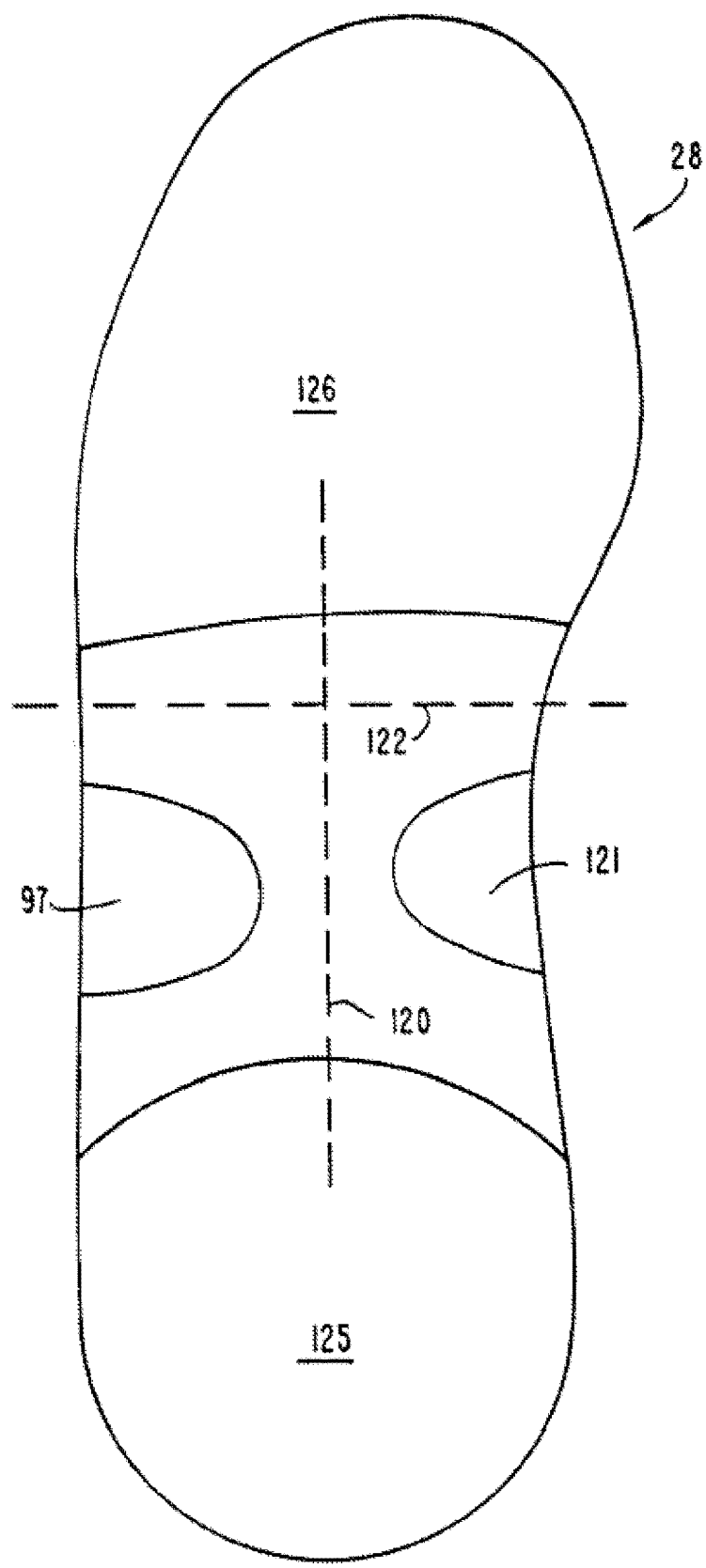
Figure 15A:
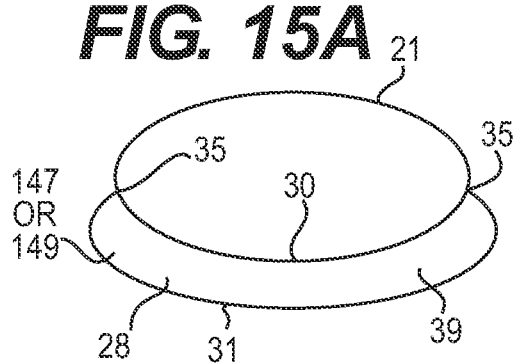
FIGS. 15A-15H is a series similar to FIGS. 13A-13E showing frontal plane and sagittal plane cross-sections and horizontal plan overview of the applicant's new inventions of a footwear sole that is concavely rounded relative to the intended wearer's foot sole in frontal plane cross-sections in the forefoot, midfoot, and heel areas of the footwear sole.
Figure 15B:
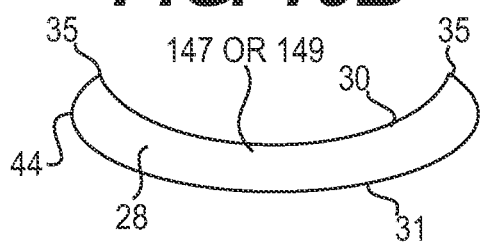
Figure 15C:
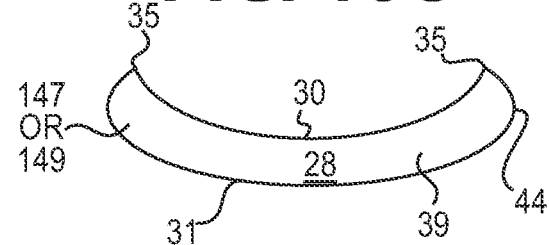
Figure 15D:
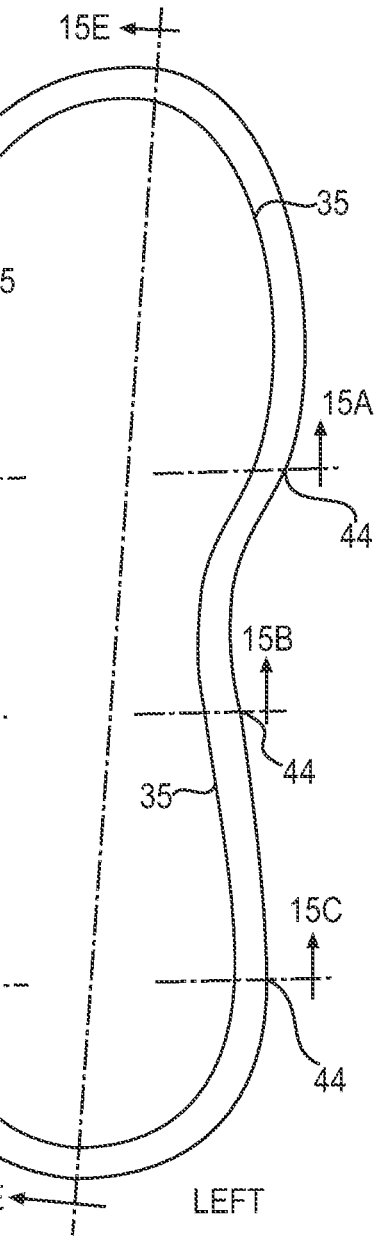
Figure 15E:
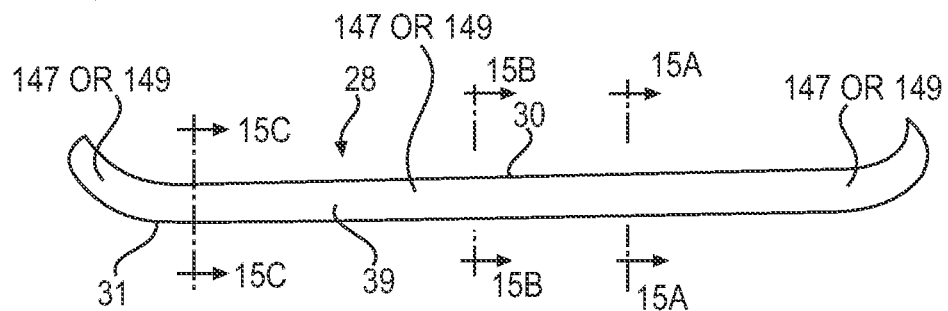
Figure 15F:
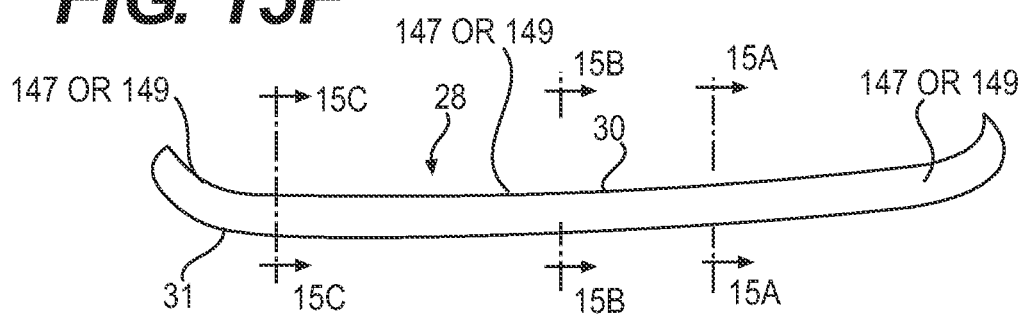
Figure 15G:
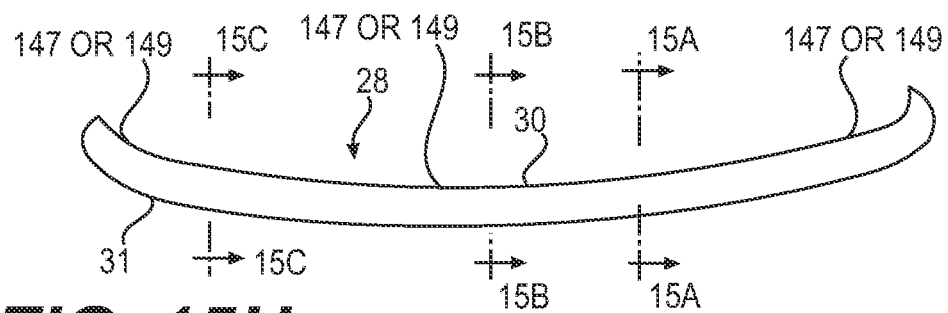
Figure 15H:
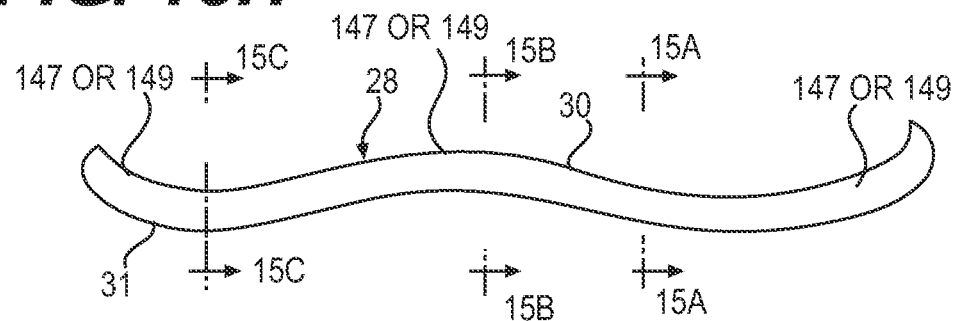
Figure 18A:
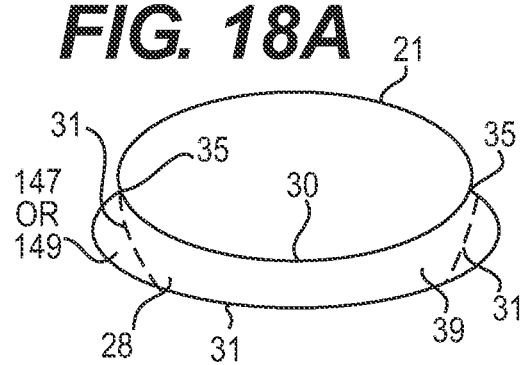
FIGS. 18A-18E show variations of the flexibility groove located proximate to flexibility axis 122.
Figure 18B:
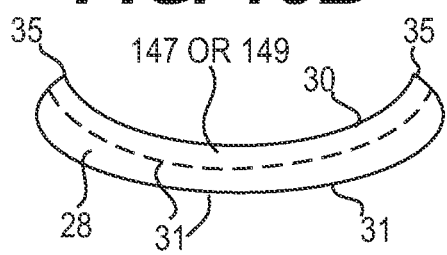
Figure 18C:
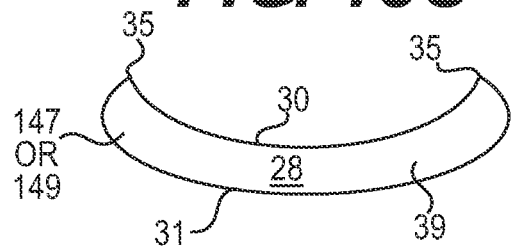
Figure 18D:
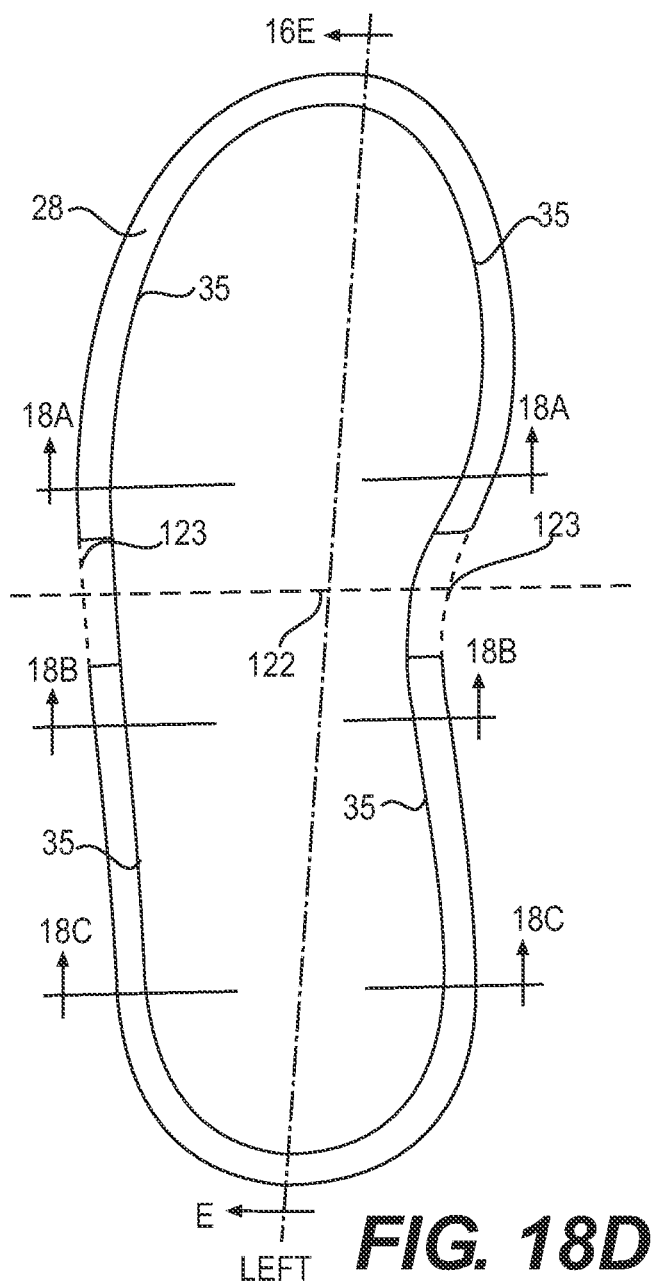
Figure 18E:
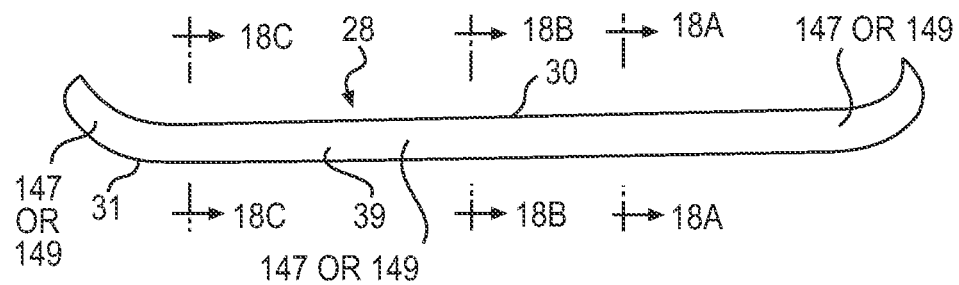
Figure 20A:
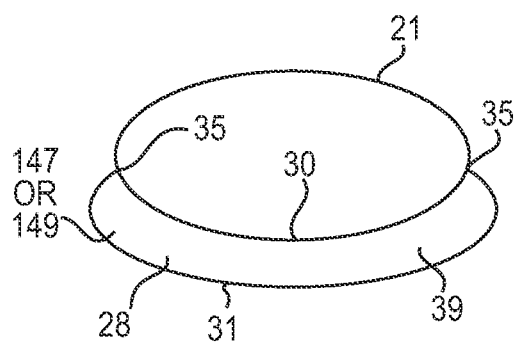
FIGS. 20A-20E show variations of the flexibility groove located proximate to flexibility axis 122, with FIG. 20D showing flexibility sipes 505 instead of grooves.
Figure 20B:
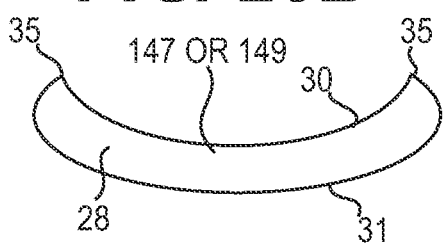
Figure 20C:
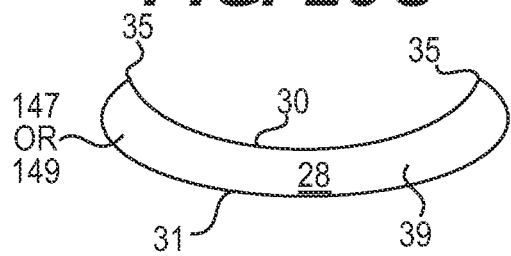
Figure 20D:
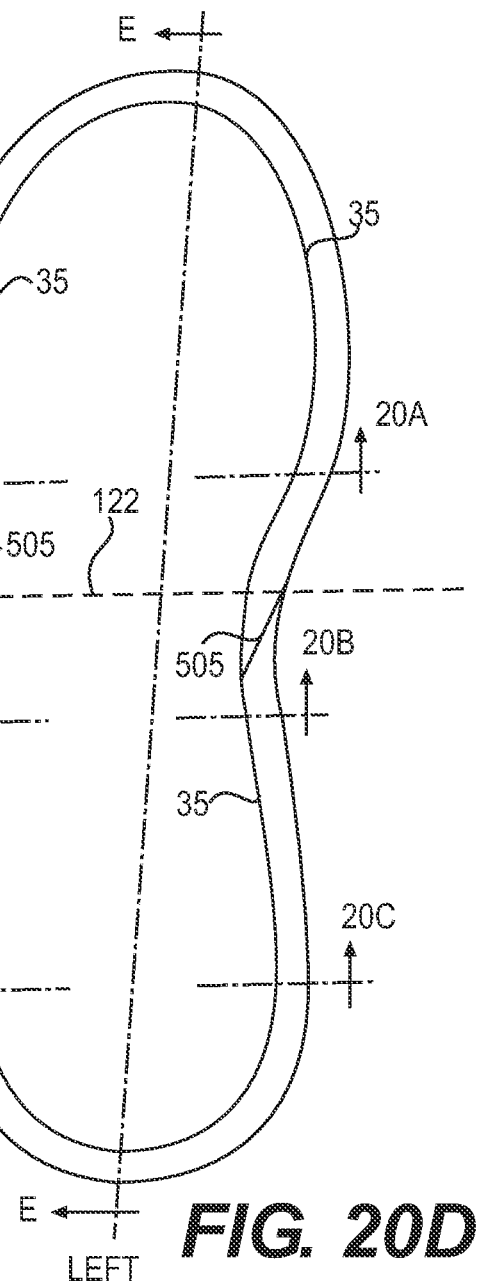
Figure 20E:
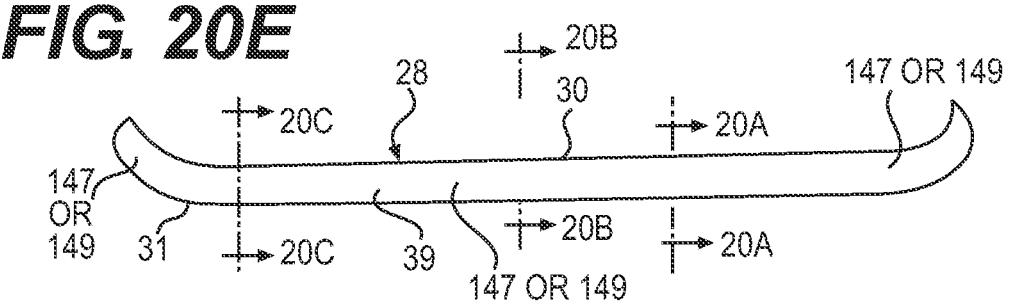
Figure 24:
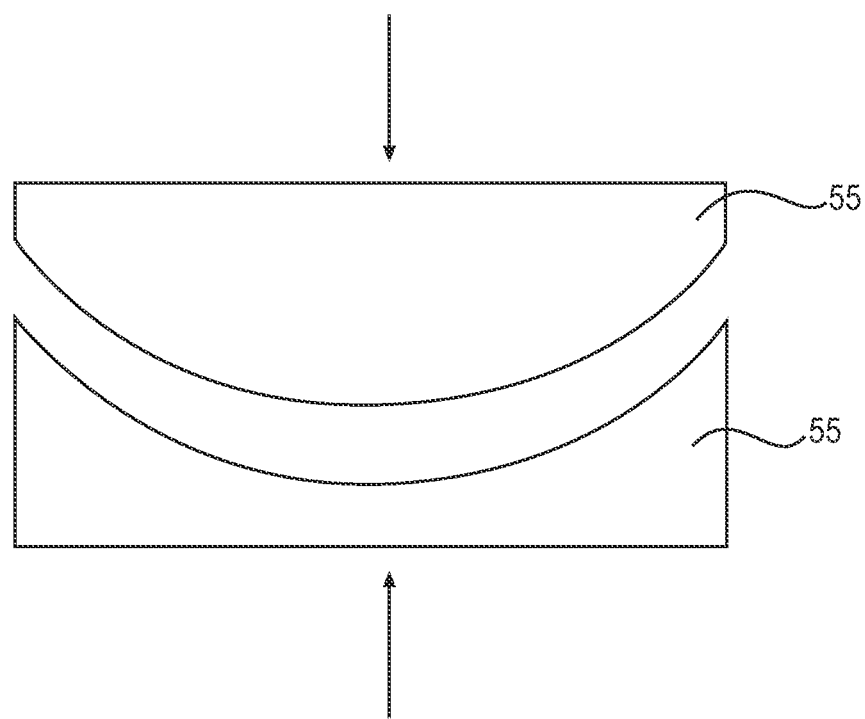
FIG. 24 is a frontal plane cross-section of a press and/or press forms 55 configured structurally to form a concavely rounded footwear sole such as shown in FIGS. 15-23.
Figure 25A:
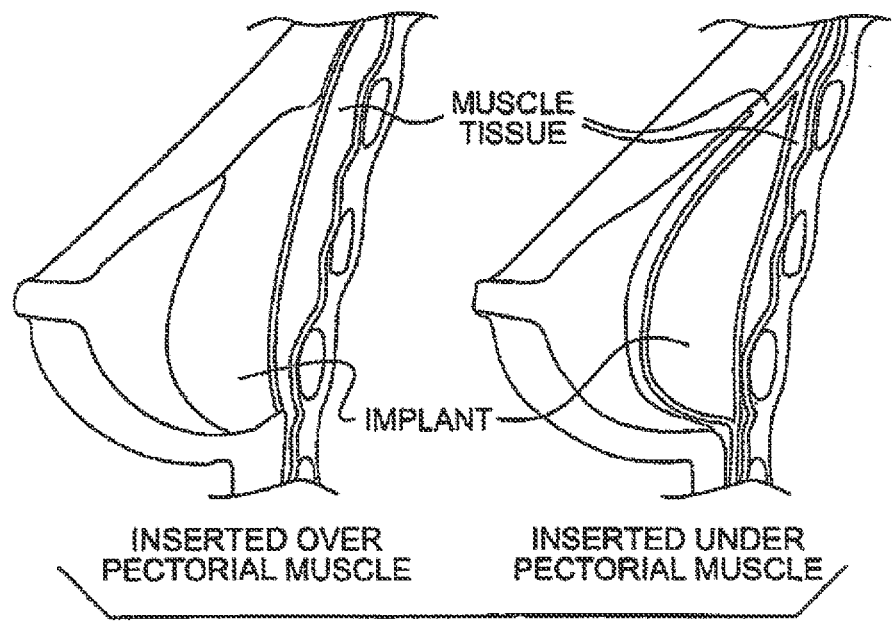
FIGS. 25A-25B are a prior art example based on FIG. 29A from the applicant's '916 application and an example of an apparatus with sensors 582 based on FIG. 29B of the '916 application, respectively.
Figure 25B:
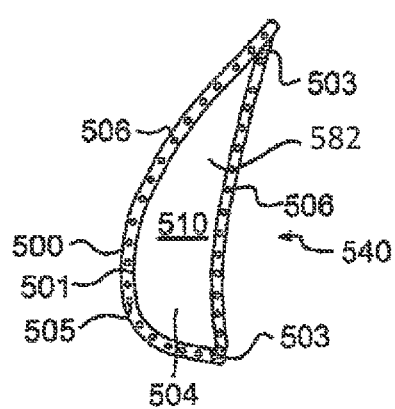
Figure 26A:
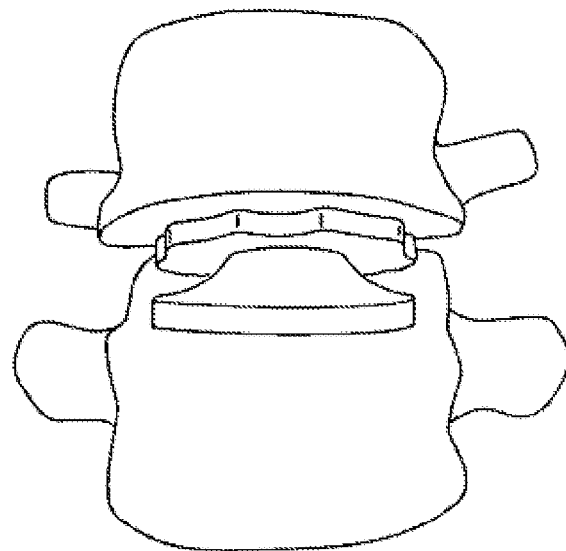
FIGS. 26A-26B are a prior art example based on FIG. 32A from the applicant's '916 application and an example of an apparatus with sensors 582 based on FIG. 32B of the '916 application, respectively.
Figure 26B:
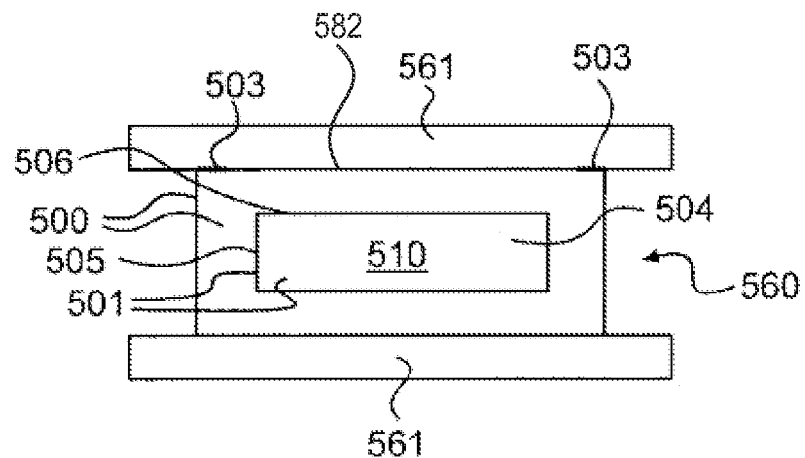
Figure 28A:
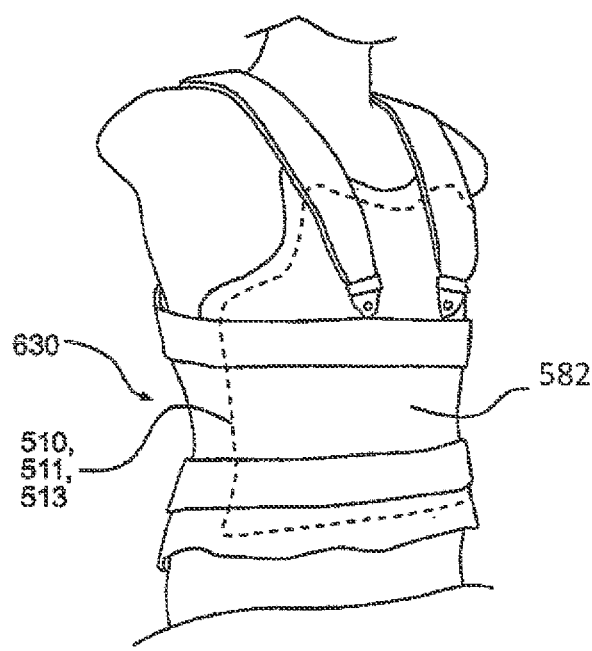
FIGS. 28A-28B are examples of apparatus with sensors 582 based on FIGS. 69 and 79 from the applicant's '916 application.
Figure 28B:
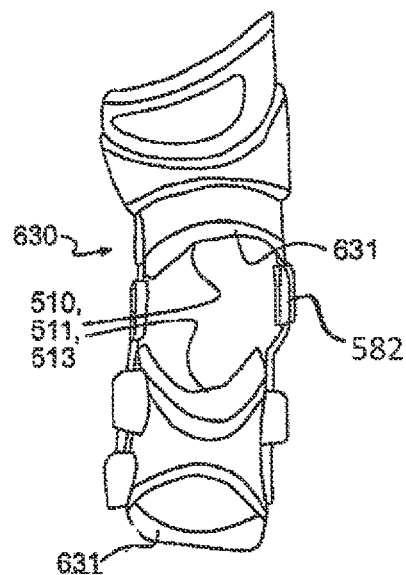

The smartphone 580 and/or associated peripheral device with remote sensor or sensors 582 and/or other devices can be especially useful in measuring the relative motion of the body or one or more body parts of a user and/or wearer when the wearer is in any form of locomotion or gait, including walking and running. For example, an iPhone™ can be attached to a user's belt and located proximate to the small of the back of the wearer, as shown in FIG. 3, at which location the iPhone™ is positioned close to the wearer's center of gravity (C.G.) and therefore data measurements of the wearer at that location during walking or running, for example, approximate fairly well the wearer's center of gravity (C.G.) motion during that locomotion, such as lateral or side-to-side C.G. motion in a frontal plane.

Besides the smartphone 580 being carried by the user/wearer, it can be maintained in a relative position close enough to the user/wearer that the smartphone can communicate wirelessly with one or more peripheral devices with sensors 582 on a test subject not carrying the smartphone during a test; alternatively, another computer like a tablet or laptop or desktop can be configured to perform the same functions as a smartphone device 580, although with less or little mobility; such a peripheral device with sensors 582 can itself also simply record data measurements for later transfer to the smartphone 580 or other computer in a wired or wireless or a memory card like a USB drive or SD card, for examples.

In addition, the smartphone device 580 can be configured so that when it is paired with another motion sensor besides that in the smartphone or other device 580 itself, such as a separate sensor or sensors 582 in a peripheral device like an EarPod™ set or headphones; for example, that second sensor or sensors 582 can be configured to measure 1D, 2D, or 3D data of the relative motion of the wearer's head during locomotion (assuming earplug-like fixation by the ear canal) and that data can be recorded by and/or streamed to the smartphone device 580. The smartphone 580 such as an Apple iPhone™ can be configured to receive the data set of the head motion and compare that head motion data set with its own CG motion data set and/or send that head motion data set and/or its CG motion data set to the Apple iCloud for such comparison and/or both iPhone™ and iCloud™ can share the data set comparison and perform other functions in a shared operation and/or with either performing any given operation or part thereof independently.

The results of that motion data comparison and any other operation can be recorded and/or stored and/or transmitted or otherwise made accessible to the user/wearer and/or to an approved third party such as a doctor or podiatrist or biomechanics specialist or other professional or semi-professional technician, including licensed or not, who is treating, consulting, or evaluating the user/wearer for overuse injury or acute injury (including accidents of any type) or to prevent injury and/or optimize performance for locomotion including for work, sports, leisure, or activities of daily living. There can be any practical number of additional and/or separate motion or other sensors 582 of any useful configuration that can be located at any practical number of body parts of a user/wearer. The sensors 582 can be attached, fastened, or worn in any practical manner, including implanting in a human body (or in an animal body or in a plant). The smartphone or other device 580 can also be configured to receive shared data from other smartphones or other devices 580 and/or other shared peripheral devices with sensors 582 located with other user wearers.

The smartphone or other device 580 can also measure absolute or geographic position of the wearer, such as by the global positioning system (GPS), compass, or other system, method or component, and can record and/or correlate in real time the absolute position (CG or other approximate point) of the user/wearer with the relative position motion of one or many body parts of the user/wear (or the same information shared from other smartphone 580 user wearers), and/or stream in real time or transmit the data sets to a cloud like the iCloud™ example above.

The position measurement, either relative or absolute, can be in one plane (1D) or in two planes (2D) or in three planes (3D), with correlated time measurement for example as well; sagittal, horizontal, and/or transverse (or frontal) planes are examples. Other data sets can potentially be captured, recorded, processed and/or transmitted by the smartphone or other device 580 or connected sensor or sensors 582, such as blood pressure, heart rate, respiration rate, blood sugar level, weight, body temperature (core or a body part), ambient temperature, or any other body or body part measurement, medical or other.

The sensor or sensors 582 can be of any type, including the examples of relative and absolute motion, pressure, force, time, heat, moisture, chemical, electrical or electromagnetic, including visible light. The sensors 582 can be located in any practical location on any article of apparel or personal equipment, including the examples of earphones or earplugs, headphones, hat, helmet, protective padding or armor, braces, prosthetics, glasses, watch, belt, waistband, armband, attached with tape or bandage or glue, necklace or lanyard, cervical collar, ring, headband, in any manner attached or embedded in conventional or specialized clothing. The sensors 582 can also be worn or attached onto or implanted in the wearer's body, temporarily in a body piercing or permanently in a body implant.

The sensors 582 can also be located in the user's footwear of any form or type, including in orthotics or prosthetics. The sensors 582 can be entirely diagnostic, such as the example of dynamic footsole force and/or pressure sensors 104 like F-Scan™ and similar in-shoe products like insoles. The footwear sensors 582 can also work with active foot motion control devices, like the example of computer controlled compartments located in or on footwear soles and/or removable in-shoe inserts like the examples shown in FIGS. 11A-11C, 11M, 11N, 11O, and 11P in the '350 patent and FIGS. 11A-11C, 11M, 11N, 11O, 11P, 11T, 11U, 97, 98, and 99A & B in the '665 patent application; the U.S. Pat. No. 5,813,142 to Demon is another example of the prior art. The example embodiments shown in these figures can be used to proactively and/or reactively alter shoe or orthotic (or prosthetic) soles to control the relative foot position between the right and left feet of the user/wearer's feet, such as to alter the neutral position of either or both feet separately toward a more generally supinated or pronated position, or for another example to alter the relative height of any specific portion of the right and/or left shoe or orthotic or prosthetic sole, such as the forefoot, heel, or midsection or under any one or more bones of a user/wearer's right and/or left feet, or under the full right or left foot. These sole configuration alterations can be set potentially by smartphone device control for any time period, including dynamically for each step during locomotion of each foot of the user/wearer and/or dynamically many times during each step, and a data record of the alterations can be recorded and/or streamed from within each sole or in the sensor 582 or in the smartphone 580.

These footwear or orthotic sole alterations can be controlled by the smartphone device 580 based its 1D or 2D or 3D motion measurements, for example, of the user/wearer's body part or parts, including center of gravity motion (CG) during some form of locomotion. One example would be to correct for excessive lateral movement of the user/wearer's center of gravity to one side more than another, as measured in the frontal plane, compared to an established norm less prone to injury. Another example, which can be related, is to reduce the crossover of right and/or left extremities (legs and/or feet) across the centerline of the user/wearer's body, as measured in the wearer's frontal plane during locomotion. Pre-programmed solutions can be applied using the user/wearer's smartphone and/or a cloud, and real time or subsequent testing can be conducted, including by the third parties like a doctor or other professional or technician referenced earlier, by using the smartphone, including to connect directly to the third party or parties or to a cloud for shared or independent operations.

The smartphone is poised to revolutionize medical care. A super powerful personal computer located on or near a human body almost 24/7 that connects to the Internet and with sensors directly on the body provides a previously unheard of potential for health care monitoring and direct, real-time treatment.

The overall picture of this relatively imminent medical future was laid out in detail in 2015 in a book by Dr. Eric Topol titled, "The Patient Will See You Now: The Future of Medicine is in Your Hands" New York, Basic Books, Print. The title emphasizes his view that in that future the patient will have far more control of his own personal health care than is the case now.

The smartphone will also revolutionize medical care in a way unforeseen by Dr. Topol. In short, the smartphone is the key component in a system that actively monitor sensors in the shoe soles and on parts of the body like the small of the back (roughly, the body's center of gravity) and the head. The smartphone can then use that information to evaluate and control electronically configurable structures in the footwear, correcting and optimizing in real time the body's personal biomechanics while running or walking or just standing around.

To put this into proper context, the capabilities and potential benefits just described of this invention combining smartphone and configurable footwear soles goes very far beyond anything that can be done today for anyone in even the most sophisticated and best equipped footwear biomechanics lab anywhere.

Moreover, the smartphone can connect to a web-based cloud computer system that can compare anyone's data with that of others using the same system, which could easily become a database of millions of users. Big data techniques can then be used on all that data to find important correlations for anyone and others physically alike that would be impossible to spot any other way. Big Data techniques are described in the book, Mayer-Schönberger, Viktor and Cukier, Kenneth. 2013. Big Data: *A Revolution that Will Transform How We Live, Work, and Think*. Boston: First Mariner Books. Print.

Reliable solutions to structural and/or functional problems that many others have already had that are the same as anyone's problems can be downloaded from the cloud to the user's smartphone. The smartphone can then use the solution to configure the user's footwear soles.

The whole process of the cloud/smartphone/footwear system would be ongoing continuously. It thereby continually optimizes corrections to existing damage anyone may have from elevated shoe soles.

The operating systems of the above described smartphone or other device 580 can be an iOS™ or Android™ or Windows Phone OS or BlackBerry 10 for an Apple™ or Android™ or Windows™ or Linux™ smartphone or tablet, for example; other operating systems, existing or future can be used to perform those operations. Such an app can be downloaded from Apple™ or Google™, for example, or for a Kindle™ downloaded from Amazon™ or downloaded from Microsoft™ for the Nokia Lumia™ for other examples. The operations described above for one or more sensors 582 can also be controlled by the same app as for the smartphones or other device 580 above. The app can be software alone or include one or more special or new sensors 582 and/or other hardware and/or firmware.

At least the footwear specific portions of the app can be developed by a footwear vendor like Nike™ Adidas™ or Under Armor™, for example, and/or an independent or university biomechanics laboratory, and the overall app can be co-developed with the smartphone 580 and sensor 582 hardware makers, as well as the smartphone operation system developers, of which examples have been cited above. Data sets from the smartphone or other devices 580 can be transmitted to a World Wide Web site for processing, evaluation (especially comparison with other wearers or users), storage, sharing, and other functions for the user wearer of the smartphone 580 (and may include the use of cloud resources) run by any of the entities referenced above.

Figure 29A:
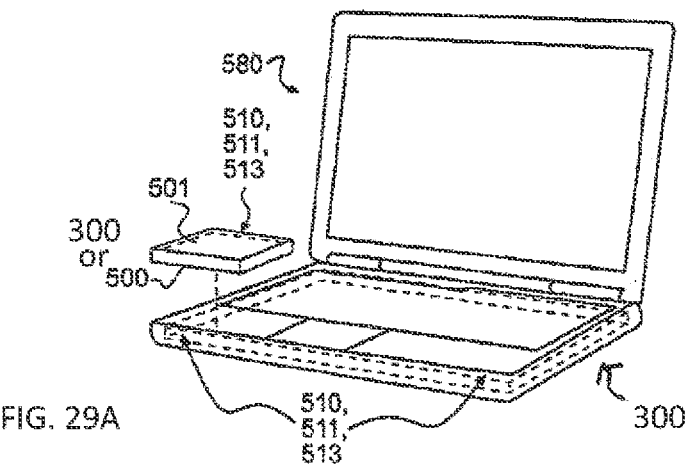
FIGS. 29A-29B are examples of apparatus with sensors 582 based on FIGS. 61A & 62B from the applicant's '916 application.
Figure 29B:
Figure 30:
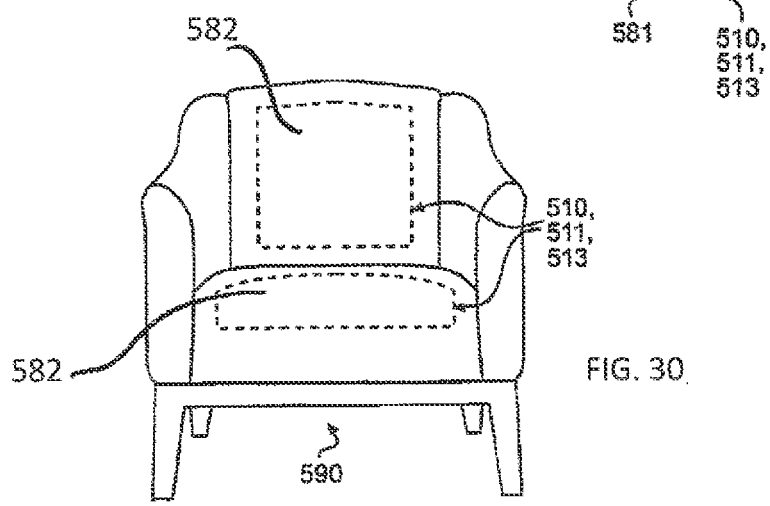
FIG. 30 is an example of an apparatus with sensors 582 based on FIG. 62 from the applicant's '916 application.
Figure 31:
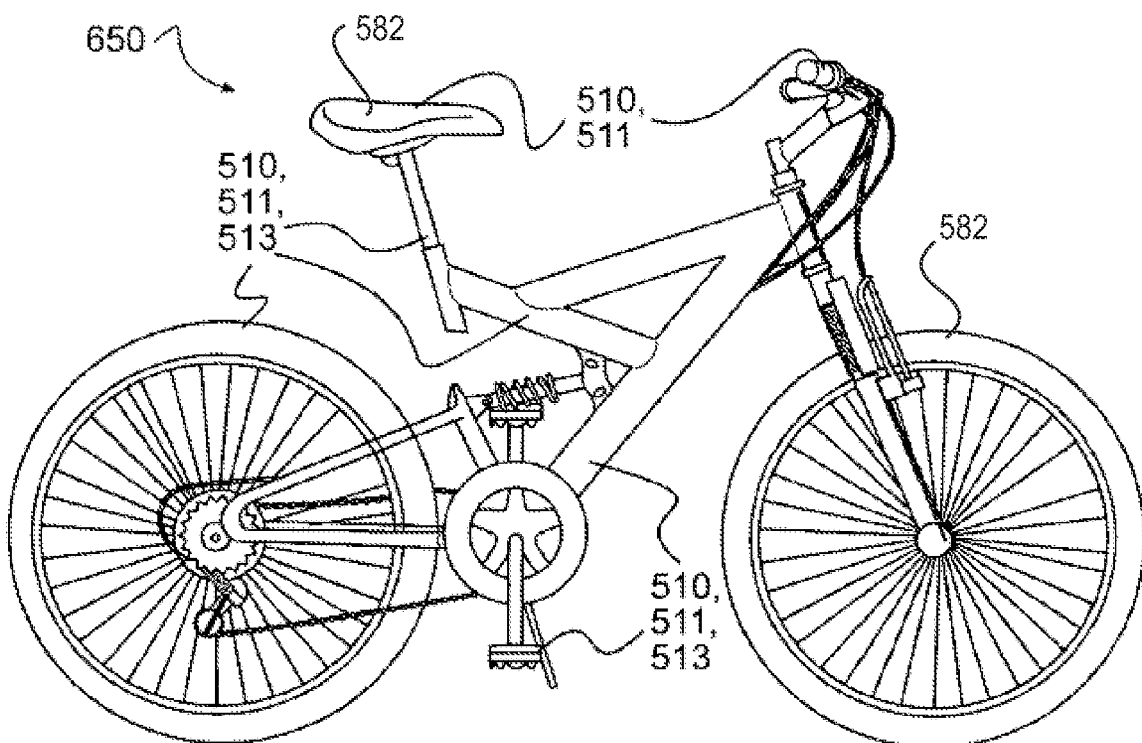
FIG. 31 is an example of an apparatus with sensors 582 based on FIG. 78 from the applicant's '916 application.
Figure 32:
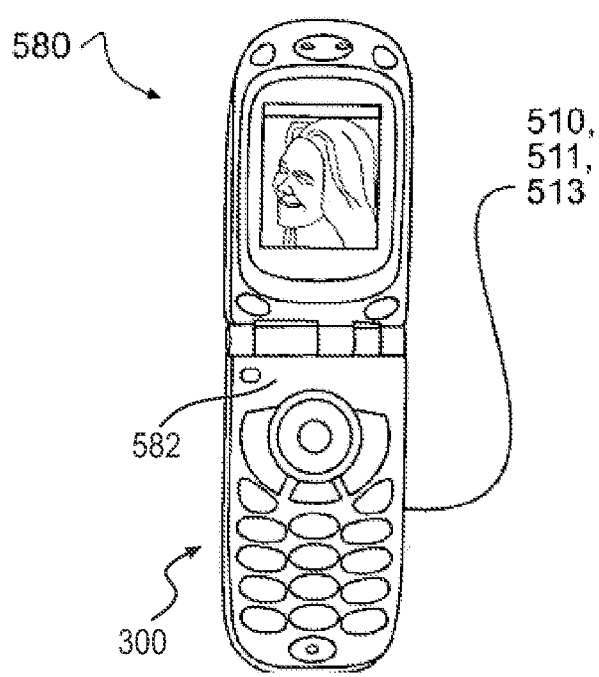
FIG. 32 is an example of an apparatus with sensors 582 based on FIG. 79 from the applicant's '916 application.

The smartphone or other device 580 can also be configured to control compartments implanted within (or attached to) the human body (or an animal body or plant), including examples such as FIGS. 29A & B or FIGS. 32A & B with multiple compartments like those previously shown for footwear, such as in FIGS. 11M-P, 11T-U, and 97-99A & B of the '665 patent application. Such implants or attachments can be configured to include one or more sensors 582 discussed previously. Similarly, the smartphone or other device 580 can be used to control compartments in the same way in body braces, padding, and armor, including in the examples shown in FIGS. 60A, 69, and 70 of the '930 patent application.

The computer or other device 580 including the example of a smartphone 580 can also be configured to include a microprocessor alone, including a system-on-a-chip (SoC), including a personal computer on a chip, and can also include a Faraday Cage 300, which can coincide with an outer compartment 500, such as the example shown in FIG. 23G of the '769 patent application. Especially because of privacy of data concerns, the smartphone or other device 580 or any Web site storing data therefrom can be configured to include any combination of security features indicated in the applicant's U.S. Pat. No. 398,403 filed Feb. 16, 2012, and published as Publication No. 20120311690 on Dec. 6, 2012 and in U.S. Pat. No. 10,684,657 filed Oct. 15, 2003 and published as Publication No. 2005/0180095 on Aug. 18, 2005, both of which applications are hereby incorporated by reference in their entirety in this application.

A smartphone or other mobile computer device, either general purpose or specialized, can comprise the following: the smartphone device can be configured to actively control the configuration of one or more bladders, compartments, chambers or internal sipes and one or more sensors located in either one or both of a sole or a removable inner sole insert of the footwear of the user and/or located in an apparatus worn or carried by the user, glued unto the user, or implanted in the user; and the one or more bladders, compartments, chambers, or sipes, and one or more sensors can be configured for computer control. Any of the components or methods of the example invention embodiments described in this paragraph can be combined with any other components or methods of the example invention embodiments described in previous paragraphs above or in the patents or applications incorporated by reference in this application.

The smartphone device can be configured to record a first test data set consisting of measurements by a sensor of the force and/or the relative pressure distribution of a wearer's foot sole on or near an upper surface of the wearer's footwear during the wearer's locomotion or other physical activity; the first test data set as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to record a first test data set consisting of measurements by a sensor of the relative motion during the user's locomotion or other physical activity of a position at or near to a part of the body of the user of the smartphone device; the first test data set as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to record a first test data set consisting of measurements of the relative motion during the user's locomotion or other physical activity of a position that is at or near the center of gravity of the body of the user of the smartphone device, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to establish a first configuration setting for the bladders, compartments, chambers, sipes or other portions of the apparatus or of either or both of the footwear soles. Any of the components or methods of the example invention embodiments described in this paragraph can be combined with any other components or methods of the example invention embodiments described in previous paragraphs above or in the patents or applications incorporated by reference in this application.

The first configuration setting of the smartphone device can be a neutral or baseline condition, including the condition wherein the smartphone device has not activated control of the apparatus or the footwear soles. Any of the components or methods of the example invention embodiments described in this paragraph can be combined with any other components or methods of the example invention embodiments described in previous paragraphs above or in the patents or applications incorporated by reference in this application.

The smartphone device can be configured to activate a second configuration setting for the bladders, compartments, chambers, sipes, or other portions of the apparatus or of either or both of the soles, the second configuration being different from the first configuration setting. Any of the components or methods of the example invention embodiments described in this paragraph can be combined with any other components or methods of the example invention embodiments described in previous paragraphs above or in the patents or applications incorporated by reference in this application.

Using the second configuration setting, the smartphone device can be configured to record a second test data set consisting of measurements of the relative motion during locomotion or other physical activity of the position at or near to the part of the user, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

Using the second configuration setting, the smartphone device can be configured to record a second test data set consisting of measurements of the relative motion during locomotion or other physical activity of the position at or near to the center of gravity of the user, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of relative motion during locomotion or other physical activity of the part of a model user or users, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of relative motion during locomotion or other physical activity of the position at or near to the part of a model user or users, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of relative motion during locomotion or other physical activity of the position at or near to the center of gravity of a model user or users, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to select the configuration setting of the footwear soles that produced the test data set that is the closest to the preferred data set and to reject the other configuration setting, thereby completing at least one full cycle of an operation to optimize the configuration for the wearer. Any of the components or methods of the example invention embodiments described in this paragraph can be combined with any other components or methods of the example invention embodiments described in previous paragraphs above or in the patents or applications incorporated by reference in this application.

The full cycle of the configuration optimizing operation can be repeated as frequently as necessary until the most recent test data set either closely matches the preferred data set or cannot be made to match the test data more closely. Any of the components or methods of the example invention embodiments described in this paragraph can be combined with any other components or methods of the example invention embodiments described in previous paragraphs above or in the patents or applications incorporated by reference in this application.

The full cycle of the configuration optimizing operation can be repeated hundreds or thousands or millions or billions of times. Any of the components or methods of the example invention embodiments described in this paragraph can be combined with any other components or methods of the example invention embodiments described in previous paragraphs above or in the patents or applications incorporated by reference in this application.

The model user or users can be chosen from a group of shod or barefoot users who have a history of low levels of overuse and/or acute injuries, the barefoot users including users that are distinguished by level of previous or current conventional footwear use, such as barefoot users that have been formerly shod and/or occasionally shod or seldom shod or never shod with conventional footwear. Any of the components or methods of the example invention embodiments described in this paragraph can be combined with any other components or methods of the example invention embodiments described in previous paragraphs above or in the patents or applications incorporated by reference in this application.

The smartphone device can be configured to include a gyroscope and an accelerometer. Any of the components or methods of the example invention embodiments described in this paragraph can be combined with any other components or methods of the example invention embodiments described in previous paragraphs above or in the patents or applications incorporated by reference in this application.

The smartphone device can be configured to include one or more wired connections and/or one or more wireless connections, the wireless connections including WiFi, Bluetooth, near field communications (NFC) and/or cellular. Any of the components or methods of the example invention embodiments described in this paragraph can be combined with any other components or methods of the example invention embodiments described in previous paragraphs above or in the patents or applications incorporated by reference in this application.

The relative motion can include geographic motion tracking between one or more geographic positions and said device is configured to include a global positioning system (GPS) components and/or another geographic location tracking capability. Any of the components or methods of the example invention embodiments described in this paragraph can be combined with any other components or methods of the example invention embodiments described in previous paragraphs above or in the patents or applications incorporated by reference in this application.

The smartphone device can be configured for wired and/or wireless connection to at least one peripheral device with at least one remote sensor located at or near to a body part of the user. Any of the components or methods of the example invention embodiments described in this paragraph can be combined with any other components or methods of the example invention embodiments described in previous paragraphs above or in the patents or applications incorporated by reference in this application.

The remote sensor can be of any known type, including motion, pressure, time, heat moisture, chemical, electrical, or electromagnetic sensor. At least one peripheral device can be a headphone set or a audio earplugs set or an earplugs set with at least one or two remote motion sensors. Any of the components or methods of the example invention embodiments described in this paragraph can be combined with any other components or methods of the example invention embodiments described in previous paragraphs above or in the patents or applications incorporated by reference in this application.

At least one peripheral device with at least one remote sensor can be configured to record and/or transmit a first and/or second test data set consisting of the measurements of the relative motion during locomotion or other physical activity of a position at or near to the body part of the user of the smartphone device, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The body part can be one or more of the smartphone device user's head, neck, shoulder, chest, cervical, thoracic or lumbar back, rib, elbow, wrist, hand, waist, sacrum, pubic bone, iliac crest, thigh, hip, knee, patella, shin bone or tibia, ankle, toe, forefoot, midfoot or heel of foot; or wherein the body part is part of the body of an animal or a portion of a plant. Any of the components or methods of the example invention embodiments described in this paragraph can be combined with any other components or methods of the example invention embodiments described in previous paragraphs above or in the patents or applications incorporated by reference in this application.

The remote sensor can be located in any practical location on any article of clothing or personal equipment, including earphones or earplugs, helmet, glasses, watch, belt, waistband, elastic underwear, armband, attached with tape or bandage, necklace or lanyard, cervical collar, ring, headband, in any manner attached or embedded in conventional or specialized clothing, or glued on the skin of the wearer. Any of the components or methods of the example invention embodiments described in this paragraph can be combined with any other components or methods of the example invention embodiments described in previous paragraphs above or in the patents or applications incorporated by reference in this application.

The at least one peripheral device with at least one remote sensor can transmit, in real time and/or later, the first and/or second data sets to the smartphone device and/or to another computer. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can include one or more or a multitude or 20 or 50 or 100 or 500 or 1000 or 4000 or 16,000 individual sensors. Any of the components or methods of the example invention embodiments described in this paragraph can be combined with any other components or methods of the example invention embodiments described in previous paragraphs above or in the patents or applications incorporated by reference in this application.

The locomotion can include walking and/or running. The test data sets can include at least a full stride or many strides of the walking and/or running locomotion or at least one full cycle or many cycles of any other repetitive motion of the user. The first and/or second test data sets can be collected when the locomotion occurs on a flat level surface, a flat uphill or upward inclining surface, or a flat downhill or downward inclining surface. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include at least a magnetorheological fluid located in the one or more bladders, compartments, chambers, sipes or other portions, the magnetorheological fluid being controlled at least in part or completely by the smartphone device. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include at least one valve located between the two or more bladders, compartments, chambers, sipes, or other portions, the at least one valve being controlled at least in part or completely by the smartphone device. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include at least one electric and/or electronic and/or electromechanical device that is controlled at least in part or completely by the smartphone device Any of the components or methods of the example invention embodiments described in this paragraph can be combined with any other components or methods of the example invention embodiments described in previous paragraphs above or in the patents or applications incorporated by reference in this application.

The apparatus and/or footwear sole or soles can include at least one battery and/or at least one device wherein the body weight and/or muscular energy of a wearer of the smartphone device is used to generate electrical power in the apparatus or either or both of the footwear soles. Any of the components or methods of the example invention embodiments described in this paragraph can be combined with any other components or methods of the example invention embodiments described in previous paragraphs above or in the patents or applications incorporated by reference in this application.

The apparatus or either or both of the footwear soles can be configured to include a wired and/or wireless connection to the smartphone device. Any of the components or methods of the example invention embodiments described in this paragraph can be combined with any other components or methods of the example invention embodiments described in previous paragraphs above or in the patents or applications incorporated by reference in this application.

An article of apparel or equipment can be configured to include wiring to connect the smartphone device to the apparatus and/or either or both of the footwear soles and/or one or more peripheral devices with at least one remote senor; and/or wherein the smartphone device is configured to provide power to the apparatus and/or footwear soles and/or peripheral devices. Any of the components or methods of the example invention embodiments described in this paragraph can be combined with any other components or methods of the example invention embodiments described in previous paragraphs above or in the patents or applications incorporated by reference in this application.

The smartphone device can be configured to actively control the configuration of one or more footwear soles of the user by altering the relative longitudinal height, including positive or negative heel lift (or drop), or negative or positive forefoot lift, and/or the relative side-to-side height between lateral and medial sides, and/or the relative height between the right and the left footwear, or a combination of these relative height alterations. These alterations are structurally and functionally like those performed typically by podiatrists and orthopedic specialists, for example. Any of the components or methods of the example invention embodiments described in this paragraph can be combined with any other components or methods of the example invention embodiments described in previous paragraphs above or in the patents or applications incorporated by reference in this application.

The smartphone device can be configured to actively control the configuration of one or more footwear soles of the user by altering the relative longitudinal firmness between heel area and forefoot area and/or side-to-side firmness between lateral and medial side areas, and/or the relative firmness between the right and the left footwear, or a combination of these relative firmness alterations. These alterations are structurally and functionally like those performed typically by podiatrists and orthopedic specialists, for example. Any of the components or methods of the example invention embodiments described in this paragraph can be combined with any other components or methods of the example invention embodiments described in previous paragraphs above or in the patents or applications incorporated by reference in this application.

The smartphone device can be configured to actively control the configuration of one or more footwear soles of the user by altering the relative height or firmness under one or more of the foot bones of the wearer, including under the calcaneus, the lateral calcaneal tuberosity, the base of the fifth metatarsal, the longitudinal arch, the metatarsal arch, each of the heads of the metatarsals, and each of the distal phalanges, including the hallux or big toe. These alterations are structurally and functionally like those performed typically by podiatrists and orthopedic specialists, for example. Any of the components or methods of the example invention embodiments described in this paragraph can be combined with any other components or methods of the example invention embodiments described in previous paragraphs above or in the patents or applications incorporated by reference in this application.

The smartphone device can be configured to actively control of the apparatus or footwear configuration at least once per full operation cycle or locomotion stride, many times per full operation cycle or locomotion stride, once per many full operation cycles or locomotion strides, or based on a set time period of any duration or based on another test condition. Any of the components or methods of the example invention embodiments described in this paragraph can be combined with any other components or methods of the example invention embodiments described in previous paragraphs above or in the patents or applications incorporated by reference in this application.

The device can be configured to record a first test data set consisting of measurements of the force and/or the relative pressure distribution of the wearer's foot sole on an upper surface of the footwear during the wearer's locomotion or other physical activity, as measured in at least one plane (1D) or in two planes (2D) or in three planes (3D) and/or including time or other measurements, the footwear upper surface including at least a multitude or 20 or 50 or 100 or 500 or 1,000 or 4,000, or 16,000 individual pressure sensors. Any of the components or methods of the example invention embodiments described in this paragraph can be combined with any other components or methods of the example invention embodiments described in previous paragraphs above or in the patents or applications incorporated by reference in this application.

Using the second configuration setting, the smartphone device can be configured to record a second test data set consisting of measurements of the force and/or the relative pressure distribution of the wearer's footsole on an upper surface of the footwear during the wearer's locomotion or other physical activity, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to compare the first test data set and the second test data set with a preferred data set for the measurements of force and/or relative pressure distribution of the foot sole of a model user or users on an upper surface of the footwear during the locomotion or other physical activity, as measured in at least one plane (1D) or in two planes (2D) or in three planes (3D) and/or including time or other measurements. Any of the components or methods of the example invention embodiments described in this paragraph can be combined with any other components or methods of the example invention embodiments described in previous paragraphs above or in the patents or applications incorporated by reference in this application.

The smartphone device can be configured to select the configuration setting of the soles that produced the test data set for the force or relative pressure distribution that is the closest to the preferred data set for relative pressure distribution and to reject the other configuration setting, thereby completing at least one full cycle of an operation to optimize the wearer's configuration. Any of the components or methods of the example invention embodiments described in this paragraph can be combined with any other components or methods of the example invention embodiments described in previous paragraphs above or in the patents or applications incorporated by reference in this application.

The optimizing operation can be used to reduce a range of pronation and/or supination of the wearer's foot and ankle during the landing phase of locomotion through active configuration by the smartphone device of the either or both of the footwear soles. Any of the components or methods of the example invention embodiments described in this paragraph can be combined with any other components or methods of the example invention embodiments described in previous paragraphs above or in the patents or applications incorporated by reference in this application.

The optimizing operation can be used by the smartphone device to actively configure either or both of the footwear soles or the apparatus in one or more or many areas of high and/or low pressure as measured on the upper surface of the footwear soles during the landing phase of locomotion or as measured on the outer surface of the apparatus during operation. Any of the components or methods of the example invention embodiments described in this paragraph can be combined with any other components or methods of the example invention embodiments described in previous paragraphs above or in the patents or applications incorporated by reference in this application.

The optimizing operation can be used by the smartphone device to actively configure either or both of the footwear soles or the apparatus to produce a forefoot strike, a midfoot strike, or a heel strike at the beginning of the landing phase during locomotion for either or both of the wearer's feet. Any of the components or methods of the example invention embodiments described in this paragraph can be combined with any other components or methods of the example invention embodiments described in previous paragraphs above or in the patents or applications incorporated by reference in this application.

The optimizing operation can be used by the smartphone device to actively configure either or both of the footwear soles or the apparatus to change the motion of the center of force on the surface of footwear for either or both of the wearer's feet during locomotion. Any of the components or methods of the example invention embodiments described in this paragraph can be combined with any other components or methods of the example invention embodiments described in previous paragraphs above or in the patents or applications incorporated by reference in this application.

Other test data sets can potentially be monitored, recorded, processed and/or transmitted by the smartphone device or remote sensor or sensors, such as blood pressure, heart rate, respiration rate, blood sugar level, weight, body temperature (core or a body part), ambient temperature, or any other body or body part measurement, medical or other, or audio or video. Any of the components or methods of the example invention embodiments described in this paragraph can be combined with any other components or methods of the example invention embodiments described in previous paragraphs above or in the patents or applications incorporated by reference in this application.

One or more of the test data sets can be transmitted to a cloud system for storage and/or shared or independent processing and/or analysis of groups or categories of users and/or shared access by permitted third parties and by the user. Any of the components or methods of the example invention embodiments described in this paragraph can be combined with any other components or methods of the example invention embodiments described in previous paragraphs above or in the patents or applications incorporated by reference in this application.

One or more of the test data sets can be transmitted to a web site for storage and/or processing and/or analysis of groups or categories of users and/or shared access by the user and by third parties permitted by the user. Any of the components or methods of the example invention embodiments described in this paragraph can be combined with any other components or methods of the example invention embodiments described in previous paragraphs above or in the patents or applications incorporated by reference in this application.

The smartphone device can be used to measure the relative positions to each other of a user's right and left feet during the stance phase of locomotion so as to determine the degree of crossover of right and/or left feet across the centerline of the user's body, as measured in the frontal plane during the stance phase of locomotion; and then to test a series of configuration settings in order to reduce or eliminate the crossover. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool for diagnostic, therapeutic, and/or rehabilitative functions before and/or during and/or after surgical or other medical treatment. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool for medical treatment functions through non-surgical means. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a podiatric system or a podiatric tool for diagnostic, therapeutic, and/or rehabilitative functions before and/or during and/or after surgical or other podiatric treatment. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool to stimulate or retard structural bone growth and/or joint development in a child wearer prior to adulthood through non-surgical means. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool to prevent or reduce the gradual deterioration of bone and/or joint structure in an adult wearer through non-surgical means. Any of the components or methods of the example invention embodiments described in this paragraph can be combined with any other components or methods of the example invention embodiments described in previous paragraphs above or in the patents or applications incorporated by reference in this application.

The smartphone device and/or the apparatus and/or the footwear and/or the peripheral devices with sensors can be used as a medical system or a medical tool to treat the deterioration of bone and/or joint structure in an elderly wearer through non-surgical means. Any of the components or methods of the example invention embodiments described in this paragraph can be combined with any other components or methods of the example invention embodiments described in previous paragraphs above or in the patents or applications incorporated by reference in this application.

The smartphone device can be worn at the centerline of the rearmost portion of the wearer's belt or otherwise attached at or near the small of the wearer's lumbar back, centered between and at about the level of the illiac crests. Any of the components or methods of the example invention embodiments described in this paragraph can be combined with any other components or methods of the example invention embodiments described in previous paragraphs above or in the patents or applications incorporated by reference in this application.

The apparatus can be a helmet and/or helmet padding and/or other padding or protective gear, including braces, with one or more bladders, compartments, chambers, sipes, or other portions that are actively configured by the smartphone device. Any of the components or methods of the example invention embodiments described in this paragraph can be combined with any other components or methods of the example invention embodiments described in previous paragraphs above or in the patents or applications incorporated by reference in this application.

The footwear can be configured so that any part of or all of the configurable components of the footwear are located in a removable or fixed insert or a removable or fixed orthotic. Any of the components or methods of the example invention embodiments described in this paragraph can be combined with any other components or methods of the example invention embodiments described in previous paragraphs above or in the patents or applications incorporated by reference in this application.

One or both of a wearer's footwear can be configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent 44 of one or both sides of the sole. Any of the components or methods of the example invention embodiments described in this paragraph can be combined with any other components or methods of the example invention embodiments described in previous paragraphs above or in the patents or applications incorporated by reference in this application.

One or both of a wearer's concavely rounded footwear can be configured to deform under the pressure of the wearer's body weight so as to flatten the rounding against the flat surface of the ground, in just the same way that rounded portions of the wearer's foot sole flatten against the flat surface of the ground. Any of the components or methods of the example invention embodiments described in this paragraph can be combined with any other components or methods of the example invention embodiments described in previous paragraphs above or in the patents or applications incorporated by reference in this application.

One or both of a wearer's footwear can be configured to include a sole which has a toe end portion and a heel end portion that have concavely rounded upper and lower surfaces relative to the position of the intended wearer's foot sole, as measured in at least in a sagittal plane cross-section taken along the long axis of the footwear; and/or wherein the upper and lower surfaces can be substantially parallel; and/or wherein the concavely rounded lower surface can extend to the most anterior extent and/or posterior extent of the sole; and/or one or both of a wearer's footwear can be configured to include a flat portion between the toe end portion and heel end portion, as measured in at least in a sagittal plane cross-section taken along the long axis of the footwear. Any of the components or methods of the example invention embodiments described in this paragraph can be combined with any other components or methods of the example invention embodiments described in previous paragraphs above or in the patents or applications incorporated by reference in this application.

One or both sides of the sole can have at least one flexibility groove located in the midfoot of the footwear sole proximate to a flexibility axis 122 located at about the posterior of the forefoot of the footwear sole and anterior to a position proximate to the base of the fifth metatarsal of the intended wearer's foot sole; and/or the flexibility grove can extend through part or all of the underneath portion between the sides of the footwear sides; and/or the footwear sole has other flexibility grooves. Any of the components or methods of the example invention embodiments described in this paragraph can be combined with any other components or methods of the example invention embodiments described in previous paragraphs above or in the patents or applications incorporated by reference in this application.

One or both of a wearer's concavely rounded footwear soles can be formed from a flat sheet of heat and/or pressure-sensitive plastic and/or rubber, including foamed or blown, the flat sheet being put under heat and/or pressure by a press 55 with upper and lower surfaces configured to produce the concavely rounded footwear sole; and/or the footwear sole can be configured to include at least two layers that are laminated together with heat and/or pressure sensitive glue; and/or at least a part or all of the footwear sole can be formed using a mold. Any of the components or methods of the example invention embodiments described in this paragraph can be combined with any other components or methods of the example invention embodiments described in previous paragraphs above or in the patents or applications incorporated by reference in this application.

One or both of a wearer's footwear sole can be configured to have at least a semi-thong 3 positioned to be located between the big toe and second toe of the intended wearer's foot; the semi-thong can be fixed, fastened, or embedded in only to the upper surface and/or other portions of the footwear sole and can be not fixed to and/or contacting a portion of the footwear upper or straps; and/or optional semi-thongs positioned can be to be located between one or more or all of the other toes of the wearer's foot sole; and/or the semi-thong can have a round, an oval, or an anthropomorphically-determined shape, as viewed in a horizontal cross-section; and/or the semi-thong can be constructed of plastic and/or rubber, including foamed or blown; and/or the semi-thong can be configured to have at least one softer material on the outer surface and a core of at least one firmer material inside; and/or the semi-thong can be configured to form a portion of the bottom surface the footwear sole; and/or the semi-thong can be configured to be temporarily fastened to at least a portion of the footwear upper or strap; and/or wherein the semi-thong can have a strut extending forward between the toes that serves as a protective partition between the toes. Any of the components or methods of the example invention embodiments described in this paragraph can be combined with any other components or methods of the example invention embodiments described in previous paragraphs above or in the patents or applications incorporated by reference in this application.

One or both of a wearer's most minimalist footwear can be a footwear sole and/or a sock that is configured to include only a fabric layer, a traction coating layer on the outer surface of the fabric, and a traction coating layer on the inner surface of the fabric; and/or wherein the coating layers can be rubber and/or plastic, including foamed and/or blown; and/or wherein one or both of the coating layers can be continuous or formed in a geometric or other pattern or randomly oriented and/or irregularly shaped; and/or the minimalist footwear can be configured to include a midsole insert and/or orthotic; and/or wherein one or both of a wearer's most minimalist footwear can be a footwear sole and/or a sock that is configured to include only the fabric, which is fabricated with a thread coated with a traction coating layer. Any of the components or methods of the example invention embodiments described in this paragraph can be combined with any other components or methods of the example invention embodiments described in previous paragraphs above or in the patents or applications incorporated by reference in this application.

One or both of a wearer's most minimalist footwear can be a footwear sole and/or a sock that can be configured to include at least one fabric layer, at least one traction coating layer on the outer surface of the fabric, and at least one traction coating layer on the inner surface of the fabric; and/or wherein the coating layers can be rubber and/or plastic, including foamed and/or blown; and/or wherein one or both of the coating layers can be continuous or formed in a geometric or other pattern or randomly can be oriented and/or irregularly shaped; and/or the minimalist footwear can be configured to include a midsole insert and/or orthotic; and/or wherein the fabric can be fabricated with a thread coated with a traction coating layer. Any of the components or methods of the example invention embodiments described in this paragraph can be combined with any other components or methods of the example invention embodiments described in previous paragraphs above or in the patents or applications incorporated by reference in this application.

The smartphone device or apparatus can be configured to include an outer coating of Teflon™. Any of the components or methods of the example invention embodiments described in this paragraph can be combined with any other components or methods of the example invention embodiments described in previous paragraphs above or in the patents or applications incorporated by reference in this application.

A software app can configure at least a portion of a part or all of the configuration of a smartphone device and/or one or more sensors and/or one or both footwear and/or one or more apparatus. Any of the components or methods of the example invention embodiments described in this paragraph can be combined with any other components or methods of the example invention embodiments described in previous paragraphs above or in the patents or applications incorporated by reference in this application.

A sole and/or a removable inner sole insert for footwear can comprise the following: one or more bladders, compartments, chambers, internal sipes or other portions located in the sole and/or in a removable insert; one or more sensors located in or on the sole and/or in the removable sole insert and/or located in or on an insole; the one or more bladders, compartments, chambers, sipes or other portions and the one or more sensors can be configured for control by a smartphone or other mobile computer device, general purpose or specialized; and/or the control can be conducted through a wired or a wireless connection. In addition, one or both of a wearer's footwear and/or the removable inner sole insert for footwear can be configured to include a sole which has concavely rounded upper and lower surfaces relative to the intended wearer's foot sole, as measured in at least in a frontal plane cross-section taken in the heel area, the forefoot, and in the midfoot area; and/or the upper and lower surfaces can be substantially parallel; and/or the concavely rounded lower surface can extend to the lateral extent 44 of one or both sides of the sole; and/or the lateral extent 44 can extend above the lowest point of the inner footwear surface. Any of the components or methods of the example invention embodiments described in this paragraph can be combined with any other components or methods of the example invention embodiments described in previous paragraphs above or in the patents or applications incorporated by reference in this application.

A sole and/or a removable inner sole insert for footwear for footwear can comprise the following: one or both of a wearer's footwear can be configured to include a sole and/or the removable inner sole insert which has concavely rounded upper and lower surfaces relative to the intended wearer's foot sole, as measured in at least in a frontal plane cross-section taken in the heel area, the forefoot, and in the midfoot area; and/or the upper and lower surfaces can be substantially parallel; and/or the concavely rounded lower surface can extend to the lateral extent 44 of one or both sides of the sole; and/or the lateral extent 44 can extend above the lowest point of the inner footwear surface. Any of the components or methods of the example invention embodiments described in this paragraph can be combined with any other components or methods of the example invention embodiments described in previous paragraphs above or in the patents or applications incorporated by reference in this application.

A sole and/or a removable sole insert for footwear can comprise the following: one or both of a wearer's footwear sole and/or the removable sole insert can be configured to have at least a semi-thong 3 positioned to be located between the big toe and second toe of the intended wearer's foot; the semi-thong can be fixed, fastened, or embedded in only to the upper surface and/or other portions of the footwear sole and can be not fixed to and/or contacting a portion of the footwear upper or straps; and/or optional semi-thongs can be positioned to be located between one or more or all of the other toes of the wearer's foot sole; and/or the semi-thong can have a round, an oval, or an anthropomorphically-determined shape, as viewed in a horizontal cross-section; and/or the semi-thong can be constructed of plastic and/or rubber, including foamed or blown; and/or the semi-thong can be configured to have at least one softer material on the outer surface and a core of at least one firmer material inside; and/or the semi-thong can be configured to form a portion of the bottom surface the footwear sole; and/or the semi-thong can be configured to be temporarily fastened to at least a portion of the footwear upper or strap; and/or wherein the semi-thong can have a strut extending forward between the toes that serves as a protective partition between the toes. One or both of a wearer's footwear can be configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces can be substantially parallel; and/or wherein the concavely rounded lower surface can extend to the lateral extent 44 of one or both sides of the sole. Any of the components or methods of the example invention embodiments described in this paragraph can be combined with any other components or methods of the example invention embodiments described in previous paragraphs above or in the patents or applications incorporated by reference in this application.

A sole can comprise the following: one or both of a wearer's most minimalist footwear can be a footwear sole and/or a sock that can be configured to include only a fabric layer, a traction coating layer on the outer surface of the fabric, and a traction coating layer on the inner surface of the fabric; and/or wherein the coating layers can be a rubber and/or plastic, including foamed and/or blown; and/or wherein one or both of the coating layers can be continuous or formed in a geometric or other pattern or randomly oriented and/or irregularly shaped; and/or the minimalist footwear can be configured to include a midsole insert and/or orthotic; and/or wherein one or both of a wearer's most minimalist footwear can be a footwear sole and/or a sock that is configured to include only the fabric, which can be fabricated with a thread coated with a traction coating layer; and/or the sole is configure to allow for a removable sole insert as discussed at least in the several preceding three paragraphs. Any of the components or methods of the example invention embodiments described in this paragraph can be combined with any other components or methods of the example invention embodiments described in previous paragraphs above or in the patents or applications incorporated by reference in this application.

A sole can comprise the following: one or both of a wearer's most minimalist footwear can be a footwear sole and/or a sock that can be configured to include at least one fabric layer, at least one traction coating layer on the outer surface of the fabric, and at least one traction coating layer on the inner surface of the fabric; and/or wherein the coating layers can be rubber and/or plastic, including foamed and/or blown; and/or wherein one or both of the coating layers can be continuous or formed in a geometric or other pattern or randomly oriented and/or irregularly shaped; and/or the minimalist footwear can be configured to include a midsole insert and/or orthotic; and/or wherein the fabric can be fabricated with a thread coated with a traction coating layer; and/or the sole can be configured to allow for a removable sole insert as discussed above. Any of the components or methods of the example invention embodiments described in this paragraph can be combined with any other components or methods of the example invention embodiments described in previous paragraphs above or in the patents or applications incorporated by reference in this application.

An apparatus can comprise the following: one or more bladders, compartments, chambers, sipes or other portions can be located in the apparatus; one or more sensors can be located in or on the apparatus; the one or bladders, compartments, chambers, sipes or other portions and the one or more sensors being configured for control by a smartphone or other mobile computer device, general purpose or specialized; and/or the control can be conducted through a wired or a wireless connection. The apparatus can be configured to operate with and/or be controlled by the smartphone device as described in detail above. Any of the components or methods of the example invention embodiments described in this paragraph can be combined with any other components or methods of the example invention embodiments described in previous paragraphs above or in the patents or applications incorporated by reference in this application.

An article of apparel or equipment can comprise the following: the article of apparel or equipment can be configured to include wiring to connect the smartphone device to the apparatus and/or either or both of the footwear soles and/or one or more peripheral devices with at least one remote senor; and/or wherein the smartphone device can be configured to provide power to the apparatus and/or footwear soles and/or peripheral devices. Any of the components or methods of the example invention embodiments described in this paragraph can be combined with any other components or methods of the example invention embodiments described in previous paragraphs above or in the patents or applications incorporated by reference in this application.

A helmet, including faceguard and/or chinguard, or other protective equipment including braces and body armor can be configured to comprise an outer coating of Teflon™ 304 to reduce rotational forces such as on the head. Even a smartphone device or an apparatus can usefully be configured to comprise an outer coating of Teflon™ 304 to reduce forces when positioned inside a protective case; alternatively, a case or other protective device for a smartphone device or tablet or other electronic device can be configured to comprise an outer coating of Teflon™ to reduce tangential impact forces.

This application incorporates by reference in their entirety the following published U.S. patent and patent applications: U.S. Pat. No. 5,317,819 issued Jun. 7, 1994; U.S. Pat. No. 5,813,142 issued Sep. 29, 2998 to Ronald S. Demon; U.S. Pat. No. 5,909,948 issued Jun. 8, 1999; U.S. Pat. No.

6,163,982 issued Dec. 26, 2000; application Ser. No. 11/282,665 published Nov. 9, 2006 as Pub. No. 2006/0248749 A1; application Ser. No. 11/802,930 published Apr. 17, 2008 as Pub. No. US 2008/0086916 A1; application Ser. No. 11/190,087 published Feb. 26, 2008 as U.S. Pat. No. 7,334,350 B2; and application Ser. No. 12/292,769 published on Aug. 13, 2009 as Pub. No. US 2009/0200661 A1. The publication cover pages of the '948, '350 patent and the '665, '930, and '769 patent applications are also included with this application at the end to confirm the specific and explicit incorporation by reference of these four documents.

More specifically incorporated by reference are at least the following figures and the textual specification associated with the figures: FIGS. 9-12 of the '948 patent; FIGS. 1C, 15, 16, 17A & B, 29A & B, 32A & B, 44, 59, 60, 61A & B, 69, 70, and 79 of the '930 U.S. patent application; FIGS. 11M, 11N, 11O, and 11P of the '350 U.S. patent; FIGS. 11M, 11N, 11O, 11P, 11T, 11U, 63, 97, 98, and 99A & B of the '665 U.S. patent application; and FIG. 23G of the '769 U.S. patent application. Copies of these figures are also included in this application.

The applicant claims the right to priority based on U. S. Provisional patent applications previously filed.

The applicant's other footwear U.S. Pat. Nos. 4,989,349; 5,317,819; 5,544,429; 5,909,948; 6,115,941; 6,115,945; 6,163,982; 6,308,439; 6,314,662; 6,295,744; 6,360,453; 6,487,795; 6,584,706; 6,591,519; 6,609,312; 6,629,376; 6,662,470; 6,675,498; 6,675,499; 6,708,424; 6,729,046; 6,748,674; 6,763,616; 6,789,331; 6,810,606; 6,877,254; 6,918,197; 7,010,869; 7,082,697; 7,093,379; 7,127,834; 7,168,185; and 7,174,658 are hereby incorporated by reference herein in their entirety into this application for completeness of disclosure of the applicant's novel and useful combination of one or more of any of the features or components of any of the figures of this application with one or more of any of the features of any one or more of the preceding applicant's patents listed above in this paragraph.

The applicant's other footwear published U.S. application Numbers 20020000051; 20020007571; 20020007572; 20020014020; 20020014021; 20020023373; 20020073578; 20020116841; 20030046830; 20030070320; 20030079375; 20030131497; 20030208926; 20030217482; 20040134096; 20040250447; 20050016020; 20050086837; 20050217143; and 20060032086 are hereby incorporated by reference herein in their entirety into this application for completeness of disclosure of the applicant's novel and useful combination of one or more of any of the features or components of any of the figures of this application with one or more of any of the features of any one or more of the preceding applicant's published U.S. applications listed above in this paragraph.

The preceding novel methods, apparatus and software for computers including for a computer including a smartphone and other related devices and for peripheral devices with sensors to be used with said computers.

A. A smartphone or other mobile computer device, general purpose or specialized, comprising: the smartphone device is configured to actively control the configuration of one or more bladders, compartments, chambers or internal sipes and one or more sensors located in either one or both of a sole or a removable inner sole insert of the footwear of the user and/or located in an apparatus worn or carried by the user, glued unto the user, or implanted in the user; and the one or more bladders, compartments, chambers, or sipes, and one or more sensors being configured for computer control.

B. The smartphone device of paragraph A, wherein the device is configured to record a first test data set consisting of measurements by a sensor of the force and/or relative pressure distribution of a wearer's foot-sole on or near an upper surface of the wearer's footwear during the wearer's locomotion or other physical activity; the first test data set as measured in at least one plane (1D) or in two planes (2D) or in three planes (3D) and/or including time or other measurements.

C. The smartphone device of any one of paragraphs A-B, wherein the device is configured to record a first test data set consisting of measurements by a sensor of the relative motion during the user's locomotion or other physical activity of a position at or near to a part of the body of the user of the smartphone device; the first test data set as measured in at least one plane (1D) or in two planes (2D) or in three planes (3D) and/or including time or other measurements.

D. The smartphone device of any one of paragraphs A-C, wherein the device is configured to record a first test data set consisting of measurements of the relative motion during the user's locomotion or other physical activity of a position that is at or near the center of gravity of the body of the user of the smartphone device, as measured in at least one plane (1D) or in two planes (2D) or in three planes (3D) and/or including time or other measurements.

E. The smartphone device of any one of paragraphs A-D, wherein the smartphone device is configured to establish a first configuration setting for the bladders, compartments, chambers, sipes or other portions of the apparatus or of either or both of the footwear soles.

F. The smartphone device of any one of paragraphs A-E, wherein the first configuration setting is a neutral or baseline condition, including the condition wherein the smartphone device has not activated control of the apparatus or the footwear soles.

G. The smartphone device of any one of paragraphs A-F, wherein the smartphone device is configured to activate a second configuration setting for the bladders, compartments, chambers, sipes, or other portions of the apparatus or of either or both of the soles, the second configuration being different from the first configuration setting.

H. The smartphone device of any one of paragraphs A-G, wherein using the second configuration setting, the smartphone device is configured to record a second test data set consisting of measurements of the relative motion during locomotion or other physical activity of the position at or near to the part of the user, as measured in at least one plane (1D) or in two planes (2D) or in three planes (3D) and/or including time or other measurements.

I. The smartphone device of any one of paragraphs A-H, wherein using the second configuration setting, the smartphone device is configured to record a second test data set consisting of measurements of the relative motion during locomotion or other physical activity of the position at or near to the center of gravity of the user, as measured in at least one plane (1D) or in two planes (2D) or in three planes (3D) and/or including time or other measurements.

J. The smartphone device of any one of paragraphs A-I, wherein the smartphone device is configured to compare the first test data set and the second test data set with a preferred data set for the measurements of relative motion during locomotion or other physical activity of the part of a model user or users, as measured in at least one plane (1D) or in two planes (2D) or in three planes (3D) and/or including time or other measurements.

K. The smartphone device of any one of paragraphs A-J, wherein the smartphone device is configured to compare the first test data set and the second test data set with a preferred data set for the measurements of relative motion during locomotion or other physical activity of the position at or near to the part of a model user or users, as measured in at least one plane (1D) or in two planes (2D) or in three planes (3D) and/or including time or other measurements.

L. The smartphone device of any one of paragraphs A-K, wherein the smartphone device is configured to compare the first test data set and the second test data set with a preferred data set for the measurements of relative motion during locomotion or other physical activity of the position at or near to the center of gravity of a model user or users, as measured in at least one plane (1D) or in two planes (2D) or in three planes (3D) and/or including time or other measurements.

M. The smartphone device of any one of paragraphs A-L, wherein the smartphone device is configured to select the configuration setting of the footwear soles that produced the test data set that is the closest to the preferred data set and to reject the other configuration setting, thereby completing at least one full cycle of an operation to optimize the configuration for the wearer.

N. The smartphone device of any one of paragraphs A-M, wherein the full cycle of the configuration optimizing operation is repeated as frequently as necessary until the most recent test data set either closely matches the preferred data set or cannot be made to match the test data more closely.

O. The smartphone device of any one of paragraphs A-N, wherein the full cycle of the configuration optimizing operation is repeated hundreds or thousands or millions or billions of times.

P. The smartphone device of any one of paragraphs A-O, wherein the model user or users are chosen from a group of shod or barefoot users who have a history of low levels of overuse and/or acute injuries, the barefoot users including users that are distinguished by level of previous or current conventional footwear use, such as barefoot users that have been formerly shod and/or occasionally shod or seldom shod or never shod with conventional footwear.

Q. The smartphone device of any one of paragraphs A-P, wherein the smartphone device is configured to include a gyroscope and an accelerometer.

R. The smartphone device of any one of paragraphs A-Q, wherein the smartphone device is configured to include one or more wired connections and/or one or more wireless connections, the wireless connections including WiFi, Bluetooth, near field communications (NFC) and/or cellular.

S. The smartphone device of any one of paragraphs A-R, wherein the relative motion includes geographic motion tracking between one or more geographic positions and said device is configured to include a global positioning system (GPS) components and/or another geographic location tracking capability.

T. The smartphone device of any one of paragraphs A-S, wherein the smartphone device is configured for wired and/or wireless connection to at least one peripheral device with at least one remote sensor located at or near to a body part of the user.

U. The smartphone device of any one of paragraphs A-T, wherein the remote sensor is of any known type, including motion, pressure, time, heat moisture, chemical, electrical, or electromagnetic sensor.

V. The smartphone device of any one of paragraphs A-U, wherein the at least one peripheral device is a headphone set or a audio earplugs set or an earplugs set with at least one or two remote motion sensors.

W. The smartphone device of any one of paragraphs A-V, wherein the at least one peripheral device with at least one remote sensor is configured to record and/or transmit a first and/or second test data set consisting of the measurements of the relative motion during locomotion or other physical activity of a position at or near to the body part of the user of the smartphone device, as measured in at least one plane (1D) or in two planes (2D) or in three planes (3D) and/or including time or other measurements.

X. The smartphone device of any one of paragraphs A-W, wherein the body part is one or more of the smartphone device user's head, neck, shoulder, chest, cervical, thoracic or lumbar back, rib, elbow, wrist, hand, waist, sacrum, pubic bone, illiac crest, thigh, hip, knee, patella, shin bone or tibia, ankle, toe, forefoot, midfoot or heel of foot; or wherein the body part is part of the body of an animal or a portion of a plant.

Y. The smartphone device of any one of paragraphs A-X, wherein the remote sensor is located in any practical location on any article of clothing or personal equipment, including earphones or earplugs, helmet, glasses, watch, belt, waistband, elastic underwear, armband, attached with tape or bandage, necklace or lanyard, cervical collar, ring, headband, in any manner attached or embedded in conventional or specialized clothing, or glued on the skin of the wearer.

Z. The smartphone device of any one of paragraphs A-Y, wherein the at least one peripheral device with at least one remote sensor transmits, in realtime and/or later, the first and/or second data sets to the smartphone device and/or to another computer.

AA. The smartphone device of any one of paragraphs A-Z, wherein the apparatus or either or both of the footwear soles include one or more or a multitude or 20 or 50 or 100 or 500 or 1000 or 4000 or 16,000 individual sensors.

BB. The smartphone device of any one of paragraphs A-Z and AA, wherein the locomotion includes walking and/or running.

CC. The smartphone device of any one of paragraphs A-Z and AA-BB, wherein the test data sets include at least a full stride or many strides of the walking and/or running locomotion or at least one full cycle or many cycles of any other repetitive motion of the user.

DD. The smartphone device of any one of paragraphs A-Z and AA-CC, wherein the first and/or second test data sets are collected when the locomotion occurs on a flat level surface, a flat uphill or upward inclining surface, or a flat downhill or downward inclining surface.

EE. The smartphone device of any one of paragraphs A-Z and AA-DD, wherein the apparatus or either or both of the footwear soles are configured to include at least a magnetorheological fluid located in the one or more bladders, compartments, chambers, sipes or other portions, the magnetorheological fluid being controlled at least in part or completely by the smartphone device.

FF. The smartphone device of any one of paragraphs A-Z and AA-EE, wherein the apparatus or either or both of the footwear soles are configured to include at least one valve located between the two or more bladders, compartments, chambers, sipes, or other portions, the at least one valve being controlled at least in part or completely by the smartphone device.

GG. The smartphone device of any one of paragraphs A-Z and AA-FF, wherein the apparatus or either or both of the footwear soles are configured to include at least one electric and/or electronic and/or electromechanical device that is controlled at least in part or completely by the smartphone device.

HH. The smartphone device of any one of paragraphs A-Z and AA-GG, wherein at least one battery and/or at least one device wherein the body weight and/or muscular energy of a wearer of the smartphone device is used to generate electrical power in the apparatus or either or both of the footwear soles.

II. The smartphone device of any one of paragraphs A-Z and AA-HH, wherein the apparatus or either or both of the footwear soles are configured to include a wired and/or wireless connection to the smartphone device.

JJ. The smartphone device of any one of paragraphs A-Z and AA-II, wherein an article of apparel or equipment is configured to include wiring to connect the smartphone device to the apparatus and/or either or both of the footwear soles and/or one or more peripheral devices with at least one remote senor; and/or wherein the smartphone device is configured to provide power to the apparatus and/or footwear soles and/or peripheral devices.

KK. The smartphone device of any one of paragraphs A-Z and AA-JJ, wherein the smartphone device is configured to actively control the configuration of one or more footwear soles of the user by altering the relative longitudinal height, including positive or negative heel lift, or negative or positive forefoot lift, and/or the relative side-to-side height between lateral and medial sides, and/or the relative height between the right and the left footwear soles, or a combination of these relative height alterations.

LL. The smartphone device of any one of paragraphs A-Z and AA-KK, wherein the smartphone device is configured to actively control the configuration of one or more footwear soles of the user by altering the relative longitudinal firmness between heel area and forefoot area and/or side-to-side firmness between lateral and medial side areas, and/or the relative firmness between the right and the left footwear soles, or a combination of these relative firmness alterations.

MM. The smartphone device of any one of paragraphs A-Z and AA-LL, wherein the smartphone device is configured to actively control the configuration of one or more footwear soles of the user by altering the relative height or firmness under one or more of the foot bones of the wearer, including under the calcaneus, the lateral calcaneal tuberosity, the base of the fifth metatarsal, the longitudinal arch, the metatarsal arch, each of the heads of the metatarsals, and each of the distal phalanges, including the hallux or big toe.

NN. The smartphone device of any one of paragraphs A-Z and AA-MM, wherein the smartphone device is configured to actively control of the apparatus or footwear configuration at least once per full operation cycle or locomotion stride, many times per full operation cycle or locomotion stride, once per many full operation cycles or locomotion strides, or based on a set time period of any duration or based on another test condition.

OO. The smartphone device of any one of paragraphs A-Z and AA-NN, wherein the device is configured to record a first test data set consisting of measurements of the force and/or the relative pressure distribution of the wearer's footsole on an upper surface of the footwear during the wearer's locomotion or other physical activity, as measured in at least one plane (1D) or in two planes (2D) or in three planes (3D) and/or including time or other measurements, the footwear upper surface including at least a multitude or 20 or 50 or 100 or 500 or 1,000 or 4,000, or 16,000 individual pressure sensors.

PP. The smartphone device of any one of paragraphs A-Z and AA-OO, wherein using the second configuration setting, the smartphone device is configured to record a second test data set consisting of measurements of the force and/or the relative pressure distribution of the wearer's footsole on an upper surface of the footwear during the wearer's locomotion or other physical activity, as measured in at least one plane (1D) or in two planes (2D) or in three planes (3D) and/or including time or other measurements.

QQ. The smartphone device of any one of paragraphs A-Z and AA-PP, wherein the smartphone device is configured to compare the first test data set and the second test data set with a preferred data set for the measurements of force and/or relative pressure distribution of the foot sole of a model user or users on an upper surface of the footwear during the locomotion or other physical activity, as measured in at least one plane (1D) or in two planes (2D) or in three planes (3D) and/or including time or other measurements.

RR. The smartphone device of any one of paragraphs A-Z and AA-QQ, wherein the smartphone device is configured to select the configuration setting of the soles that produced the test data set for the force or relative pressure distribution that is the closest to the preferred data set for relative pressure distribution and to reject the other configuration setting, thereby completing at least one full cycle of an operation to optimize the wearer's configuration.

SS. The smartphone device of any one of paragraphs A-Z and AA-RR, wherein the optimizing operation is used to reduce a range of pronation and/or supination of the wearer's foot and ankle during the landing phase of locomotion through active configuration by the smartphone device of the either or both of the footwear soles.

TT. The smartphone device of any one of paragraphs A-Z and AA-SS, wherein the optimizing operation is used by the smartphone device to actively configure either or both of the footwear soles or the apparatus in one or more or many areas of high and/or low pressure as measured on the upper surface of the footwear soles during the landing phase of locomotion or as measured on the outer surface of the apparatus during operation.

UU. The smartphone device of any one of paragraphs A-Z and AA-TT, wherein the optimizing operation is used by the smartphone device to actively configure either or both of the footwear soles or the apparatus to produce a forefoot strike, a midfoot strike, or a heel strike at the beginning of the landing phase during locomotion for either or both of the wearer's feet.

VV. The smartphone device of any one of paragraphs A-Z and AA-UU, wherein the optimizing operation is used by the smartphone device to actively configure either or both of the footwear soles or the apparatus to change the motion of the center of force on the surface of footwear for either or both of the wearer's feet during locomotion.

WW. The smartphone device of any one of paragraphs A-Z and AA-VV, wherein other test data sets can potentially be monitored, recorded, processed and/or transmitted by the smartphone device or remote sensor or sensors, such as blood pressure, heart rate, respiration rate, blood sugar level, weight, body temperature (core or a body part), ambient temperature, or any other body or body part measurement, medical or other, or audio or video.

XX. The smartphone device of any one of paragraphs A-Z and AA-WW, wherein one or more of the test data sets are transmitted to a cloud system for storage and/or shared or independent processing and/or analysis of groups or categories of users and/or shared access by permitted third parties and by the user.

YY. The smartphone device of any one of paragraphs A-Z and AA-XX, wherein one or more of the test data sets are transmitted to a web site for storage and/or processing and/or analysis of groups or categories of users and/or shared access by the user and by third parties permitted by the user.

ZZ. The smartphone device of any one of paragraphs A-Z and AA-YY, wherein the smartphone device is used to measure the relative positions to each other of a user's right and left feet during the stance phase of locomotion so as to determine the degree of crossover of right and/or left feet across the centerline of the user's body, as measured in the frontal plane during the stance phase of locomotion; and then to test a series of configuration settings in order to reduce or eliminate the crossover.

AAA. The smartphone device of any one of paragraphs A-Z and AA-ZZ, wherein the smartphone device and/or the apparatus and/or the footwear and/or the peripheral devices with sensors are used as a medical system or a medical tool for diagnostic, therapeutic, and/or rehabilitative functions before and/or during and/or after surgical or other medical treatment.

BBB. The smartphone device of any one of paragraphs A-Z and AA-ZZ and AAA, wherein the smartphone device and/or the apparatus and/or the footwear and/or the peripheral devices with sensors are used as a medical system or a medical tool for medical treatment functions through non-surgical means.

CCC. The smartphone device of any one of paragraphs A-Z and AA-ZZ and AAA-BBB, wherein the smartphone device and/or the apparatus and/or the footwear and/or the peripheral devices with sensors are used as a podiatric system or a podiatric tool for diagnostic, therapeutic, and/or rehabilitative functions before and/or during and/or after surgical or other podiatric treatment.

DDD. The smartphone device of any one of paragraphs A-Z and AA-ZZ and AAA-CCC, wherein the smartphone device and/or the apparatus and/or the footwear and/or the peripheral devices with sensors are used as a medical system or a medical tool to stimulate or retard structural bone growth and/or joint development in a child wearer prior to adulthood through non-surgical means.

EEE. The smartphone device of any one of paragraphs A-Z and AA-ZZ and AAA-DDD, wherein the smartphone device and/or the apparatus and/or the footwear and/or the peripheral devices with sensors are used as a medical system or a medical tool to prevent or reduce the gradual deterioration of bone and/or joint structure in an adult wearer through non-surgical means.

FFF. The smartphone device of any one of paragraphs A-Z and AA-ZZ and AAA-EEE, wherein the smartphone device and/or the apparatus and/or the footwear and/or the peripheral devices with sensors are used as a medical system or a medical tool to treat the deterioration of bone and/or joint structure in an elderly wearer through non-surgical means.

GGG. The smartphone device of any one of paragraphs A-Z and AA-ZZ and AAA-FFF, wherein the smartphone device is worn at the centerline of the rearmost portion of the wearer's belt or otherwise attached at or near the small of the wearer's lumbar back, centered between and at about the level of the illiac crests.

HHH. The smartphone device of any one of paragraphs A-Z and AA-ZZ and AAA-GGG, wherein the apparatus is a helmet and/or helmet padding and/or other padding or protective gear, including braces, with one or more bladders, compartments, chambers, sipes, or other portions that are actively configured by the smartphone device.

III. The smartphone device of any one of paragraphs A-Z and AA-ZZ and AAA-HHH, wherein the footwear is configured so that any part of or all of the configurable components of the footwear are located in a removable or fixed insert or a removable or fixed orthotic.

JJJ. The smartphone device of any one of paragraphs A-Z and AA-ZZ and AAA-III, wherein one or both of a wearer's footwear is configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole.

KKK. The smartphone device of any one of paragraphs A-Z and AA-ZZ and AAA-JJJ, wherein one or both of a wearer's concavely rounded footwear is configured to deform under the pressure of the wearer's body weight so as to flatten the rounding against the flat surface of the ground, in the same way that rounded portions of the wearer's foot sole flatten against the flat surface of the ground.

LLL. The smartphone device of any one of paragraphs A-Z and AA-ZZ and AAA-KKK, wherein one or both of a wearer's footwear is configured to include a sole which has a toe end portion and a heel end portion that have concavely rounded upper and lower surfaces relative to the position of the intended wearer's foot sole, as measured in at least in a sagittal plane cross-section taken along the long axis of the footwear; and/or wherein the upper and lower surfaces are substantially parallel; and/or wherein the concavely rounded lower surface extends to the most anterior extent and/or posterior extent of the sole; and/or one or both of a wearer's footwear is configured to include a flat portion between the toe end portion and heel end portion, as measured in at least in a sagittal plane cross-section taken along the long axis of the footwear.

MMM. The smartphone device of any one of paragraphs A-Z and AA-ZZ and AAA-LLL, wherein one or both sides of the sole has at least one flexibility groove located in the midfoot of the footwear sole proximate to a flexibility axis 122 located at about the posterior portion of the forefoot of the footwear sole and anterior to a position proximate to the base of the fifth metatarsal of the intended wearer's foot sole; and/or wherein the flexibility grove extends through part or all of the underneath portion between the sides of the footwear sides; and/or the footwear sole has other flexibility grooves.

NNN. The smartphone device of any one of paragraphs A-Z and AA-ZZ and AAA-MMM, wherein one or both of a wearer's concavely rounded footwear sole is formed from a flat sheet of heat and/or pressure-sensitive plastic and/or rubber, including foamed or blown, the flat sheet being put under heat and/or pressure by a press with upper and lower surfaces configured to produce the concavely rounded footwear sole; and/or the footwear sole is configured to include at least two layers that are laminated together with heat and/or pressure sensitive glue; and/or at least a part or all of the footwear sole is formed using a mold.

OOO. The smartphone device of any one of paragraphs A-Z and AA-ZZ and AAA-NNN, wherein one or both of a wearer's footwear sole is configured to have at least a semi-thong positioned to be located between the big toe and second toe of the intended wearer's foot; the semi-thong is fixed, fastened, or embedded in only to the upper surface and/or other portions of the footwear sole and is not fixed to and/or contacting a portion of the footwear upper or straps; and/or optional semi-thongs positioned to be located between one or more or all of the other toes of the wearer's foot sole; and/or the semi-thong has a round, an oval, or an anthropomorphically-determined shape, as viewed in a horizontal cross-section; and/or the semi-thong is constructed of plastic and/or rubber, including foamed or blown; and/or the semi-thong is configured to have at least one softer material on the outer surface and a core of at least one firmer material inside; and/or the semi-thong is configured to form a portion of the bottom surface the footwear sole; and/or the semi-thong is configured to be temporarily fastened to at least a portion of the footwear upper or strap; and/or wherein the semi-thong has a strut extending forward between the toes that serves as a protective partition between the toes.

PPP. The smartphone device of any one of paragraphs A-Z and AA-ZZ and AAA-OOO, wherein one or both of a wearer's most minimalist footwear is a footwear sole and/or a sock that is configured to include only a fabric layer, a traction coating layer on the outer surface of the fabric, and a traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein one or both of a wearer's most minimalist footwear is a footwear sole and/or a sock that is configured to include only the fabric, which is fabricated with a thread coated with a traction coating layer.

QQQ. The smartphone device of any one of paragraphs A-Z and AA-ZZ and AAA-PPP, wherein one or both of a wearer's most minimalist footwear is a footwear sole and/or a sock that is configured to include at least one fabric layer, at least one traction coating layer on the outer surface of the fabric, and at least one traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein the fabric is fabricated with a thread coated with a traction coating layer.

RRR. The smartphone device of any one of paragraphs A-Z and AA-ZZ and AAA-QQQ, wherein a software app configures at least a portion of a part or all of the smartphone device and/or sensors and/or footwear and/or apparatus.

SSS. A sole and/or a removable inner sole insert for footwear, comprising: one or more bladders, compartments, chambers, internal sipes or other portions located in the sole and/or in a removable insert; one or more sensors located in or on the sole and/or in the removable sole insert and/or located in or on an insole; the one or more bladders, compartments, chambers, sipes or other portions and the one or more sensors being configured for control by a smartphone or other mobile computer device, general purpose or specialized; and/or the control is conducted through a wired or a wireless connection.

TTT. The sole and/or the removable sole insert of paragraph SSS, wherein one or both of a wearer's footwear and/or the removable inner sole insert for footwear is configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole; and/or wherein the lateral extent extends above the lowest point of the inner footwear surface.

UUU. The sole and/or the removable sole insert of paragraph SSS, wherein one or both of a wearer's footwear is configured to operate with and/or be controlled by the smartphone device of any one of paragraphs A-Z and AA-ZZ and AAA-RRR.

VVV. A sole and/or a removable inner sole insert for footwear for footwear, comprising: one or both of a wearer's footwear is configured to include a sole and/or the removable inner sole insert which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole; and/or wherein the lateral extent extends above the lowest point of the inner footwear surface.

WWW. A sole and/or a removable sole insert for footwear, comprising: one or both of a wearer's footwear sole and/or the removable sole insert is configured to have at least a semi-thong positioned to be located between the big toe and second toe of the intended wearer's foot; the semi-thong is fixed, fastened, or embedded in only to the upper surface and/or other portions of the footwear sole and is not fixed to and/or contacting a portion of the footwear upper or straps; and/or optional semi-thongs positioned to be located between one or more or all of the other toes of the wearer's foot sole; and/or the semi-thong has a round, an oval, or an anthropomorphic-ally-determined shape, as viewed in a horizontal cross-section; and/or the semi-thong is constructed of plastic and/or rubber, including foamed or blown; and/or the semi-thong is configured to have at least one softer material on the outer surface and a core of at least one firmer material inside; and/or the semi-thong is configured to form a portion of the bottom surface the footwear sole; and/or the semi-thong is configured to be temporarily fastened to at least a portion of the footwear upper or strap; and/or wherein the semi-thong has a strut extending forward between the toes that serves as a protective partition between the toes.

XXX. The sole and/or the removable sole insert of paragraph SSS, wherein one or both of a wearer's footwear is configured to include a sole which has concavely rounded upper and lower surfaces relative to the intended wearer's foot sole, as measured in at least in a frontal plane cross-section taken in the heel area, the forefoot, and in the midfoot area; and/or wherein the upper and lower surfaces are substantially parallel; and/or wherein the concavely rounded lower surface extends to the lateral extent of one or both sides of the sole.

YYY. A sole, comprising: one or both of a wearer's most minimalist footwear is a footwear sole and/or a sock that is configured to include only a fabric layer, a traction coating layer on the outer surface of the fabric, and a traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein one or both of a wearer's most minimalist footwear is a footwear sole and/or a sock that is configured to include only the fabric, which is fabricated with a thread coated with a traction coating layer; and/or the sole is configure to allow for a removable sole insert of any one of paragraphs SSS-UUU.

ZZZ. A sole, comprising: one or both of a wearer's most minimalist footwear is a footwear sole and/or a sock that is configured to include at least one fabric layer, at least one traction coating layer on the outer surface of the fabric, and at least one traction coating layer on the inner surface of the fabric; and/or wherein the coating layers are rubber and/or plastic, including foamed and/or blown; and/or wherein one or both of the coating layers are continuous or formed in a geometric or other pattern or randomly oriented and/or irregularly shaped; and/or the minimalist footwear is configured to include a midsole insert and/or orthotic; and/or wherein the fabric is fabricated with a thread coated with a traction coating layer; and/or the sole is configure to allow for a removable sole insert of any one of paragraphs SSS-UUU.

AAAA. An apparatus, comprising: one or more bladders, compartments, chambers, sipes or other portions located in the apparatus; one or more sensors located in or on the apparatus; the one or bladders, compartments, chambers, sipes or other portions and the one or more sensors being configured for control by a smartphone or other mobile computer device, general purpose or specialized; and/or the control is conducted through a wired or a wireless connection.

BBBB. The apparatus of paragraph AAAA, wherein the apparatus is configured to operate with and/or be controlled by the smartphone device of any one of paragraphs A-Z and AA-ZZ and AAA-RRR.

CCCC. An article of apparel or equipment, comprising: the article of apparel or equipment can be configured to include wiring to connect the smartphone device to the apparatus and/or either or both of the footwear soles and/or one or more peripheral devices with at least one remote senor; and/or wherein the smartphone device is configured to provide power to the apparatus and/or footwear soles and/or peripheral devices.

DDDD. A helmet or other protective equipment including braces and body armor, comprising: an outer coating of Teflon™

EEEE. The smartphone device of any one of paragraphs A-Z and AA-ZZ and AAA-QQQ, wherein the smartphone device or apparatus is configured to include an outer coating of Teflon™.

The invention claimed is:

1. A computer system used for medical care connected to sensor-equipped smartphones connected to one or more sensors and smartphone-configurable structures in footwear soles, the computer system employing big data techniques in a database including a multitude of users of footwear including the footwear soles to compare the users' smartphone data to find correlations used for medical care of the users' structural or functional problems, to optimize corrections to the users' impairment from elevated shoe soles, comprising:
   a Web site and/or a cloud array of computers;
   wherein the computer system is configured to have a connection to a smartphone or other mobile computer device including a gyroscope and/or an accelerometer and the computer system is configured to use the device and the connection to control a configuration of:
      one or more sensors and one or more computer-controlled bladders, compartments, chambers and internal sipes located in a footwear sole or a removable inner sole insert of both shoes or other footwear of the user; and
      one or more sensors located on or in bodies of the users; and
   wherein the computer system is further configured to use the device and the connection to:
   transmit data to the computer system for storage and/or shared or independent processing and/or analysis,
   process data received from the one or more sensors located in either one or both of the sole or the removable inner sole insert of the user, and from the one or more sensors located on or the bodies of the users,
      use at least the processed data to alter the configuration of the one or more bladders, compartments, chambers and internal sipes of the footwear of the user,
      measure the relative positions to each other of a wearer's right and left feet during a stance phase of locomotion so as to determine a degree of crossover of right and/or left feet across a centerline of the wearer's body, as measured in a frontal plane during the stance phase of locomotion, and
      then test a series of configuration settings in order to reduce or eliminate the crossover.

2. The computer system as claimed in claim 1, wherein the database is configured to include millions of users.

3. The computer system as claimed in claim 1, wherein the database includes the data from the smartphones of the users and each of the smartphones is configured to perform a configuration optimizing operation of the configurable structures of the footwear soles hundreds or thousands or millions or billions of times.

4. The computer system as claimed in claim 1, wherein at least one said sensor located in or on the body of the user is located in, on, or near the head of the user; and
wherein the computer system is further configured to control the configuration of the one or more bladders, compartments, chambers and internal sipes by using the device and the connection to:
process data received from the at least one sensor located in, on, or near the head of the user, and
use at least the processed data from the sensor located in, on, or near the head of the user to alter a configuration of the one or more bladders, compartments, chambers and internal sipes of the user.

5. The computer system as claimed in claim 1, comprising at least one sensor located in the device and wherein at least one said sensor located in or on the body of the user is located in, on, or near the head of the user; and
wherein the computer system is further configured to control the configuration of the one or more bladders, compartments, chambers and internal sipes by using the device and the connection to:
process data received from the at least one sensor located in the device, and
use at least the processed data from the at least one sensor located in, on, or near the head of the user to alter a configuration of the one or more bladders, compartments, chambers and internal sipes of the user.

6. The computer system as claimed in claim 4, wherein the at least one sensor located in, on, or near the head of the user includes a motion sensor and is located and used to measure at least motion of the head of the user.

7. The computer system as claimed in claim 1, wherein at least one said sensor located in or on the body of the user is located in, on, or near the center of gravity of the user and on any article of apparel or personal equipment, including protective padding or armor, braces, prosthetics, or in any manner is attached or embedded in clothing, or attached with tape or a bandage or glue, or worn or attached onto or implanted in the wearer's body, temporarily in a body piercing or permanently in a body implant.

8. The computer system of claim 1, wherein the computer system is further configured to share access to the computer system among one or more authorized third parties and/or the user.

9. The computer system of claim 8, wherein the computer system is further configured for conducting real time or subsequent testing involving the one or more authorized third parties.

10. The computer system of claim 9, wherein the computer system is further configured for conducting real time or subsequent testing involving one said authorized third party who is a licensed doctor or a licensed podiatrist.

11. The computer system of claim 9, wherein the computer system is further configured for conducting real time or subsequent testing involving one said authorized third party who is a biomechanics specialist or other professional or semi-professional technician.

12. The computer system of claim 9, wherein the computer system is further configured to analyze test data sets of groups or categories of the users.

13. The computer system of claim 1, wherein the computer system is configured to use the device to alter either or both of the footwear soles including at least a magnetorheological fluid located in at least one of the one or more bladders, compartments, chambers and internal sipes, the magnetorheological fluid being controlled at least in part or completely by the device; and/or
wherein the computer system is configured to use the device to alter either or both of the footwear soles including at least one valve located between two or more of said bladders, compartments, chambers and internal sipes, the at least one valve being controlled at least in part or completely by the device; and/or
wherein the computer system is configured to use the device to alter either or both of the footwear soles including at least one electric and/or electronic and/or electromechanical component that is controlled at least in part or completely by the device.

14. The computer system of claim 1, wherein the computer system is configured to use the device to control the configuration of one or more footwear soles of the user by altering a relative longitudinal height, including positive or negative heel lift, or negative or positive forefoot lift, and/or a relative side-to-side height between lateral and medial sides, and/or a relative height between right and left footwear soles, or a combination of these relative height alterations; and/or
wherein the computer system is configured to use the device to control the configuration of one or more footwear soles of the user by altering relative longitudinal firmness between heel area and forefoot area and/or side-to-side firmness between lateral and medial side areas, and/or relative firmness between right and left footwear soles, or a combination of these relative firmness alterations; and/or
wherein the computer system is configured to use the device to control the configuration of one or more footwear soles of the user by altering relative height or firmness under one or more of the foot bones of the user, including under a calcaneus, a lateral calcaneal tuberosity, a base of a fifth metatarsal, a longitudinal arch, a metatarsal arch, each head of a metatarsal, and each distal phalange, including a hallux or big toe; and/or
wherein the computer system is configured to use the device to control the footwear configuration at least once per full operation cycle or locomotion stride, many times per full operation cycle or locomotion stride, once per many full operation cycles or locomotion strides, or based on a set time period of any duration or based on another test condition.

15. The computer system of claim 1, wherein the computer system is configured to use the device to:
record a first data set for a first configuration of the footwear and a second test data set for a second configuration of the footwear, each said data set consisting of measurements of force and/or relative pressure distribution of the user's footsole on an upper surface of the footwear during the user's locomotion or other physical activity, as measured in at least one plane (1D) or in two planes (2D) or in three planes (3D) and/or including time or other measurements, the footwear upper surface including at least a multitude or 20 or 50 or 100 or 500 or 1,000 or 4,000, or 16,000 individual pressure sensors;

compare the first test data set and the second test data set with a preferred data set for measurements of the force and/or the relative pressure distribution of the foot sole of a model wearer or wearers on an upper surface of the footwear during the locomotion or other physical activity, as measured in at least one plane (1D) or in two planes (2D) or in three planes (3D) and/or including time or other measurements; and select the configuration of the footwear that produced the test data set for the force or relative pressure distribution that is closest to the preferred data set for the force or relative pressure distribution and to reject the other configuration, thereby completing at least one full cycle of an operation to optimize the configuration of the footwear; and wherein the optimizing operation is used to reduce a range of pronation and/or supination of the user's foot and ankle during a landing phase of locomotion through active configuration of either or both of the footwear soles.

16. The computer system of claim 1, wherein the computer system is configured to use the device to perform an optimizing operation whereby the device actively configures either or both of the footwear soles to change a motion of a center of force on a surface of the footwear for either or both of the user's feet during locomotion.

17. The computer system of claim 1, wherein the computer system is configured to proactively and/or reactively alter both footwear soles or sole inserts to control the relative foot position between the right and left feet of the user, such as in order to alter the neutral position of either or both feet separately toward a more generally supinated or pronated position.

18. The computer system of claim 1, wherein the computer system uses a barefoot model to configure the device and the footwear with sensors and/or with other sensors to be a medical or podiatric system or a medical or podiatric tool for diagnostic, therapeutic, and/or rehabilitative functions before and/or during and/or after surgical or other medical or podiatric treatment through non-surgical means; and/or to stimulate or retard structural bone growth and/or joint development in a child wearer prior to adulthood through non-surgical means or to reduce gradual deterioration of bone and/or joint structure of an adult wearer or an elderly wearer through non-surgical means.

19. The computer system of claim 1, wherein the computer system is configured to use the device to carry out the following steps:

first, control the one or more bladders, compartments, chambers and internal sipes by establishing a first configuration setting of said one or more bladders, compartments, chambers and internal sipes for at least a first test during locomotion or other physical activity of the user;

second, control the one or more bladders, compartments, chambers and internal sipes by establishing a second configuration setting of said one or more bladders, compartments, chambers and internal sipes that is different from the first configuration setting for at least a second test during locomotion or other physical activity of the user;

third, process measurement data from the first and second tests received from the sensors located in both footwear soles or inserts and from at least one sensor in the device and/or in another device and/or located in an apparatus;

fourth, compare the data from the first and second tests with a preferred data set; and fifth, select one said configuration setting of the one or more bladders, compartments, chambers and internal sipes from the first or second test that produced data that is closest to matching the preferred data set.

20. The computer system of claim 1, wherein the computer system is configured to use the device to record and compare multiple test data sets consisting of measurements of relative motion during the user's locomotion or other physical activity of a position at or near to a part of the body of the user; as measured in at least one plane (1D) or in two planes (2D) or in three planes (3D) and/or including time or other measurements.

21. The computer system of claim 1, wherein the computer system is configured to use the device to record and compare multiple test data sets including data from at least one said sensor located in or on the body of the user that is located in, on, or near a center of gravity of the user and consisting of measurements of relative motion during the user's locomotion or other physical activity of a position that is at or near a center of gravity (C.G.) of a body of the user, as measured in at least one plane (1D) or in two planes (2D) or in three planes (3D) and/or including time or other measurements.

22. The computer system of claim 1, wherein the computer system is configured to use at least measurements in two planes or dimensions (2D) or in three planes or dimensions (3D) from at least the one sensor located in, on, or near a center of gravity of the user.

23. The computer system of claim 1, wherein the smartphone or other mobile computer device includes both the gyroscope and the accelerometer.

24. The computer system of claim 1, wherein the computer system is configured to utilize computer control located in the footwear to control the one or more bladders, compartments, chambers and internal sipes.

25. The computer system of claim 1, wherein the computer system is configured to use the device to receive input from at least one sensor selected from the group consisting of a gyroscope and/or an accelerometer in the smartphone device located in an apparatus worn or carried by the user, attached to the user, or implanted in the user, the apparatus being separate from the footwear of the user.

26. The computer system of claim 1, wherein the computer system is configured to use the device to receive input from the at least one gyroscope and/or accelerometer and/or other relative and/or absolute motion sensor and/or pressure sensor and/or force sensor located in an apparatus, the apparatus comprising any article of clothing or personal equipment, including earphones or earplugs, helmet, eyeglasses, watch, belt, waistband, elastic underwear, armband, a taped or bandaged attachment, necklace, lanyard, cervical collar, ring, headband, body piercing, or that are in any manner attached or embedded in conventional or specialized clothing worn or attached to the skin of a wearer, or padding or braces, armor, or seating or furniture, or worn or attached onto or implanted in the wearer's body, temporarily in a body piercing or permanently in a body implant.

27. The computer system of claim 1, wherein the computer system is configured to use the device to control an apparatus worn or carried by the user, attached to the user, or implanted in the user, the apparatus or the other device being separate from the footwear of the user or the computer system is configured to control the apparatus, the apparatus including one or more bladders, compartments, chambers and internal sipes that are configured for computer control so that the device or the computer system alters the configuration of the one or more bladders, compartments, chambers and internal sipes of the apparatus.

28. The computer system of claim 4, wherein the computer system is configured to use the device to:
   measure and receive ID or 2D or 3D data of the relative motion of the user's head during locomotion using earplug sensor fixation by the ear canals of the user's head and compare the user's head motion data with the user's center of gravity (C.G.) data during locomotion or other physical activity; and/or
   send either or both sets of data to the computer system and/or a third party for comparison and/or to conduct other functions in a shared operation, including a partially shared operation.

29. The computer system as claimed in claim 1, wherein the computer system is configured to cause the device to control the configuration of:
   the one or more computer-controlled bladders, compartments, chambers and internal sipes located in the footwear sole or the removable inner sole insert of both the shoes or other footwear of the user, and
   wherein the computer system is further configured to cause the device to:
transmit data to the computer system for storage and/or shared or independent processing and/or analysis,
   process data received from the one or more sensors located in either one or both of the sole or the removable inner sole insert of the user and from the at least one sensor located in, on, or near a center of gravity of the user, and
   use the processed data to alter the configuration of the one or more bladders, compartments, chambers and internal sipes of the user.

30. The computer system as claimed in claim 1, wherein the one or more sensors includes an accelerometer located in, on, or near the center of gravity of the user.

* * * * *